US008551625B2

(12) United States Patent
Nomura et al.

(10) Patent No.: US 8,551,625 B2
(45) Date of Patent: Oct. 8, 2013

(54) DERIVATIVE WITH HETEROAROMATIC RING, AND LIGHT-EMITTING ELEMENT, LIGHT-EMITTING DEVICE, LIGHTING DEVICE, AND ELECTRONIC DEVICE USING DERIVATIVE WITH HETEROAROMATIC RING

(75) Inventors: Hiroko Nomura, Fukuoka (JP); Hiroshi Kadoma, Kanagawa (JP); Sachiko Kawakami, Kanagawa (JP); Nobuharu Ohsawa, Kanagawa (JP); Satoshi Seo, Kanagawa (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 380 days.

(21) Appl. No.: 12/750,110

(22) Filed: Mar. 30, 2010

(65) Prior Publication Data
US 2010/0243959 A1 Sep. 30, 2010

(30) Foreign Application Priority Data

Mar. 31, 2009 (JP) .................................. 2009-086528

(51) Int. Cl.
| | | |
|---|---|---|
| H01L 51/54 | (2006.01) | |
| C09K 11/06 | (2006.01) | |
| C07D 249/06 | (2006.01) | |
| C07D 403/02 | (2006.01) | |

(52) U.S. Cl.
USPC ........... 428/690; 428/917; 313/504; 313/506; 252/301.16; 548/266.4; 548/364.7

(58) Field of Classification Search
None
See application file for complete search history.

(56) References Cited

U.S. PATENT DOCUMENTS

| | | | |
|---|---|---|---|
| 5,756,224 A | 5/1998 | Borner et al. | |
| 6,262,441 B1 | 7/2001 | Bohler et al. | |
| 6,329,082 B1 | 12/2001 | Kreuder et al. | |
| 6,489,638 B2 | 12/2002 | Seo et al. | |
| 6,566,807 B1 | 5/2003 | Fujita et al. | |
| 6,677,621 B2 | 1/2004 | Yamazaki et al. | |
| 6,692,845 B2 | 2/2004 | Maruyama et al. | |
| 6,822,629 B2 | 11/2004 | Yamazaki et al. | |
| 2001/0045565 A1 | 11/2001 | Yamazaki | |
| 2002/0034659 A1 | 3/2002 | Nishi et al. | |
| 2002/0121638 A1 | 9/2002 | Grushin et al. | |
| 2004/0086745 A1* | 5/2004 | Iwakuma et al. | 428/690 |
| 2004/0156982 A1 | 8/2004 | Maruyama et al. | |
| 2004/0173811 A1 | 9/2004 | Yamazaki et al. | |
| 2005/0082970 A1 | 4/2005 | Yamazaki et al. | |
| 2005/0233170 A1 | 10/2005 | Yamazaki | |
| 2005/0249976 A1* | 11/2005 | Iwakuma et al. | 428/690 |
| 2009/0066231 A1* | 3/2009 | Oka et al. | 313/504 |
| 2012/0007063 A1* | 1/2012 | Langer et al. | 257/40 |
| 2012/0049768 A1* | 3/2012 | Seo et al. | 315/362 |
| 2012/0298975 A1 | 11/2012 | Iwakuma et al. | |
| 2012/0319099 A1 | 12/2012 | Iwakuma et al. | |

FOREIGN PATENT DOCUMENTS

| | | |
|---|---|---|
| CN | 1701111 | 11/2005 |
| CN | 101171239 | 4/2008 |
| EP | 1 489 155 A1 | 12/2004 |
| EP | 2 169 028 A1 | 3/2010 |
| JP | 2007-335852 | * 12/2007 |
| JP | 2008-024698 | * 2/2008 |
| WO | WO 2006/114377 A1 | 11/2006 |

OTHER PUBLICATIONS

Machine-generated English translation (Part 1) for JP 2008-024698, which was published Feb. 2008.*
Machine-generated English translation (Part 2) for JP 2008-024698, which was published Feb. 2008.*
M.A. Baldo et al., "Very high efficiency green organic light-emitting devices based on electrophosphorescence," *Applied Physics Letters*, vol. 75, No. 1, 1999, pp. 4-6.
Chinese Office Action (Application No. 201010158592.1; CN12292) Dated: Mar. 25, 2013.

* cited by examiner

*Primary Examiner* — Dawn L. Garrett
(74) *Attorney, Agent, or Firm* — Nixon Peabody LLP; Jeffrey L. Costellia

(57) ABSTRACT

A derivative with a heteroaromatic ring represented by General Formula (G1) is provided. $R^{11}$ to $R^{20}$ in the formula independently represent a hydrogen atom, an alkyl group having 1 to 4 carbon atoms, or an aryl group having 6 to 10 carbon atoms in a ring. J represents a substituted or unsubstituted arylene group having 6 to 12 carbon atoms in a ring. Note that α and β may be bonded to each other to form a carbazole skeleton. Het is a substituent represented by General Formula (S1-1) or (S1-2). In General Formulae (S1-1) and (S1-2), $Ar^1$ to $Ar^4$ are independently a substituted or unsubstituted aryl group having 6 to 10 carbon atoms in a ring. $R^1$ is a hydrogen atom, an alkyl group having 1 to 4 carbon atoms, or an aryl group having 6 to 10 carbon atoms in a ring.

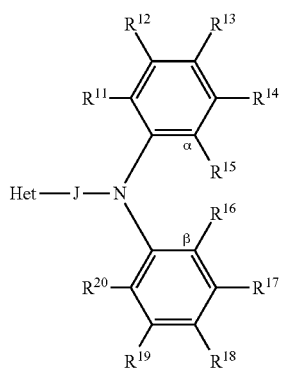

(G1)

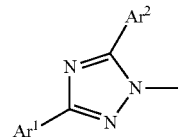

(S1-1)

-continued

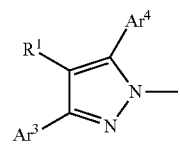

(S1-2)

22 Claims, 19 Drawing Sheets

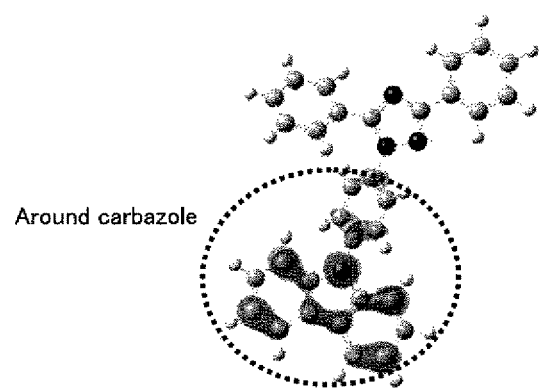
FIG. 22A: The Highest Occupied Molecular Orbital (HOMO)
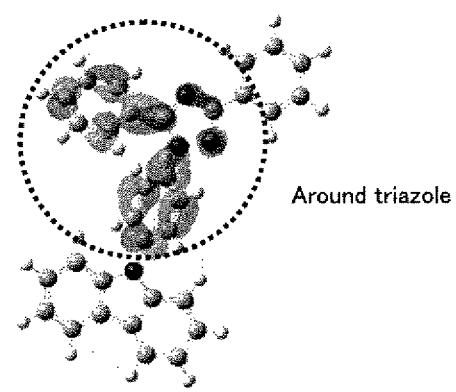
FIG. 22B: The Lowest Unoccupied Molecular Orbital (LUMO)

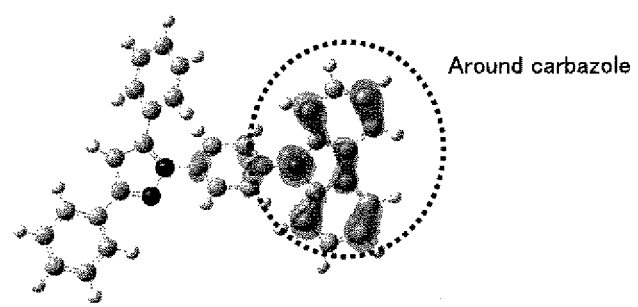
FIG. 23A: The Highest Occupied Molecular Orbital (HOMO)
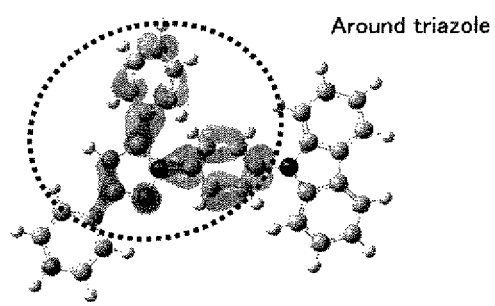
FIG. 23B: The Lowest Unoccupied Molecular Orbital (LUMO)

DERIVATIVE WITH HETEROAROMATIC RING, AND LIGHT-EMITTING ELEMENT, LIGHT-EMITTING DEVICE, LIGHTING DEVICE, AND ELECTRONIC DEVICE USING DERIVATIVE WITH HETEROAROMATIC RING

BACKGROUND OF THE INVENTION

1. Field of the Invention

The present invention relates to a derivative with a heteroaromatic ring, and a light-emitting element, a light-emitting device, a lighting device, and an electronic device each using a derivative with a heteroaromatic ring.

2. Description of the Related Art

In recent years, research and development of light-emitting elements using electroluminescence have been extensively conducted. In the basic structure of such a light-emitting element, a layer including a light-emitting substance is interposed between a pair of electrodes. By applying a voltage to this element, light emission can be obtained from the light-emitting substance.

Since this type of light-emitting element is a self-luminous type, it has advantages over a liquid crystal display in that visibility of a pixel is high and that no backlight is needed. Therefore, light-emitting elements are thought to be suitable as flat panel display elements. Further, such a light-emitting element also has advantages in that the element can be formed to be thin and lightweight and that response speed is very high.

Further, since this type of light-emitting element can be formed to have a film shape, surface light emission can be easily obtained. This feature is difficult to realize with point light sources typified by a filament lamp and an LED or with linear light sources typified by a fluorescent light. Therefore, such light-emitting elements also have a high utility value as a surface light source that can be applied to lighting or the like.

Light-emitting elements using electroluminescence are broadly classified according to whether their light-emitting substance is an organic compound or an inorganic compound. When an organic compound is used as a light-emitting substance, by application of a voltage to a light-emitting element, electrons and holes are injected from a pair of electrodes into a layer including a light-emitting organic compound, so that a current flows. Accordingly, the carriers (electrons and holes) are recombined, and thus, the light-emitting organic compound is excited. The light-emitting organic compound returns to a ground state, thereby emitting light.

Because of such a mechanism, the light-emitting element is called a current-excitation light-emitting element. Note that an excited state of an organic compound can be of two types: a singlet excited state and a triplet excited state, and luminescence from the singlet excited state ($S^*$) is referred to as fluorescence, and luminescence from the triplet excited state ($T^*$) is referred to as phosphorescence. Furthermore, it is thought that the ratio of $S^*$ to $T^*$ in a light-emitting element is statistically 1:3.

At room temperature, a compound that converts a singlet excited state into luminescence (hereinafter referred to as a fluorescent compound) exhibits only luminescence from the singlet excited state (fluorescence), not luminescence from the triplet excited state (phosphorescence). Therefore, the internal quantum efficiency (ratio of generated photons to injected carriers) of a light-emitting element using a fluorescent compound is thought to have a theoretical limit of 25% on the basis that $S^*:T^*=1:3$.

In contrast, by using a compound that converts a triplet excited state into luminescence (hereinafter referred to as a phosphorescent compound), an internal quantum efficiency of 75% to 100% can theoretically be achieved. That is, emission efficiency can be three to four times as high as that of a fluorescent compound. From such a reason, in order to achieve a light-emitting element with high efficiency, a light-emitting element using a phosphorescent compound has been actively developed recently (e.g., see Non Patent Document 1).

When a light-emitting layer of a light-emitting element is formed using a phosphorescent compound as described above, in order to suppress concentration quenching of the phosphorescent compound or quenching due to triplet-triplet annihilation, the light-emitting layer is often formed so that the phosphorescent compound is dispersed in a matrix including another substance. In that case, a substance serving as a matrix is referred to as a host material, and a substance that is dispersed in a matrix, such as a phosphorescent compound, is referred to as a guest material.

When a phosphorescent compound is used as a guest material, a host material is needed to have triplet excitation energy (an energy difference between a ground state and a triplet excited state) higher than the phosphorescent compound. It is known that CBP, which is used as a host material in Non-Patent Document 1, has higher triplet excitation energy than a phosphorescent compound which exhibits emission of green to red light, and is widely used as a host material in the phosphorescent compound.

However, although CBP has high triplet excitation energy, it is poor in ability to receive holes or electrons; therefore, there is a problem in that driving voltage of the light-emitting element gets higher. Therefore, a substance that has high triplet excitation energy and also can easily accept or transport both holes and electrons (i.e. a bipolar substance) is required as a host material for a phosphorescent compound.

Furthermore, because singlet excitation energy (an energy difference between a ground state and a singlet excited state) is greater than triplet excitation energy, a material that has high triplet excitation energy will also have high singlet excitation energy. Consequently, a substance that has high triplet excitation energy and a bipolar property is also useful in a light-emitting element formed using a fluorescent compound as a light-emitting substance.

[Reference]
[Non-Patent Document]
[Non-Patent Document 1] M. A. Baldo, and four others, *Applied Physics Letters*, vol. 75, No. 1, pp. 4-6, 1999

SUMMARY OF THE INVENTION

It is an object of an embodiment of the present invention to provide a novel derivative with a heteroaromatic ring as a substance having high excitation energy, in particular, a substance having high triplet excitation energy. It is another object of an embodiment of the present invention to provide a novel derivative with a heteroaromatic ring having a bipolar property. It is still another object of an embodiment of the present invention to improve element characteristics of a light-emitting element by application of a novel derivative with a heteroaromatic ring to a light-emitting element. Further, it is another object of an embodiment of the present invention to provide a light-emitting device, an electronic device, and a lighting device each having low power consumption and low driving voltage.

One embodiment of the present invention is a derivative with a heteroaromatic ring represented by General Formula (G1) below.

[Chemical Formula 1]

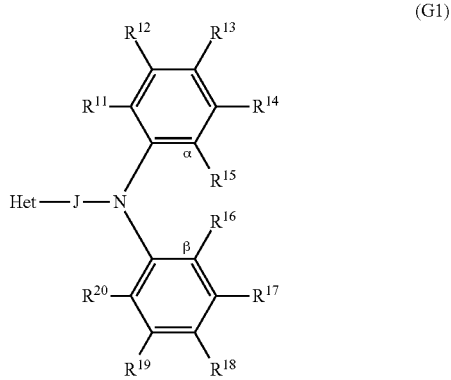

(G1)

In General Formula (G1), $R^{11}$ to $R^{20}$ are independently a hydrogen atom, an alkyl group having 1 to 4 carbon atoms, or a substituted or unsubstituted aryl group having 6 to 10 carbon atoms in a ring. When $R^{11}$ to $R^{20}$ each have a substituent, an alkyl group having 1 to 4 carbon atoms or an aryl group having 6 to 10 carbon atoms in a ring can be independently given as an example of the substituent. J represents a substituted or unsubstituted arylene group having 6 to 12 carbon atoms. When J has a substituent, an alkyl group having 1 to 4 carbon atoms can be given as an example of the substituent. Note that α and β may be bonded to each other to form a carbazole skeleton. Het is a substituent represented by General Formula (S1-1) or (S1-2) below.

[Chemical Formula 3]

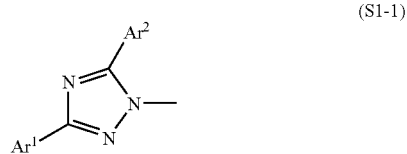

(S1-1)

In General Formula (S1-1), $Ar^1$ and $Ar^2$ are independently a substituted or unsubstituted aryl group having 6 to 10 carbon atoms in a ring. When $Ar^1$ and $Ar^2$ each have a substituent, an alkyl group having 1 to 4 carbon atoms or an aryl group having 6 to 10 carbon atoms in a ring can be independently given as an example of the substituent.

[Chemical Formula 3]

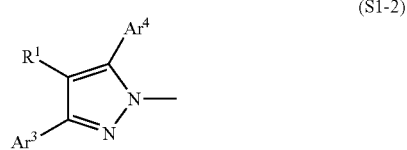

(S1-2)

In General Formula (S1-2), $Ar^3$ and $Ar^4$ are independently a substituted or unsubstituted aryl group having 6 to 10 carbon atoms in a ring. $R^1$ is a hydrogen atom, an alkyl group having 1 to 4 carbon atoms, or an aryl group having 6 to 10 carbon atoms in a ring. When $Ar^3$ and $Ar^4$ each have a substituent, an alkyl group having 1 to 4 carbon atoms or an aryl group having 6 to 10 carbon atoms in a ring can be independently given as an example of the substituent.

Further, another embodiment of the present invention is a derivative with a heteroaromatic ring represented by General Formula (G2) below.

[Chemical Formula 4]

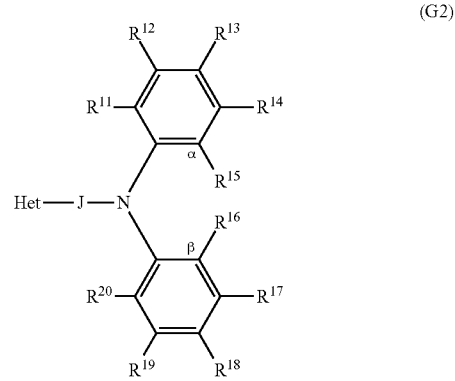

(G2)

In General Formula (G2), $R^{11}$ to $R^{20}$ are independently a hydrogen atom, an alkyl group having 1 to 4 carbon atoms, or a substituted or unsubstituted aryl group having 6 to 10 carbon atoms in a ring. When $R^{11}$ to $R^{20}$ each have a substituent, an alkyl group having 1 to 4 carbon atoms or an aryl group having 6 to 10 carbon atoms in a ring can be independently given as an example of the substituent. J represents a substituted or unsubstituted arylene group having 6 to 12 carbon atoms. When J has a substituent, an alkyl group having 1 to 4 carbon atoms can be given as an example of the substituent. Note that α and β may be bonded to each other to form a carbazole skeleton. Het is a substituent represented by General Formula (S2-1) or (S2-2) below.

[Chemical Formula 5]

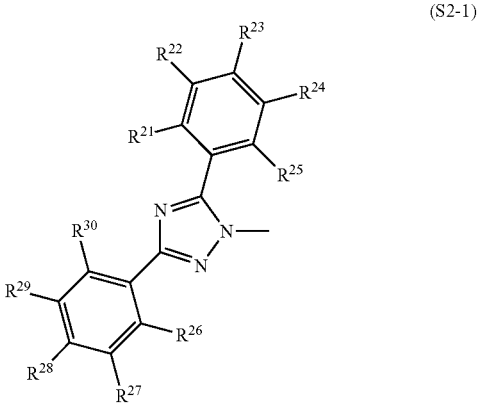

(S2-1)

In General Formula (S2-1), $R^{21}$ to $R^{30}$ are independently a hydrogen atom, an alkyl group having 1 to 4 carbon atoms, or an aryl group having 6 to 10 carbon atoms in a ring.

[Chemical Formula 6]

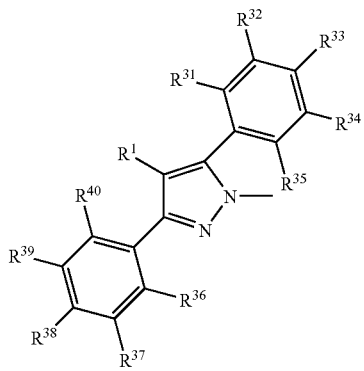

(S2-2)

In General Formula (S2-2), $R^1$ and $R^{31}$ to $R^{40}$ are independently a hydrogen atom, an alkyl group having 1 to 4 carbon atoms, or an aryl group having 6 to 10 carbon atoms in a ring.

Another embodiment of the present invention is a derivative with a heteroaromatic ring represented by General Formula (G3) below.

[Chemical Formula 7]

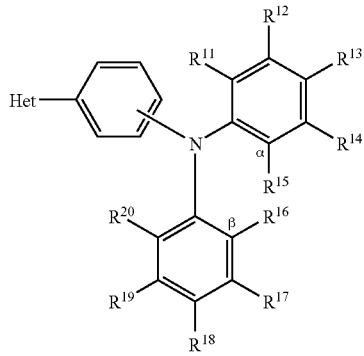

(G3)

In General Formula (G3), $R^{11}$ to $R^{20}$ are independently a hydrogen atom, an alkyl group having 1 to 4 carbon atoms, or a substituted or unsubstituted aryl group having 6 to 10 carbon atoms in a ring. When $R^{11}$ to $R^{20}$ each have a substituent, an alkyl group having 1 to 4 carbon atoms or an aryl group having 6 to 10 carbon atoms in a ring can be independently given as an example of the substituent. Note that α and β may be bonded to each other to form a carbazole skeleton. Het is a substituent represented by General Formula (S3-1) or (S3-2) below.

[Chemical Formula 8]

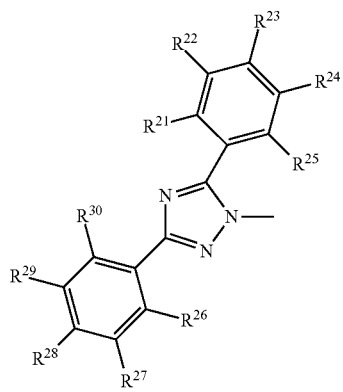

(S3-1)

In General Formula (S3-1), $R^{21}$ to $R^{30}$ are independently a hydrogen atom, an alkyl group having 1 to 4 carbon atoms, or an aryl group having 6 to 10 carbon atoms in a ring.

[Chemical Formula 9]

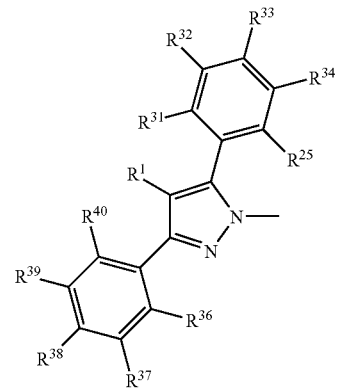

(S3-2)

In General Formula (S3-2), $R^1$ and $R^{31}$ to $R^{40}$ are independently a hydrogen atom, an alkyl group having 1 to 4 carbon atoms, or an aryl group having 6 to 10 carbon atoms in a ring.

Another embodiment of the present invention is a derivative with a heteroaromatic ring represented by General Formula (G4) below.

[Chemical Formula 10]

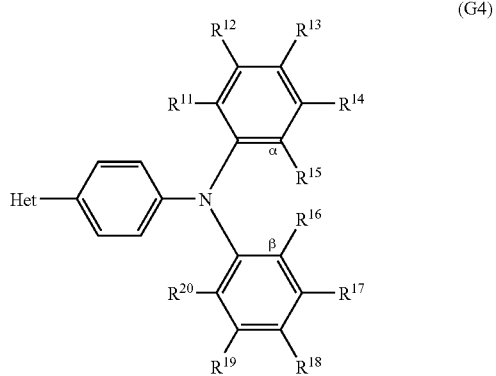

(G4)

In General Formula (G4), $R^{11}$ to $R^{20}$ are independently a hydrogen atom, an alkyl group having 1 to 4 carbon atoms, or a substituted or unsubstituted aryl group having 6 to 10 carbon atoms in a ring. When $R^{11}$ to $R^{20}$ each have a substituent, an alkyl group having 1 to 4 carbon atoms or an aryl group having 6 to 10 carbon atoms in a ring can be independently given as an example of the substituent. Note that α and β may be bonded to each other to form a carbazole skeleton. Bet is a substituent represented by General Formula (S4-1) or (S4-2) below.

[Chemical Formula 11]

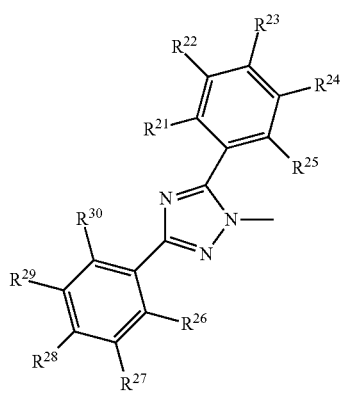

(S4-1)

In General Formula (S4-1), $R^{21}$ to $R^{30}$ are independently a hydrogen atom, an alkyl group having 1 to 4 carbon atoms, or an aryl group having 6 to 10 carbon atoms in a ring.

[Chemical Formula 12]

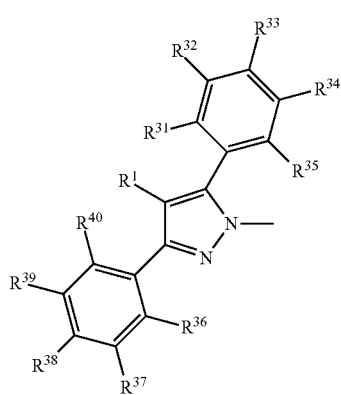

(S4-2)

In General Formula (S4-2), $R^1$ and $R^{31}$ to $R^{40}$ are independently a hydrogen atom, an alkyl group having 1 to 4 carbon atoms, or an aryl group having 6 to 10 carbon atoms in a ring.

Another embodiment of the present invention is a derivative with a heteroaromatic ring represented by General Formula (G5) below.

[Chemical Formula 13]

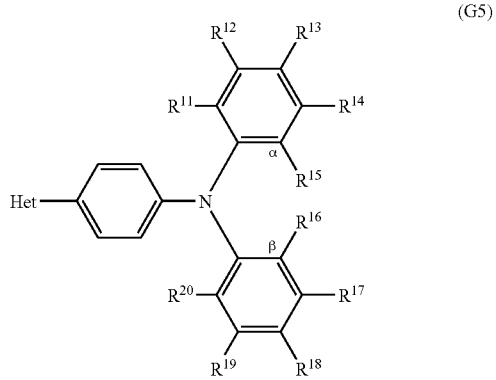

(G5)

In General Formula (G5), $R^{11}$ to $R^{20}$ are independently a hydrogen atom, an alkyl group having 1 to 4 carbon atoms, or a substituted or unsubstituted aryl group having 6 to 10 carbon atoms in a ring. When $R^{11}$ to $R^{20}$ each have a substituent, an alkyl group having 1 to 4 carbon atoms or an aryl group having 6 to 10 carbon atoms in a ring can be independently given as an example of the substituent. Note that α and β may be bonded to each other to form a carbazole skeleton. Het is a substituent represented by Structural Formula (S5-1) or General Formula (S5-2) below.

[Chemical Formula 14]

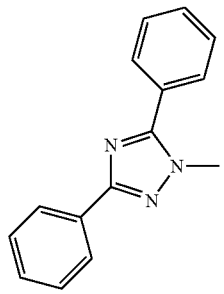

(S5-1)

[Chemical Formula 15]

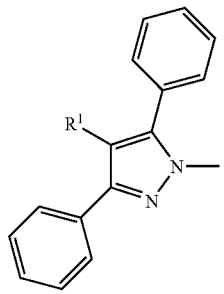

(S5-2)

In General Formula (S5-2), $R^1$ is a hydrogen atom, an alkyl group having 1 to 4 carbon atoms, or an aryl group having 6 to 10 carbon atoms in a ring.

Another embodiment of the present invention is a derivative with a heteroaromatic ring represented by General Formula (G6) below.

[Chemical Formula 16]

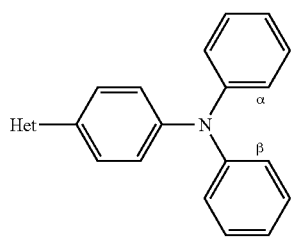
(G6)

In General Formula (G6), α and β may be bonded to each other to form a carbazole skeleton. Het is a substituent represented by Structural Formula (S6-1) or General Formula (S6-2) below.

[Chemical Formula 17]

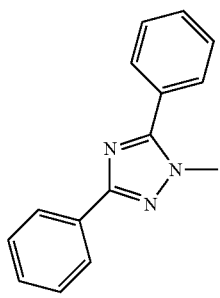
(S6-1)

[Chemical Formula 18]]

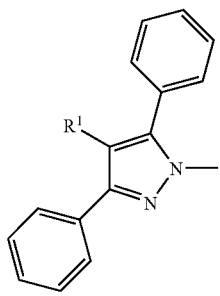
(S6-2)

In General Formula (S6-2), $R^1$ is a hydrogen atom, an alkyl group having 1 to 4 carbon atoms, or an aryl group having 6 to 10 carbon atoms in a ring.

Since the above-described derivatives with a heteroaromatic ring according to an embodiment of the present invention have a light-emitting property, as another structure of the present invention, a light-emitting element includes an EL layer between a pair of electrodes, and the EL layer includes any of the above-described derivatives with a heteroaromatic ring.

In addition, the derivatives with a heteroaromatic ring according to an embodiment of the present invention have high excitation energy. The derivatives with a heteroaromatic ring can transport both holes and electrons and is thus suitable for a host material of a light-emitting layer included in an EL layer. Accordingly, as another structure of the present invention, a light-emitting element includes an EL layer between a pair of electrodes, and a light-emitting layer included in the EL layer includes any of the above-described derivatives with a heteroaromatic ring and a light-emitting substance.

In particular, because the derivatives with a heteroaromatic ring according to an embodiment of the present invention have high triplet excitation energy, a phosphorescent compound is preferable for the light-emitting substance. With such a structure, a light-emitting element that is excellent in emission efficiency and driving voltage can be obtained.

Another structure of the present invention is a light-emitting device formed using any of the light-emitting elements described above. Further, another structure of the present invention is an electronic device formed using the light-emitting device according to an embodiment of the present invention. Furthermore, another structure of the present invention is a lighting device formed using the light-emitting device according to an embodiment of the present invention.

Further, an embodiment of the present invention includes a light-emitting device including any of the above-described light-emitting elements, and an electronic device and a lighting device each including the light-emitting device. It is to be noted that the "light-emitting device" in this specification refers to an image display device, a light-emitting device, or a light source (including a lighting device). Further, the light-emitting device includes any of the following modules in its category: a module in which a connector such as a flexible printed circuit (FPC), a tape automated bonding (TAB) tape, or a tape carrier package (TCP) is attached to a light-emitting device; a module having a TAB tape or a TCP provided with a printed wiring board at the end thereof; and a module having an integrated circuit (IC) directly mounted over a light-emitting element by a chip on glass (COG) method.

According to an embodiment of the present invention, a derivative with a heteroaromatic ring having high excitation energy, in particular, high triplet excitation energy can be obtained. In addition, a derivative with a heteroaromatic ring having a bipolar property of one embodiment of the present invention can be obtained. By forming a light-emitting element using a derivative with a heteroaromatic ring according to an embodiment of the present invention, a light-emitting element with high current efficiency can be formed.

Further, by using a light-emitting element according to an embodiment of the present invention, a light-emitting device and an electronic device each having low power consumption and low driving voltage can be obtained.

BRIEF DESCRIPTION OF THE DRAWINGS

FIGS. 22A and 22B show the highest occupied molecular orbital (HOMO) and the lowest unoccupied molecular orbital (LUMO) of CzTAZ(1H) (abbreviation), respectively.

FIGS. 23A and 23B show the highest occupied molecular orbital (HOMO) and the lowest unoccupied molecular orbital (LUMO) of CzPz (abbreviation), respectively.

DETAILED DESCRIPTION OF THE INVENTION

Figure 1:
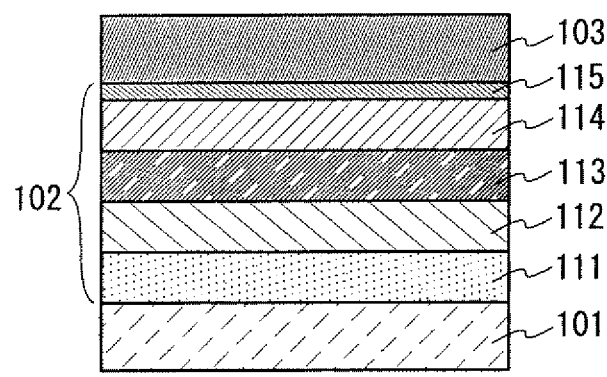
FIG. 1 illustrates a light-emitting element.

Hereinafter, Embodiments of the present invention will be described with reference to the drawings. Note that the present invention is not limited to the following description, and modes and details thereof can be modified in various ways without departing from the spirit and the scope of the present invention. Therefore, the invention should not be construed as being limited to the description in the following embodiment modes.

(Embodiment 1)

In this embodiment, a derivative with a heteroaromatic ring according to an embodiment of the present invention is described.

A derivative with a heteroaromatic ring according to an embodiment of the present invention is represented by General Formula (G1).

[Chemical Formula 19]

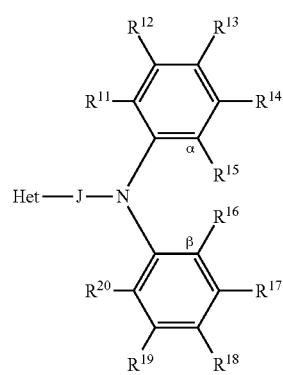

(G1)

In General Formula (G1), $R^{11}$ to $R^{20}$ are independently a hydrogen atom, an alkyl group having 1 to 4 carbon atoms, or a substituted or unsubstituted aryl group having 6 to 10 carbon atoms in a ring. When $R^{11}$ to $R^{20}$ each have a substituent, an alkyl group having 1 to 4 carbon atoms or an aryl group having 6 to 10 carbon atoms in a ring can be independently given as an example of the substituent. J represents a substituted or unsubstituted arylene group having 6 to 12 carbon atoms. When J has a substituent, an alkyl group having 1 to 4 carbon atoms can be given as an example of the substituent. Note that α and β may be bonded to each other to form a carbazole skeleton. Het is a substituent represented by General Formula (S1-1) or (S1-2) below.

[Chemical Formula 20]

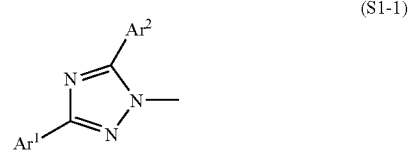

(S1-1)

In General Formula (S1-1), $Ar^1$ and $Ar^2$ are independently a substituted or unsubstituted aryl group having 6 to 10 carbon atoms in a ring. When $Ar^1$ and $Ar^2$ each have a substituent, an alkyl group having 1 to 4 carbon atoms or an aryl group having 6 to 10 carbon atoms in a ring can be independently given as an example of the substituent.

[Chemical Formula 21]

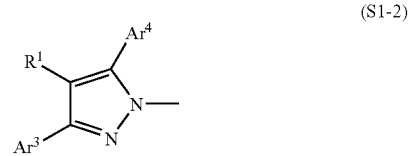

(S1-2)

In General Formula (S1-2), $Ar^3$ and $Ar^4$ are independently a substituted or unsubstituted aryl group having 6 to 10 carbon atoms in a ring. $R^1$ is a hydrogen atom, an alkyl group having 1 to 4 carbon atoms, or an aryl group having 6 to 10 carbon atoms in a ring. When $Ar^3$ and $Ar^4$ each have a substituent, an alkyl group having 1 to 4 carbon atoms or an aryl group having 6 to 10 carbon atoms in a ring can be independently given as an example of the substituent.

A derivative with a heteroaromatic ring according to an embodiment of the present invention is represented by General Formula (G2).

[Chemical Formula 22]

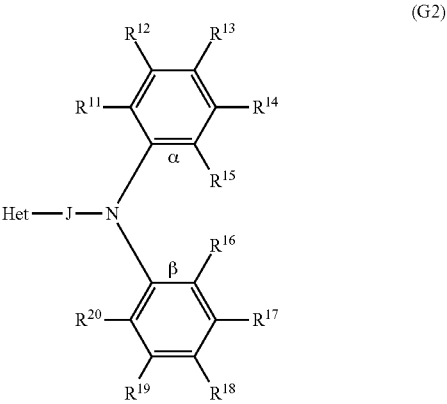

(G2)

In General Formula (G2), $R^{11}$ to $R^{20}$ are independently a hydrogen atom, an alkyl group having 1 to 4 carbon atoms, or a substituted or unsubstituted aryl group having 6 to 10 carbon atoms in a ring. When $R^{11}$ to $R^{20}$ each have a substituent, an alkyl group having 1 to 4 carbon atoms or an aryl group having 6 to 10 carbon atoms in a ring can be independently given as an example of the substituent. J represents a substituted or unsubstituted arylene group having 6 to 12 carbon atoms. When J has a substituent, an alkyl group having 1 to 4 carbon atoms can be given as an example of the substituent. Note that α and β may be bonded to each other to form a carbazole skeleton. Het is a substituent represented by General Formula (S2-1) or (S2-2) below.

[Chemical Formula 23]

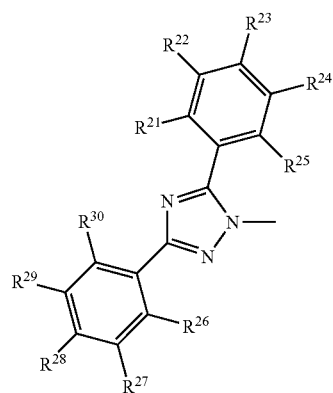

(S2-1)

In General Formula (S2-1). $R^{21}$ to $R^{30}$ are independently a hydrogen atom, an alkyl group having 1 to 4 carbon atoms, or an aryl group having 6 to 10 carbon atoms in a ring.

[Chemical Formula 24]

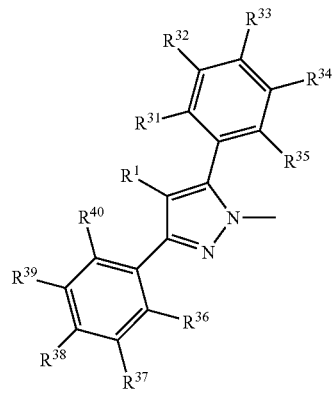

(S2-2)

In General Formula (S2-2), $R^1$ and $R^{31}$ to $R^{40}$ are independently a hydrogen atom, an alkyl group having 1 to 4 carbon atoms, or an aryl group having 6 to 10 carbon atoms in a ring.

A derivative with a heteroaromatic ring according to an embodiment of the present invention is represented by General Formula (G3).

[Chemical Formula 25]

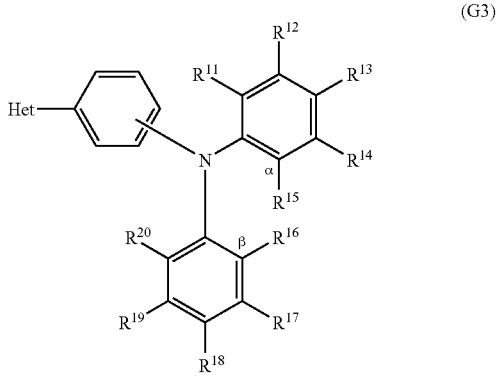

(G3)

In General Formula (G3), $R^{11}$ to $R^{20}$ are independently a hydrogen atom, an alkyl group having 1 to 4 carbon atoms, or a substituted or unsubstituted aryl group having 6 to 10 carbon atoms in a ring. When $R^{11}$ to $R^{20}$ each have a substituent, an alkyl group having 1 to 4 carbon atoms or an aryl group having 6 to 10 carbon atoms in a ring can be independently given as an example of the substituent. Note that α and β may be bonded to each other to form a carbazole skeleton. Het is a substituent represented by General Formula (S3-1) or (S3-2) below.

[Chemical Formula 26]

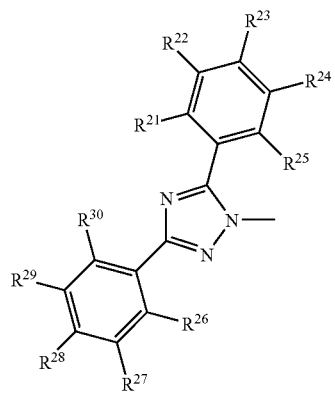

(S3-1)

In General Formula (S3-1), $R^{21}$ to $R^{30}$ are independently a hydrogen atom, an alkyl group having 1 to 4 carbon atoms, or an aryl group having 6 to 10 carbon atoms in a ring.

[Chemical Formula 27]

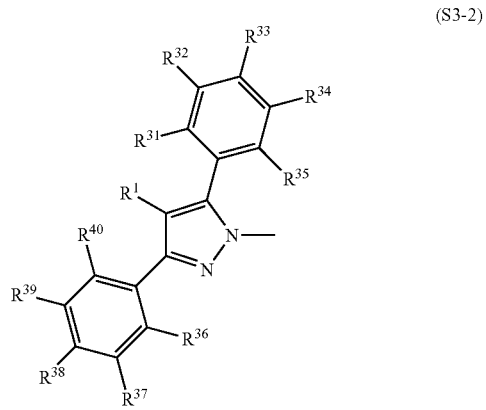

(S3-2)

In General Formula (S3-2), $R^1$ and $R^{31}$ to $R^{40}$ are independently a hydrogen atom, an alkyl group having 1 to 4 carbon atoms, or an aryl group having 6 to 10 carbon atoms in a ring.

A derivative with a heteroaromatic ring according to an embodiment of the present invention is represented by General Formula (G4).

[Chemical Formula 28]

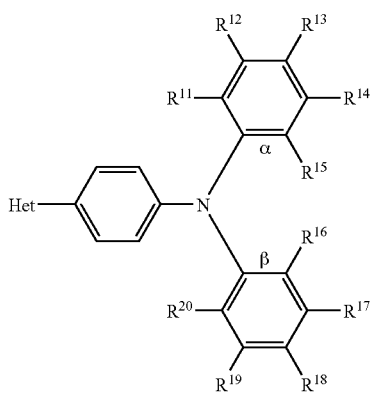

(G4)

In General Formula (G4), $R^{11}$ to $R^{20}$ are independently a hydrogen atom, an alkyl group having 1 to 4 carbon atoms, or a substituted or unsubstituted aryl group having 6 to 10 carbon atoms in a ring. When $R^{11}$ to $R^{20}$ each have a substituent, an alkyl group having 1 to 4 carbon atoms or an aryl group having 6 to 10 carbon atoms in a ring can be independently given as an example of the substituent. Note that α and β may be bonded to each other to form a carbazole skeleton. Het is a substituent represented by General Formula (S4-1) or (S4-2) below.

[Chemical Formula 29]

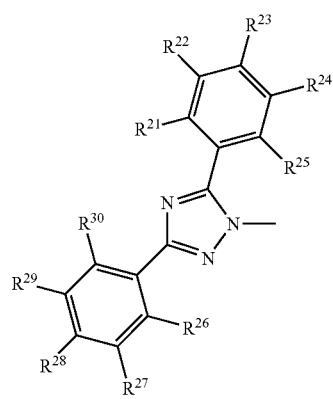

(S4-1)

In General Formula (S4-1), $R^{21}$ to $R^{30}$ are independently a hydrogen atom, an alkyl group having 1 to 4 carbon atoms, or an aryl group having 6 to 10 carbon atoms in a ring.

[Chemical Formula 30]

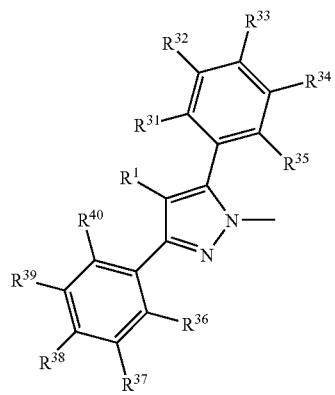

(S4-2)

In General Formula (S4-2), $R^1$ and $R^{31}$ to $R^{40}$ are independently a hydrogen atom, an alkyl group having 1 to 4 carbon atoms, or an aryl group having 6 to 10 carbon atoms in a ring.

A derivative with a heteroaromatic ring according to an embodiment of the present invention is represented by General Formula (G5).

[Chemical Formula 31]

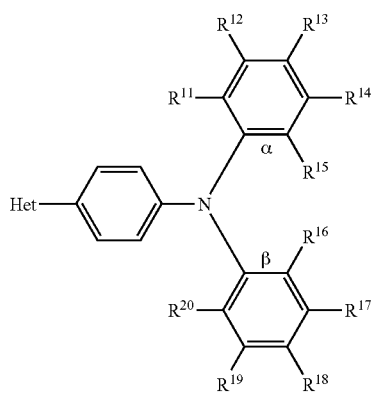

(G5)

In General Formula (G5), $R^{11}$ to $R^{20}$ are independently a hydrogen atom, an alkyl group having 1 to 4 carbon atoms, or a substituted or unsubstituted aryl group having 6 to 10 carbon atoms in a ring. When $R^{11}$ to $R^{20}$ each have a substituent, an alkyl group having 1 to 4 carbon atoms or an aryl group having 6 to 10 carbon atoms in a ring can be independently given as an example of the substituent. Note that α and β may be bonded to each other to form a carbazole skeleton. Het is a substituent represented by Structural Formula (S5-1) or General Formula (S5-2) below.

[Chemical Formula 32]

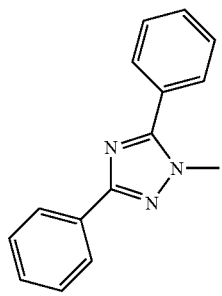

(S5-1)

-continued

[Chemical Formula 33]

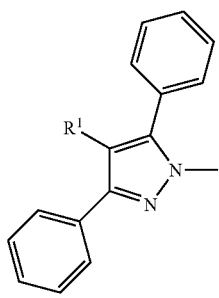
(S5-2)

In General Formula (S5-2), $R^1$ is a hydrogen atom, an alkyl group having 1 to 4 carbon atoms, or an aryl group having 6 to 10 carbon atoms in a ring.

A derivative with a heteroaromatic ring according to an embodiment of the present invention is represented by General Formula (G6).

[Chemical Formula 34]

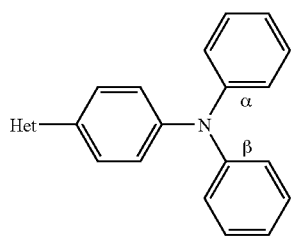
(G6)

In General Formula (G6), α and β may be bonded to each other to form a carbazole skeleton. Het is a substituent represented by Structural Formula (S6-1) or General Formula (S6-2) below.

[Chemical Formula 35]

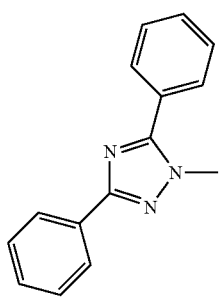
(S6-1)

[Chemical Formula 36]

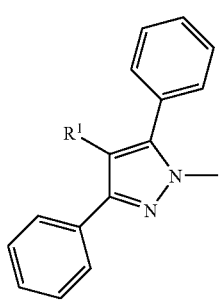
(S6-2)

In General Formula (S6-2), $R^1$ is a hydrogen atom, an alkyl group having 1 to 4 carbon atoms, or an aryl group having 6 to 10 carbon atoms in a ring.

As specific structures of $R^{11}$ to $R^{20}$ in General Formulae (G1) to (G5), for example, substituents represented by Structural Formulae (1-1) to (1-30) can be given.

[Chemical Formula 37]

H— (1-1)

H$_3$C— (1-2)

H$_2$C— / H$_3$C (1-3)

H$_2$C— / H$_3$C—CH$_2$ (1-4)

H$_3$C\\CH— /H$_3$C (1-5)

H$_2$C\\H$_2$C—CH$_3$ (1-6)

H$_3$C\\CH— /H$_2$C\\CH$_3$ (1-7)

H$_2$C— /H$_3$C—CH\\CH$_3$ (1-8)

H$_3$C\\C— /H$_3$C CH$_3$ (1-9)

(phenyl) (1-10)

H$_3$C—(phenyl)— (1-11)

H$_3$C—CH$_2$—(phenyl)— (1-12)

H$_3$C—CH$_2$—(phenyl)— (1-13)

H$_3$C\\CH—(phenyl)— /H$_3$C (1-14)

-continued
(1-15) 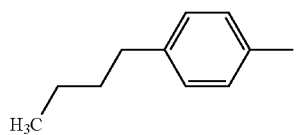
(1-16) 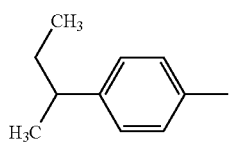
(1-17) 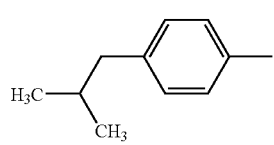
(1-18) 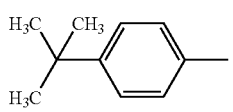
(1-19) 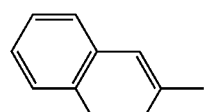
(1-20) 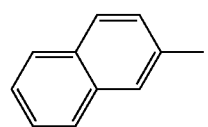
(1-21) 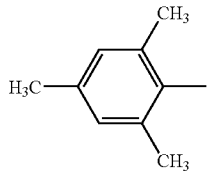
(1-22) 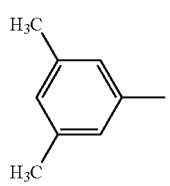
(1-23) 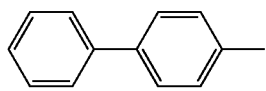
(1-24) 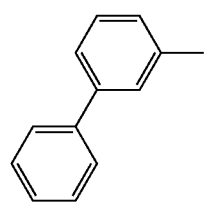
-continued
(1-25) 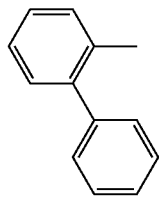
(1-26) 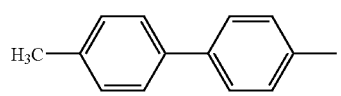
(1-27) 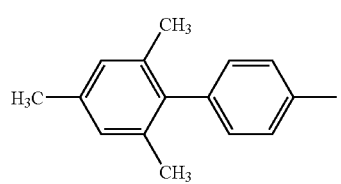
(1-28) 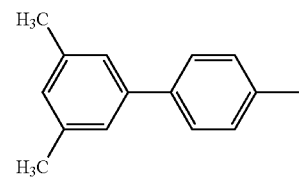
(1-29) 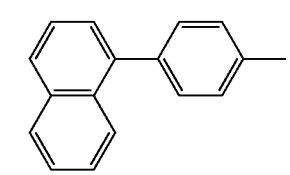
(1-30) 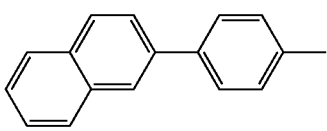
As specific structures of J in General Formulae (G1) and (G2), for example, substituents represented by Structural Formulae (2-1) to (2-20) can be given.
[Chemical Formula 38]
(2-1) 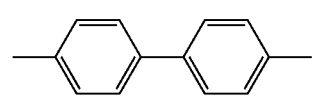
(2-2) 
(2-3) 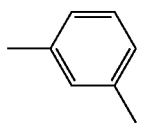
(2-4) 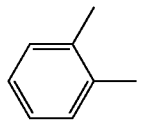

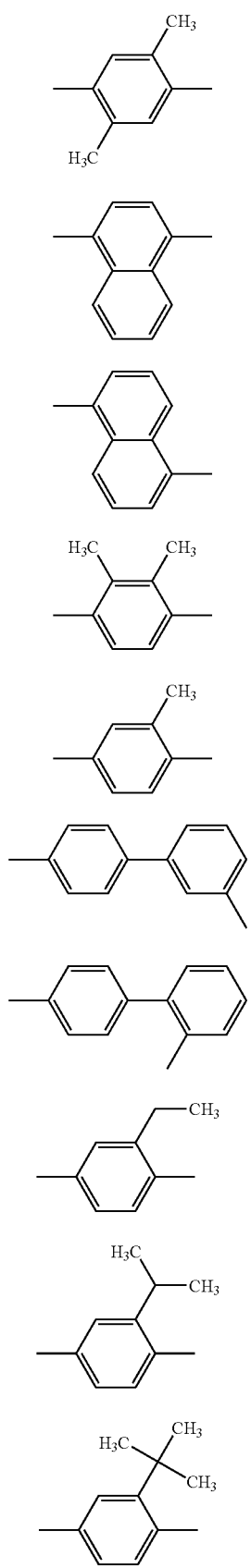
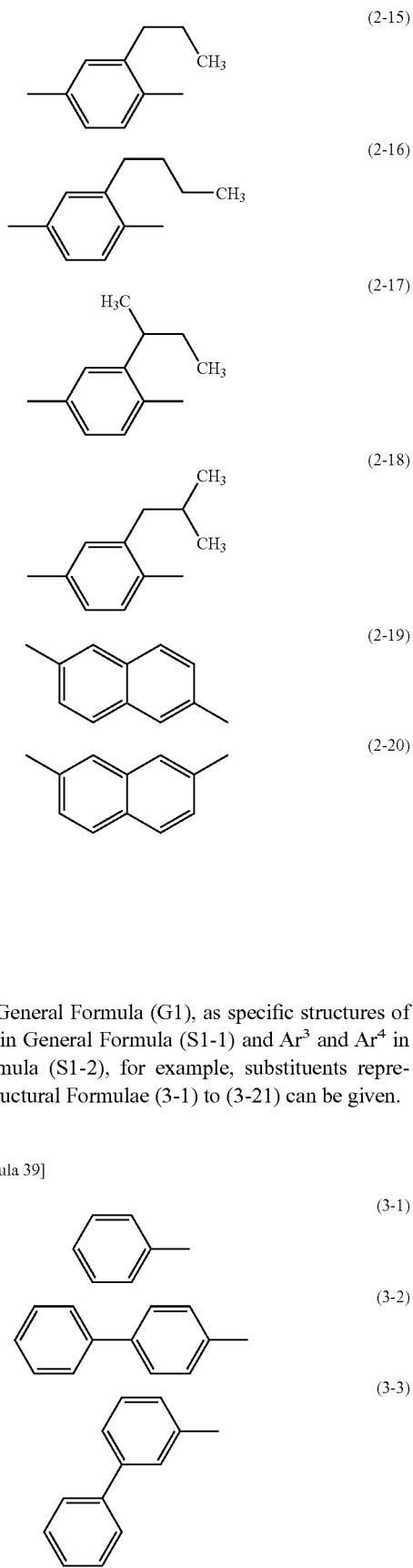
In Het of General Formula (G1), as specific structures of Ar¹ and Ar² in General Formula (S1-1) and Ar³ and Ar⁴ in General Formula (S1-2), for example, substituents represented by Structural Formulae (3-1) to (3-21) can be given.
[Chemical Formula 39]

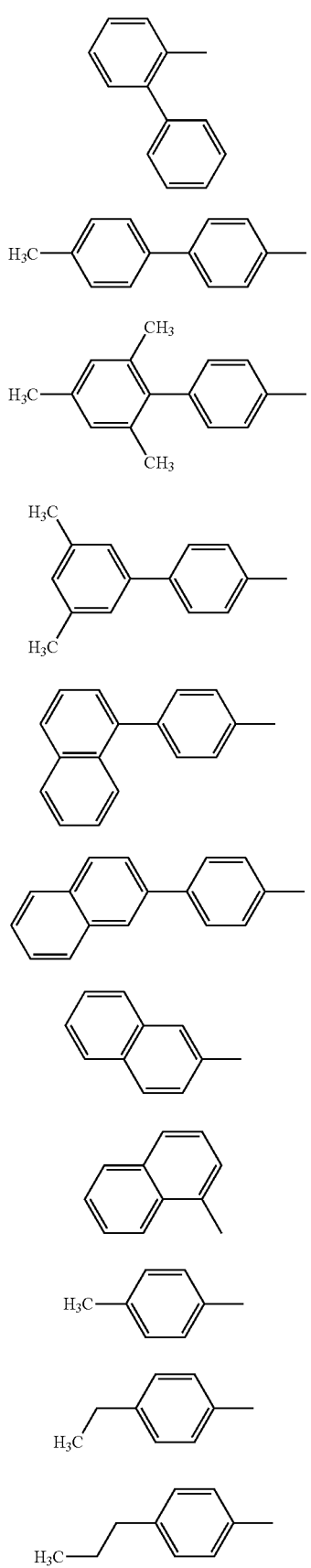
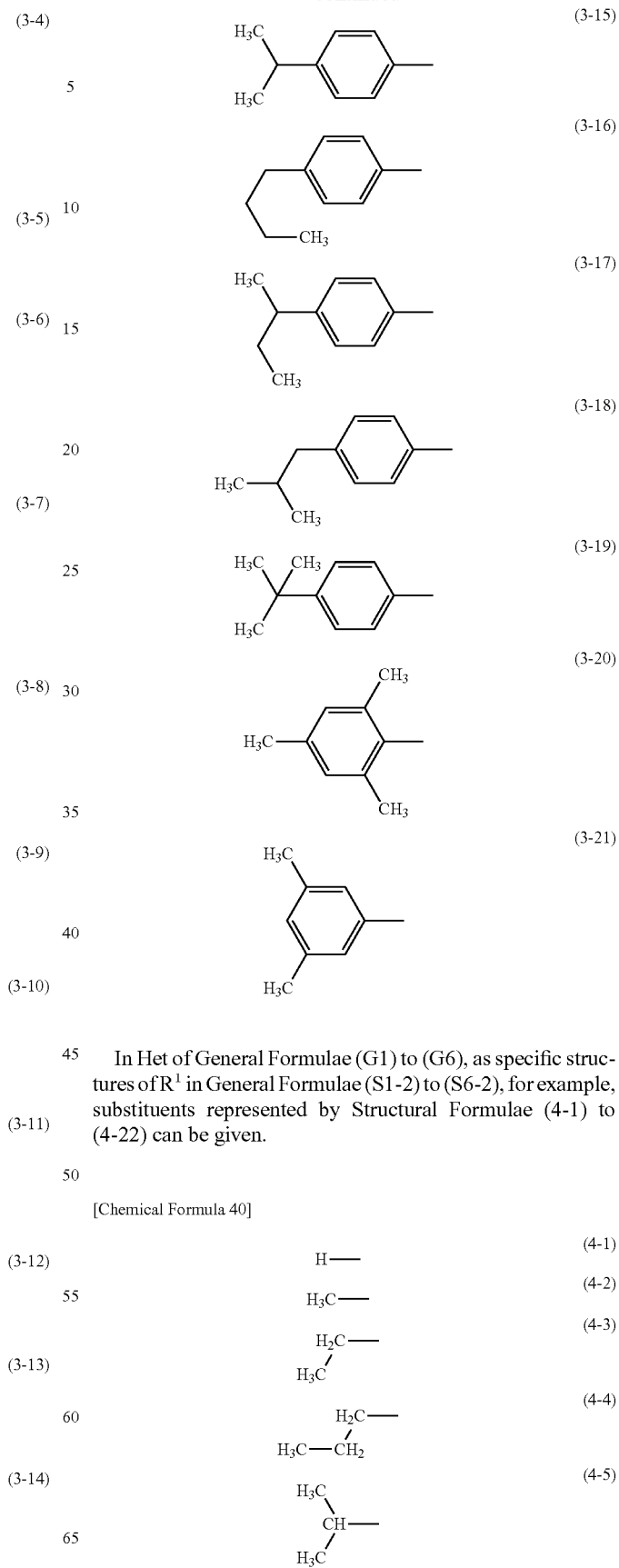
In Het of General Formulae (G1) to (G6), as specific structures of $R^1$ in General Formulae (S1-2) to (S6-2), for example, substituents represented by Structural Formulae (4-1) to (4-22) can be given.
[Chemical Formula 40]
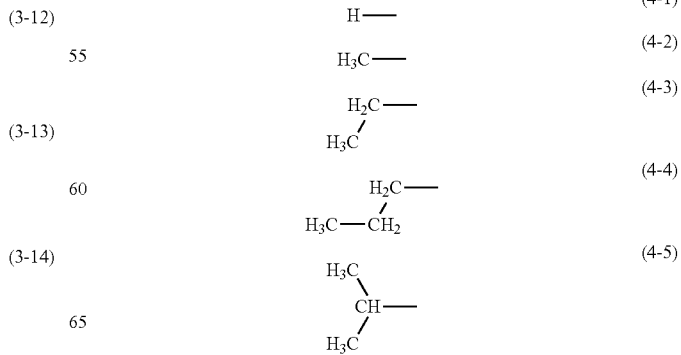

(4-6) 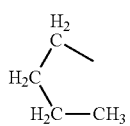
(4-7) 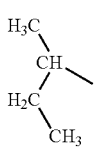
(4-8) 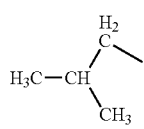
(4-9) 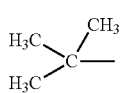
(4-10) 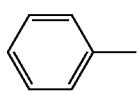
(4-11) 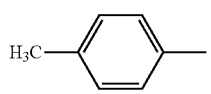
(4-12) 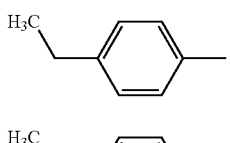
(4-13) 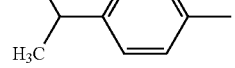
(4-14) 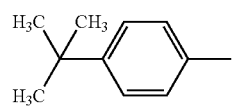
(4-15) 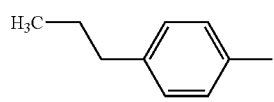
(4-16) 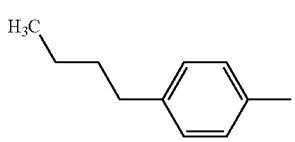
(4-17) 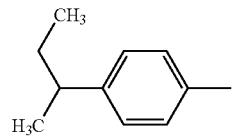
(4-18) 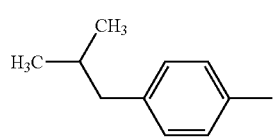
(4-19) 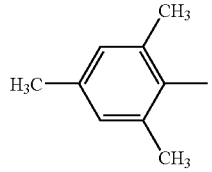
(4-20) 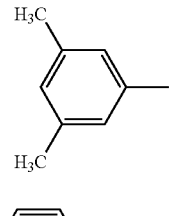
(4-21) 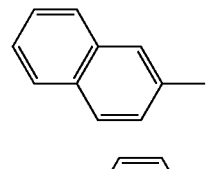
(4-22) 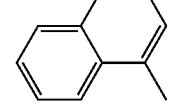
In Het of General Formulae (G2) to (G5), as specific structures of $R^{21}$ to $R^{40}$ in General Formulae (S2-1) to (S4-1) and (S2-2) to (S4-2), for example, substituents represented by Structural Formulae (5-1) to (5-22) can be given.
[Chemical Formula 41]
(5-1) 
(5-2) 
(5-3) 
(5-4) 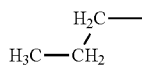
(5-5) 
(5-6) 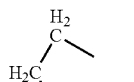
(5-7) 

-continued
(5-8) 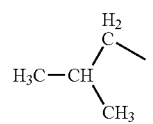
(5-9) 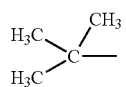
(5-10) 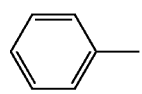
(5-11) 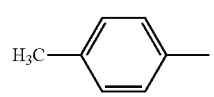
(5-12) 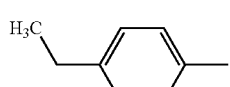
(5-13) 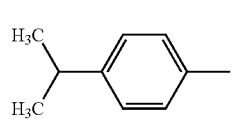
(5-14) 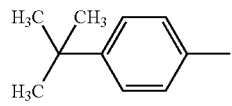
(5-14) 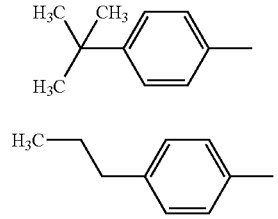
(5-15) 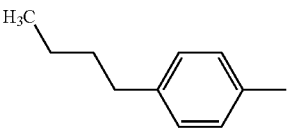
(5-16) 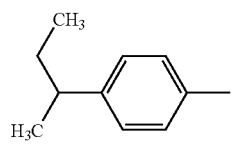
(5-17) 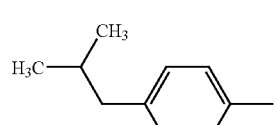
(5-18) 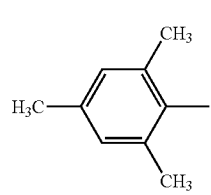
(5-19)
-continued
(5-20) 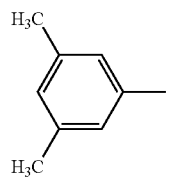
(5-21) 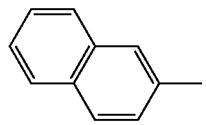
(5-22) 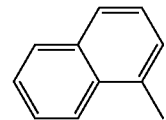
As specific examples of a derivative with a heteroaromatic ring of the present invention represented by General Formula (G1), derivatives with a heteroaromatic ring represented by Structural Formulae (100) to (275) can be given. However, the present invention is not limited to these.
[Chemical Formula 42]
(100) 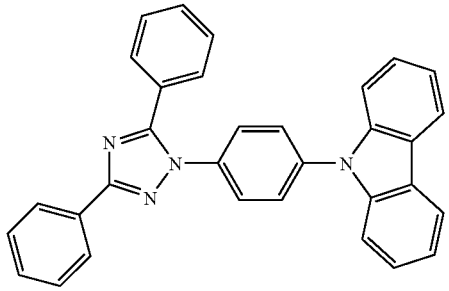
(101) 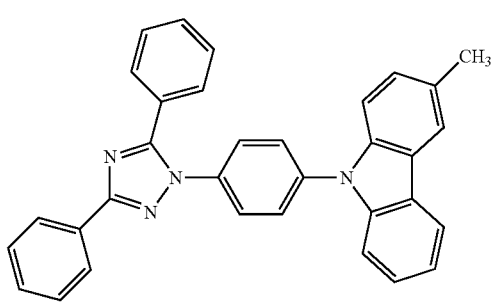
(102) 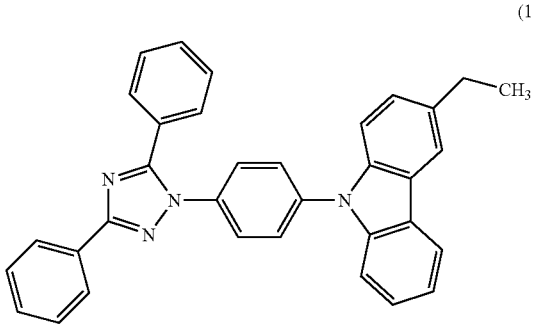

(103)
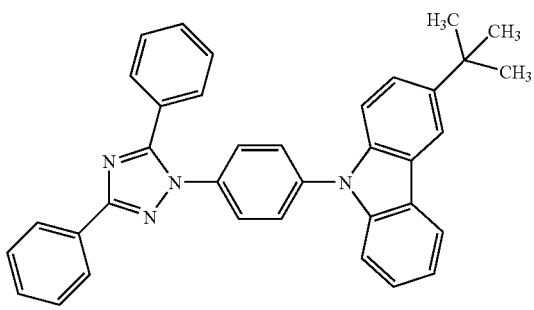
(104)
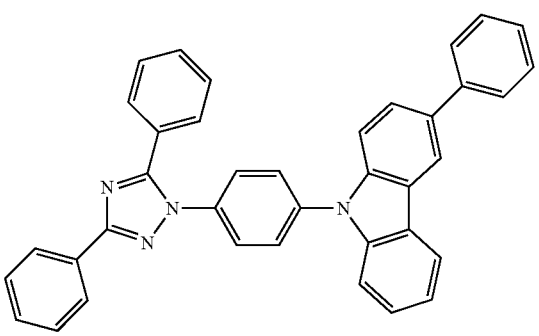
(105)
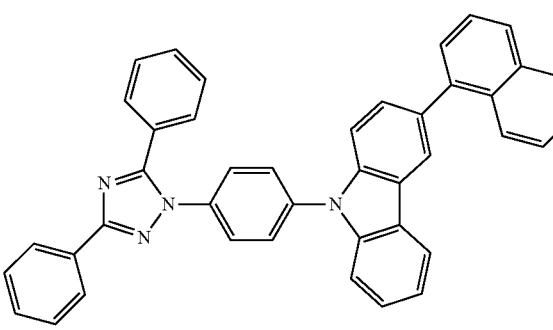
[Chemical Formula 43]
(106)
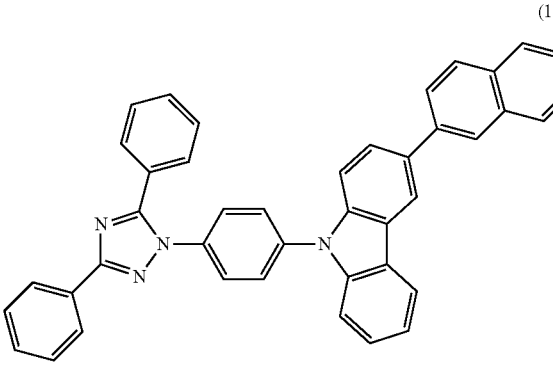
(107)
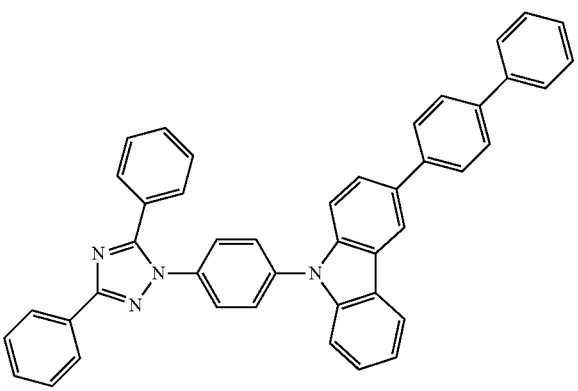
(108)
(109)
(110)
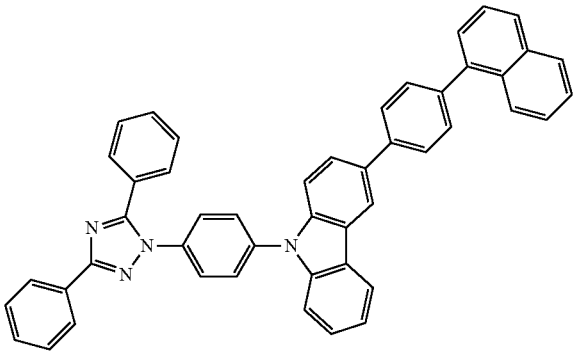

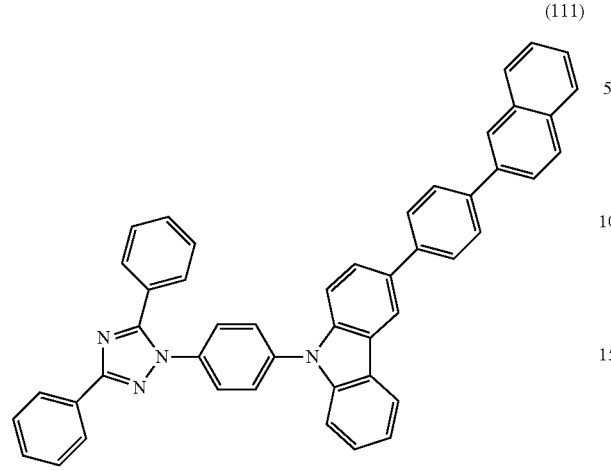
(111)
[Chemical Formula 44]
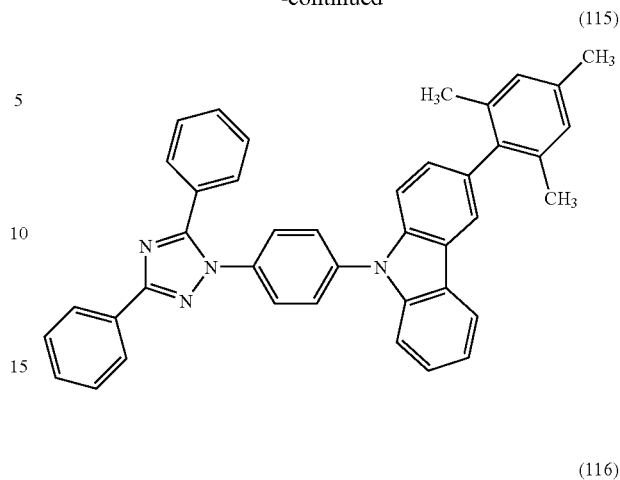
(115)
(112)
(116)
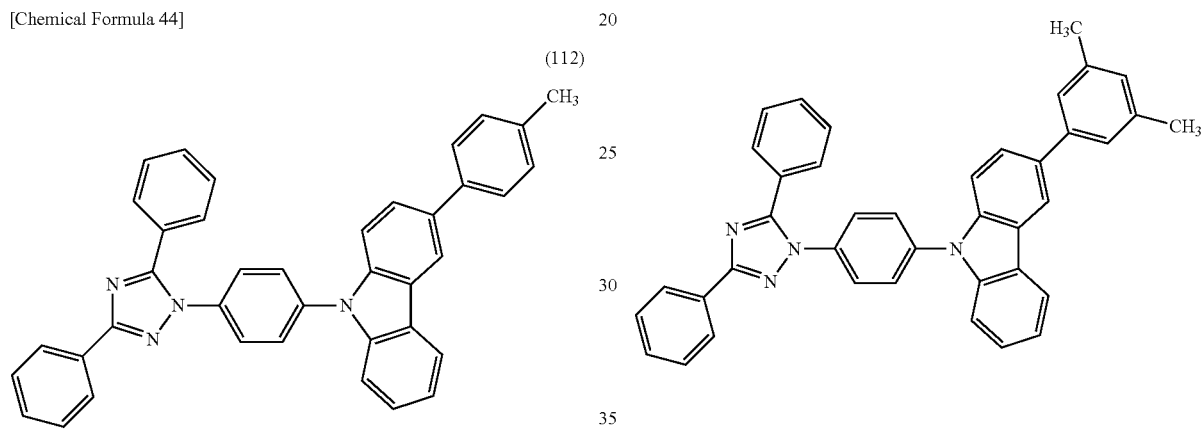
(113)
(117)
[Chemical Formula 45]
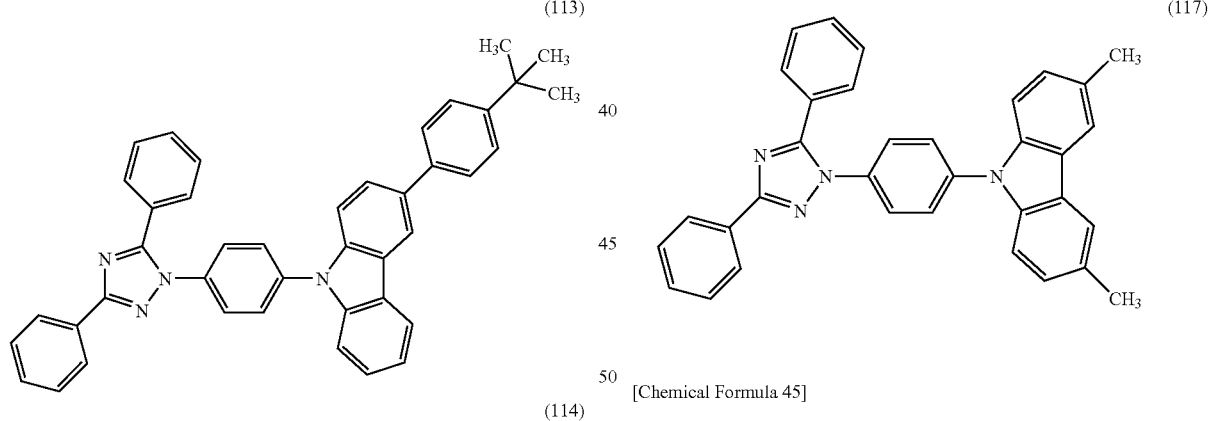
(114)
(118)
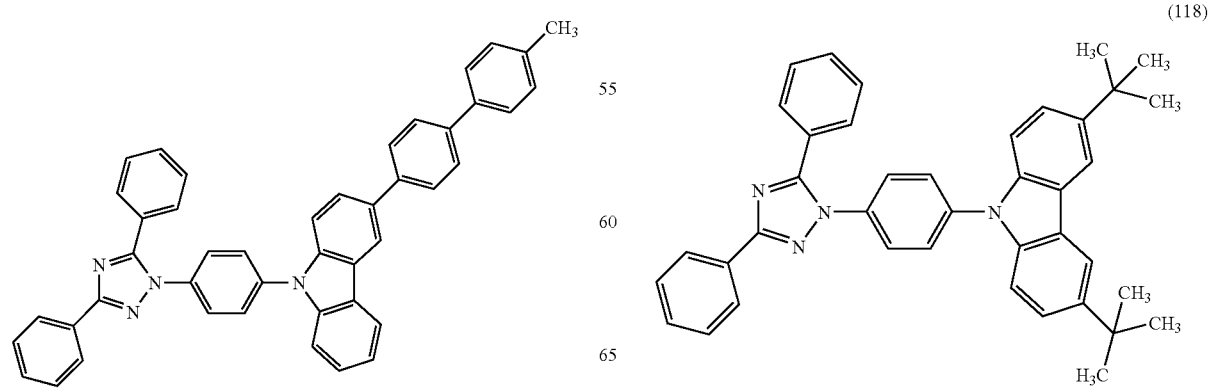

(119)
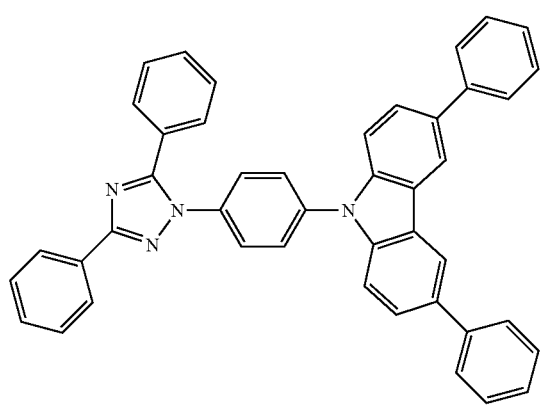
(120)
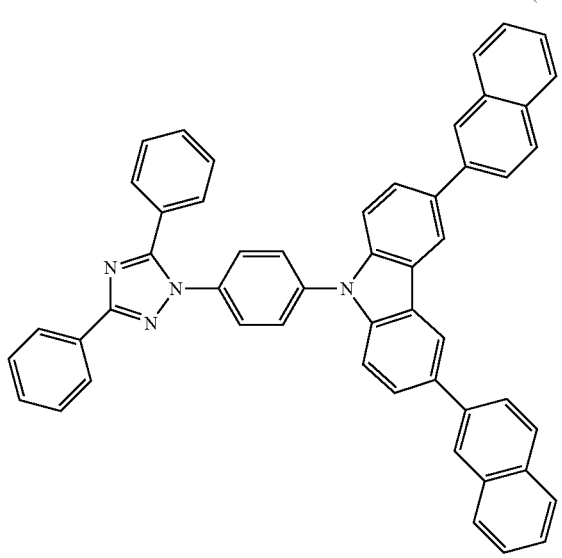
(121)
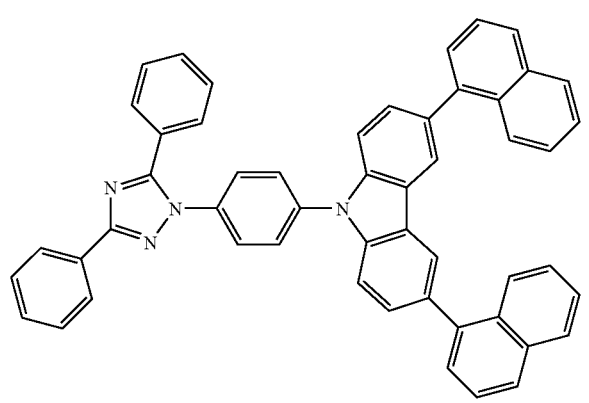
(122)
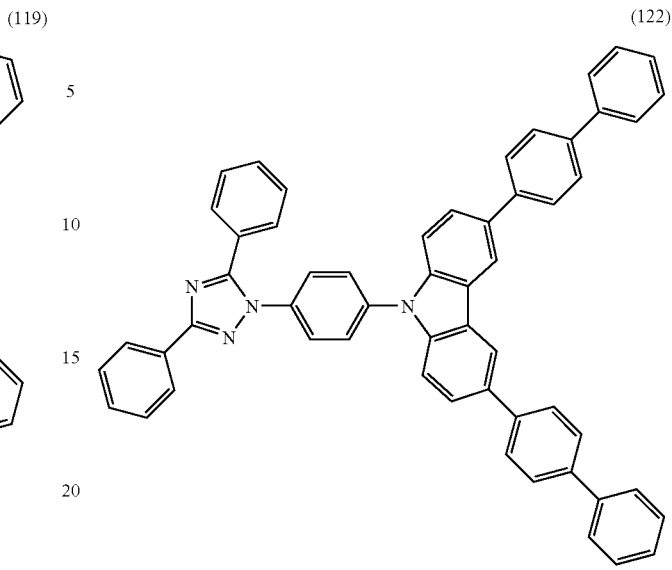
(123)
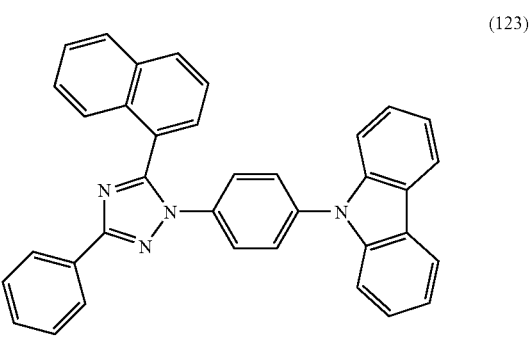
[Chemical Formula 46]
(124)
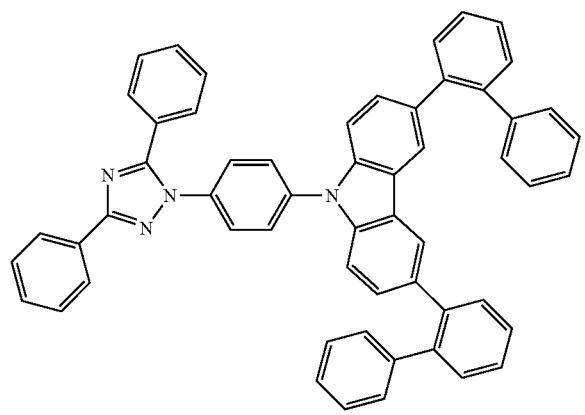

-continued
(125)
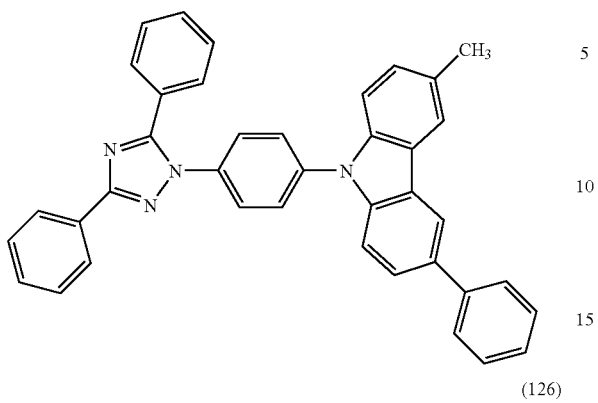
(129)
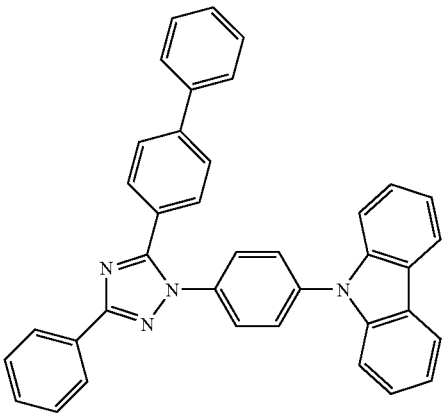
[Chemical Formula 47]
(126)
(130)
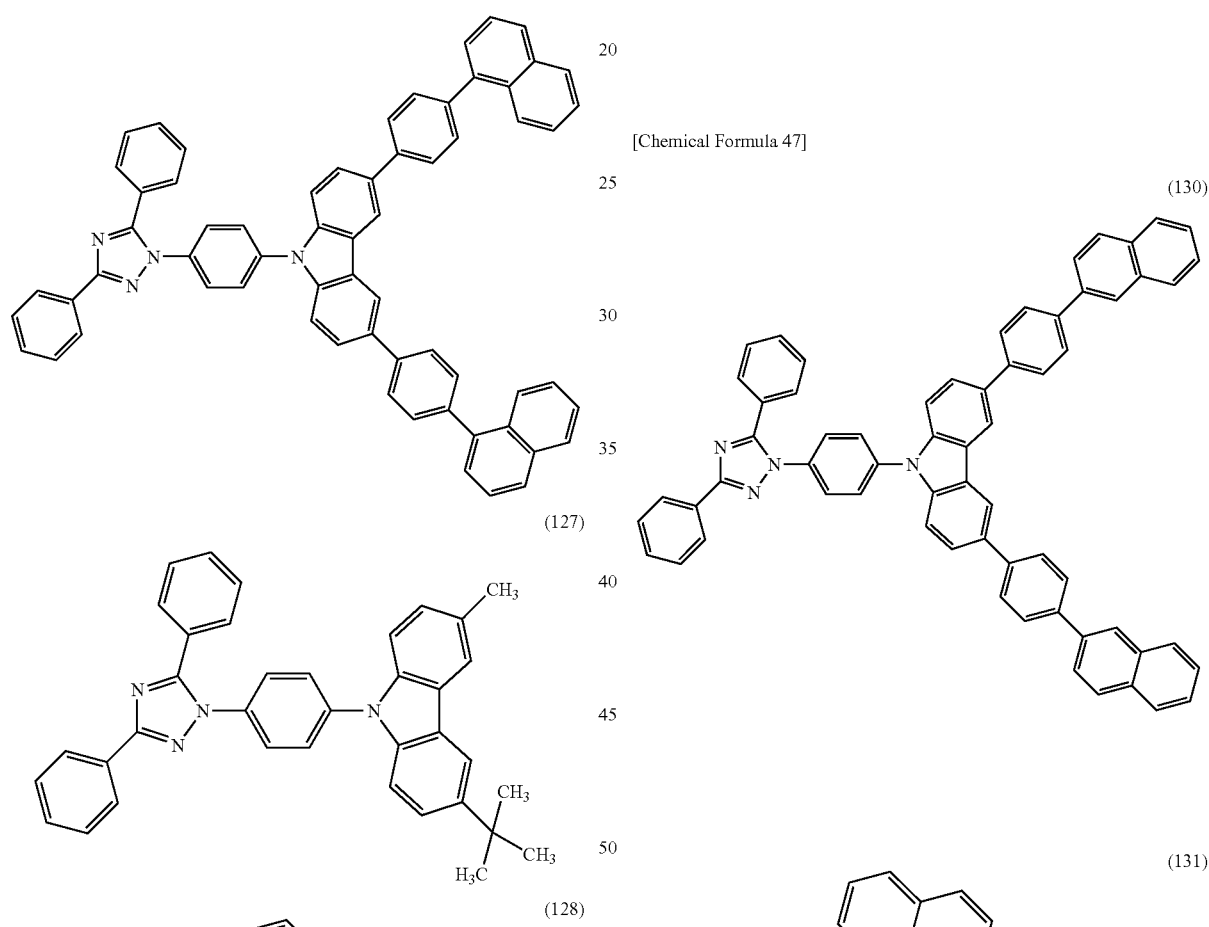
(127)
(128)
(131)
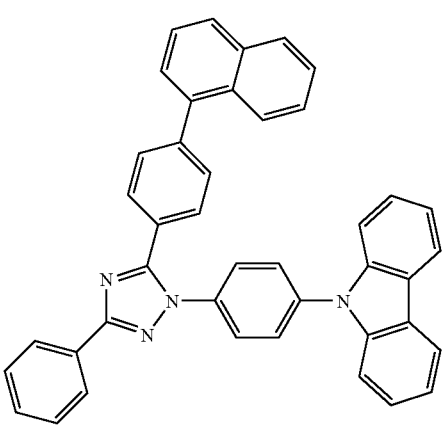

(132)
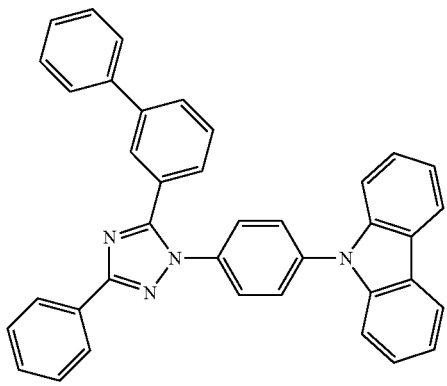
(133)
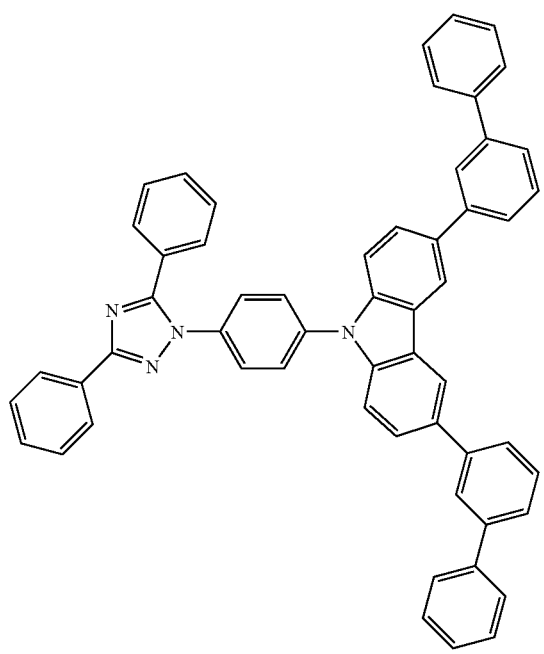
(134)
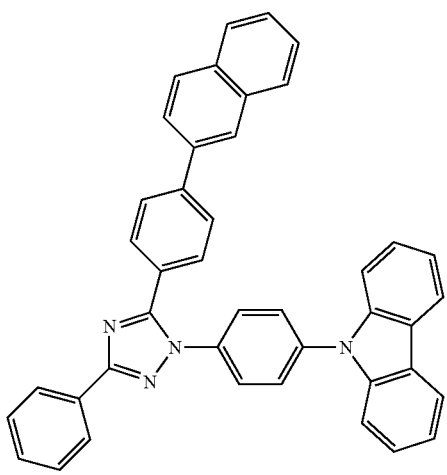
(135)
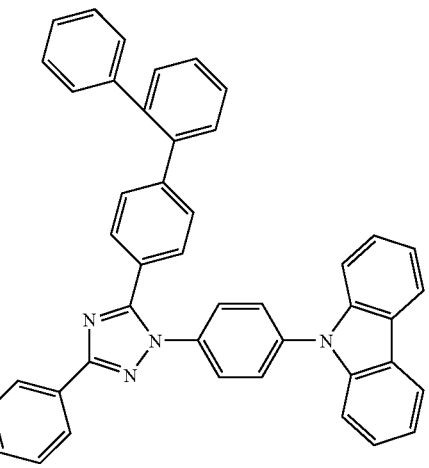
[Chemical Formula 48]
(136)
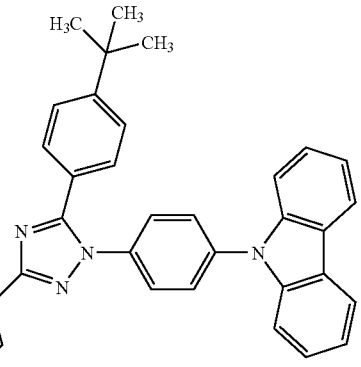
(137)
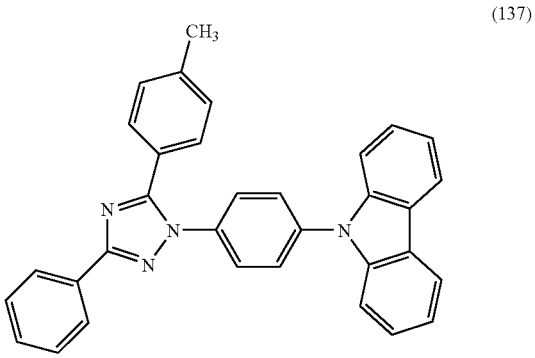

(138)
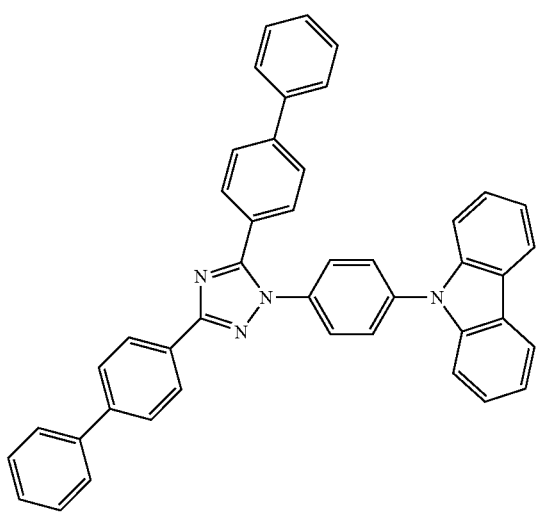
(139)
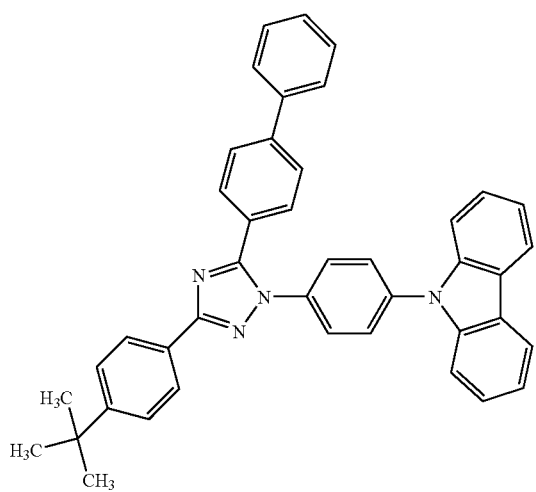
(140)
(141)
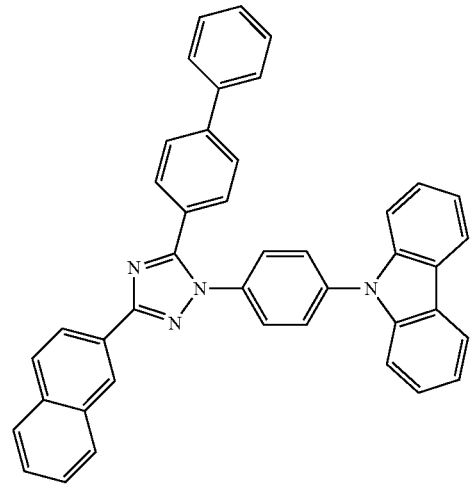
[Chemical Formula 49]
(142)
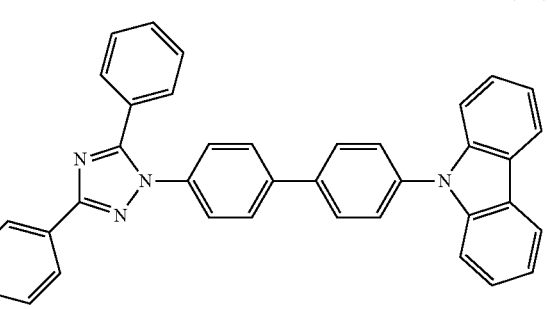
(143)
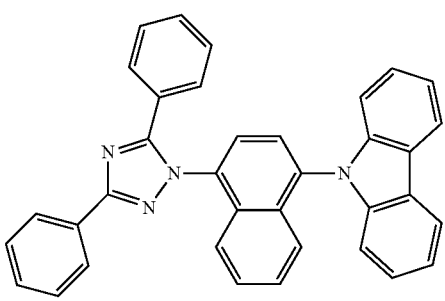
(144)
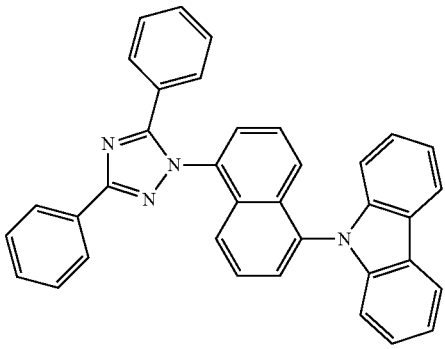

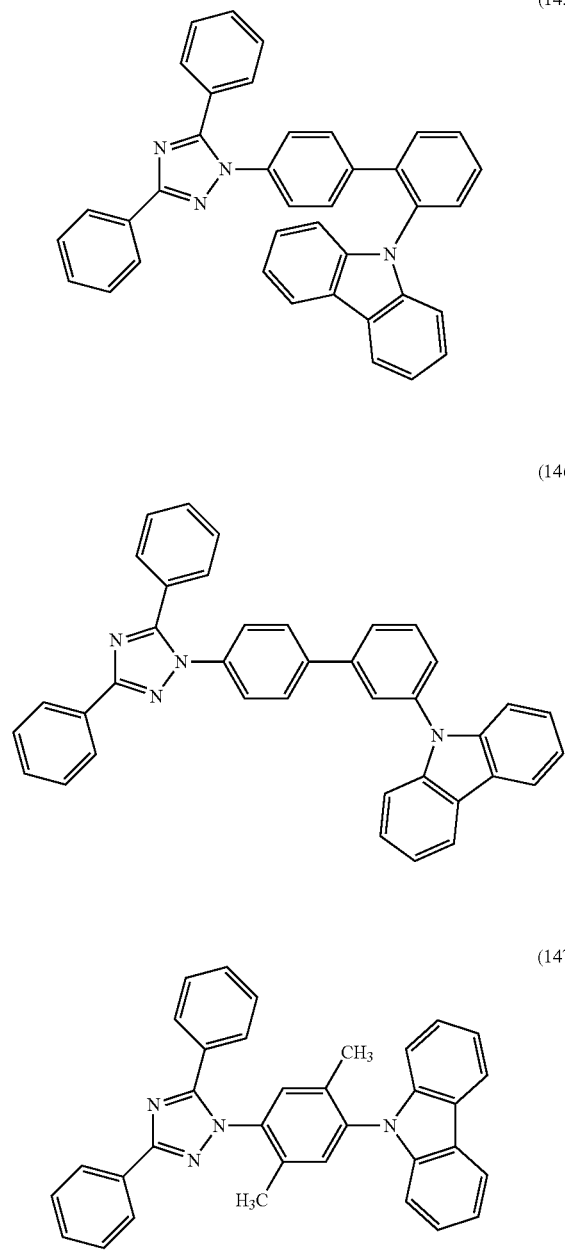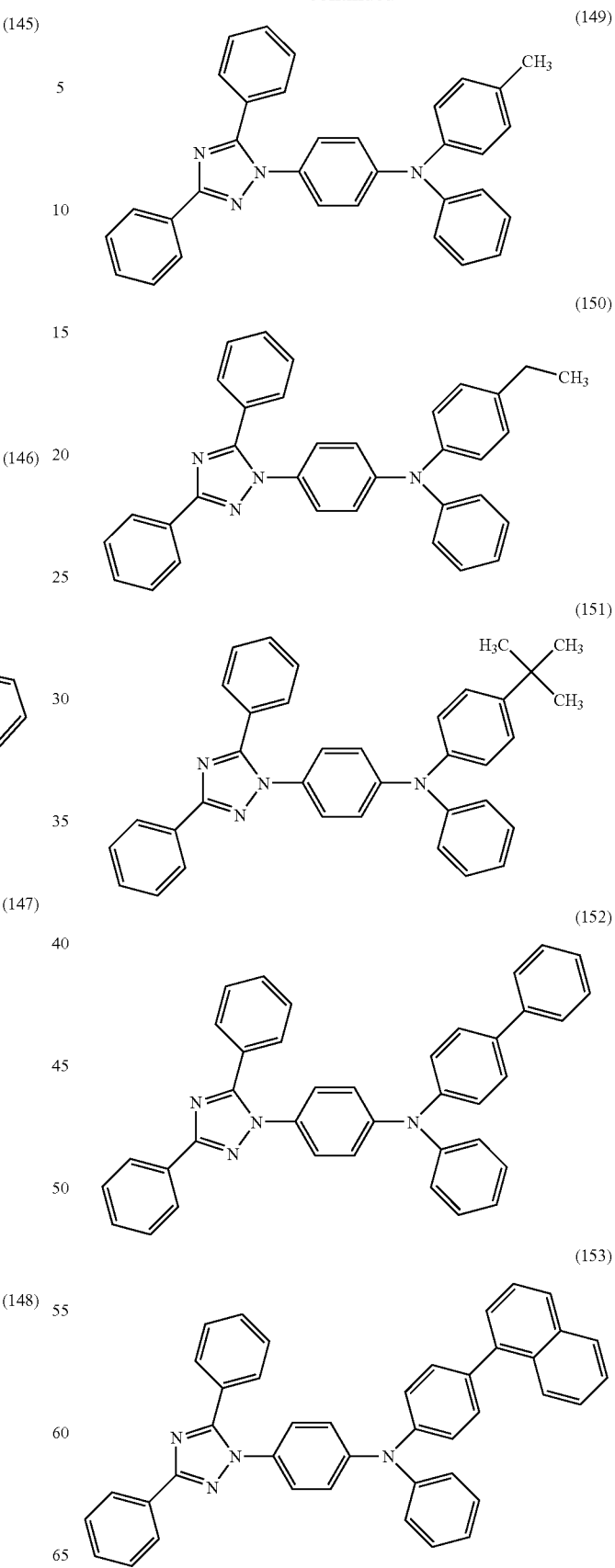

[Chemical Formula 51]
(154)
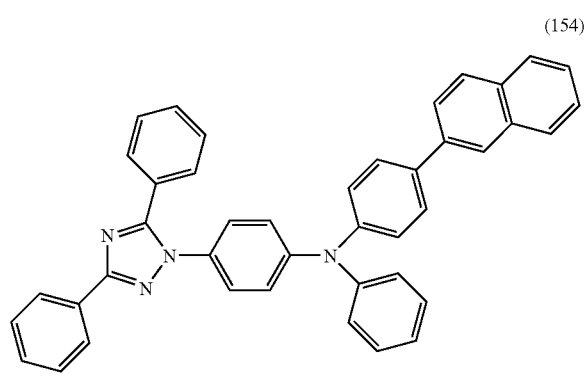
(155)
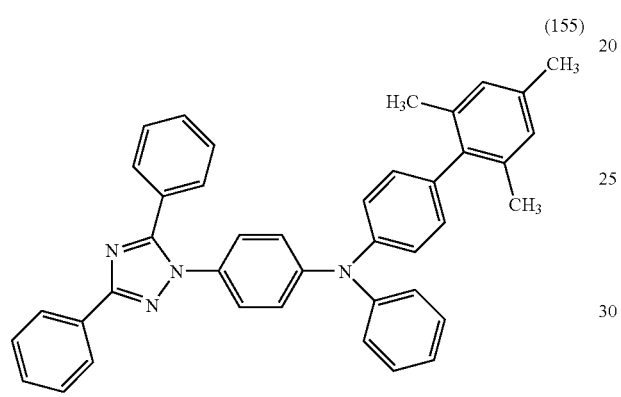
(156)
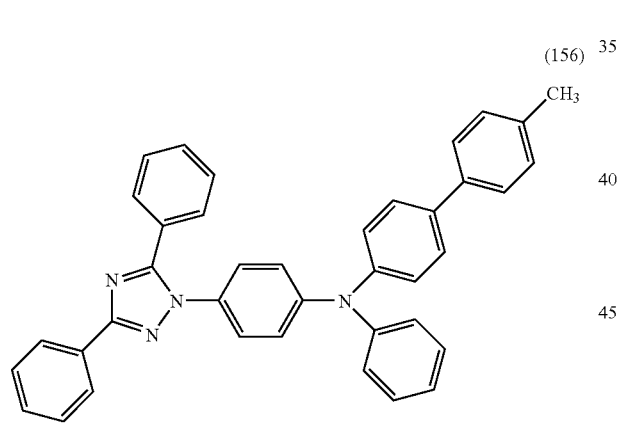
(157)
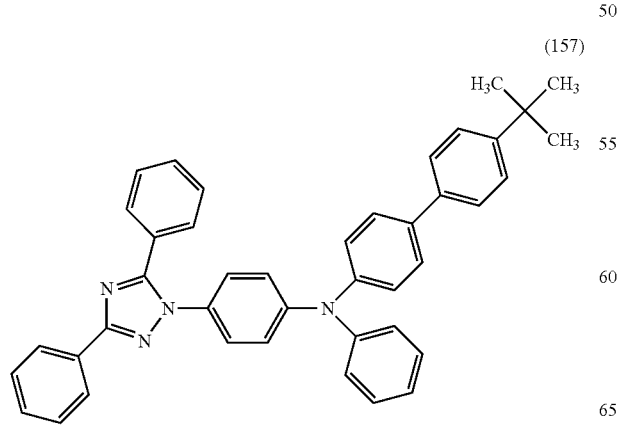
(158)
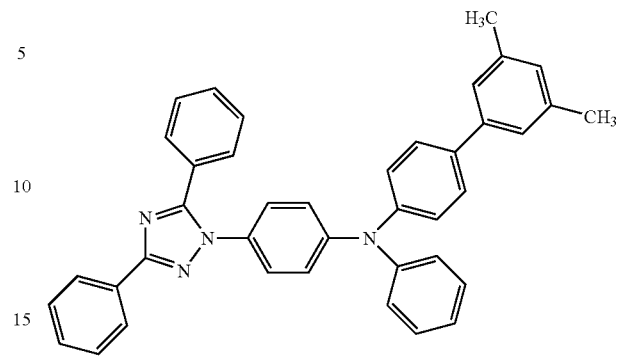
(159)
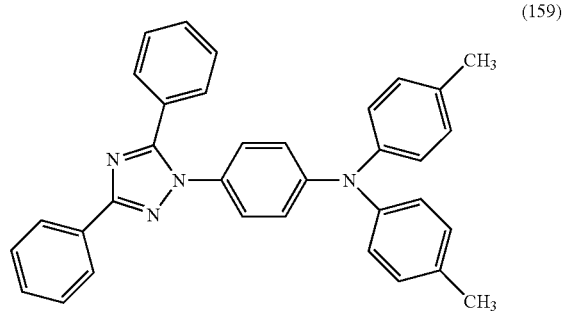
[Chemical Formula 52]
(160)
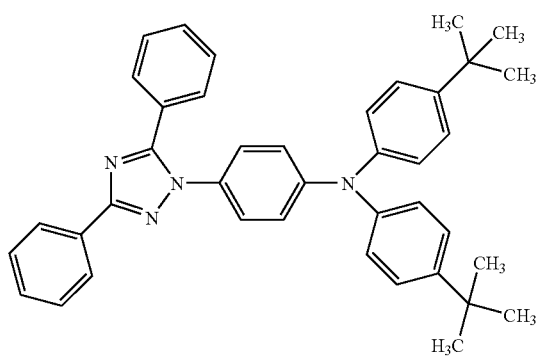
(161)
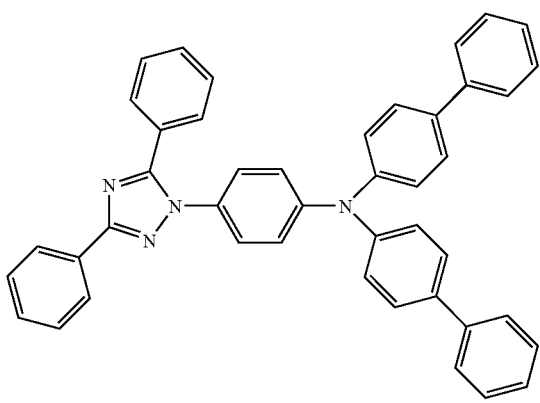

(162)
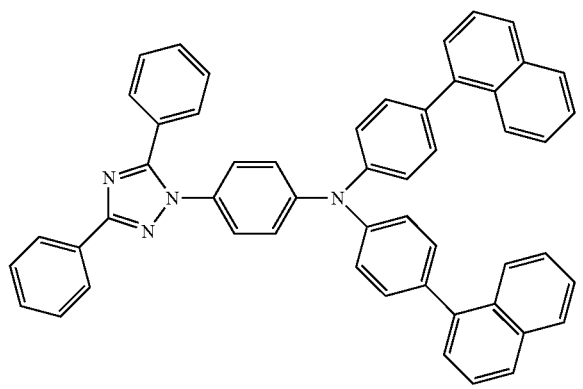
(163)
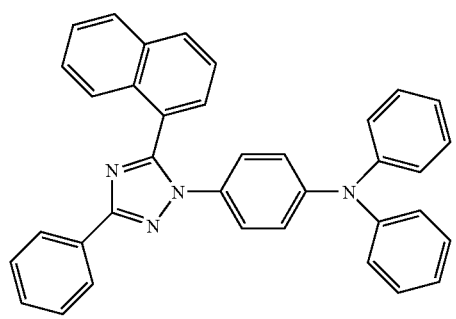
(164)
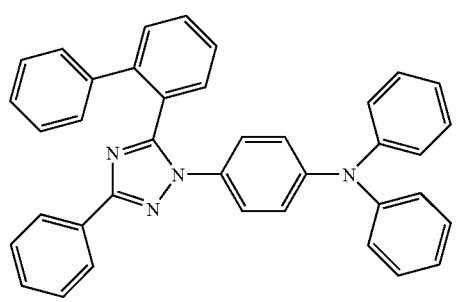
(165)
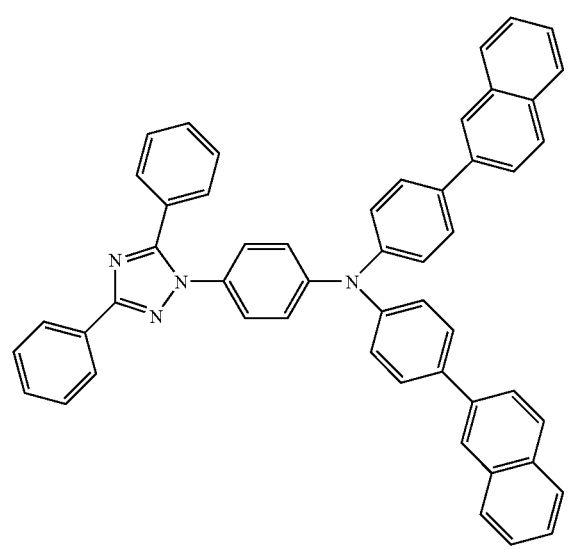
[Chemical Formula 53]
(166)
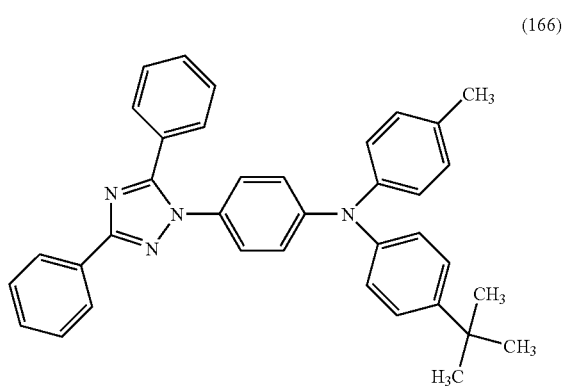
(167)
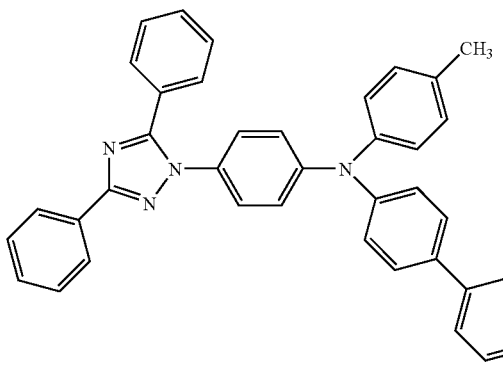
(168)
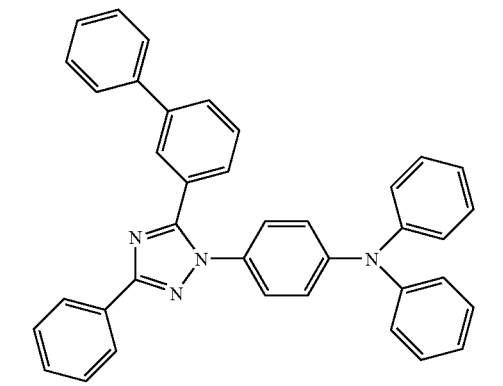
(169)
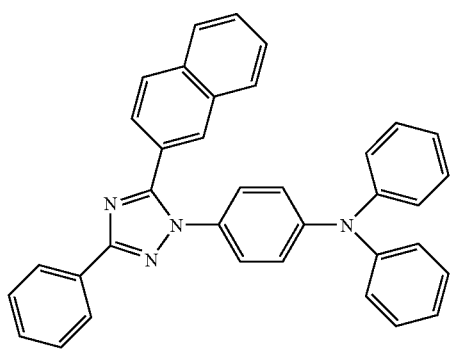

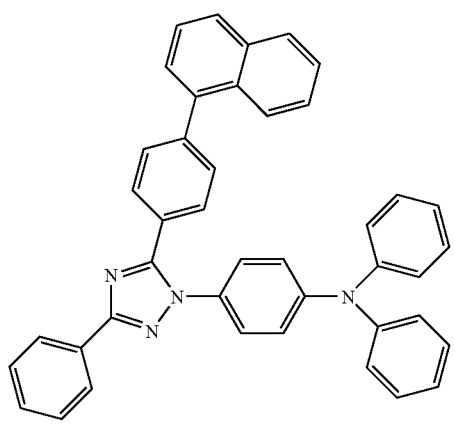
(170)
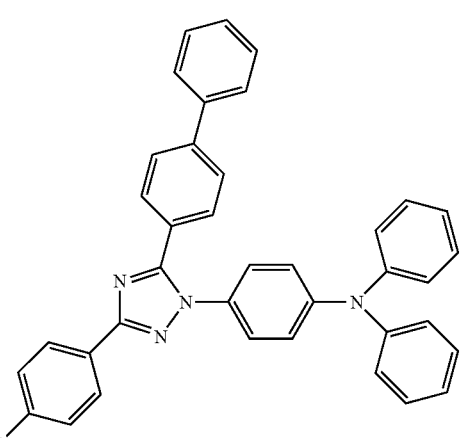
(173)
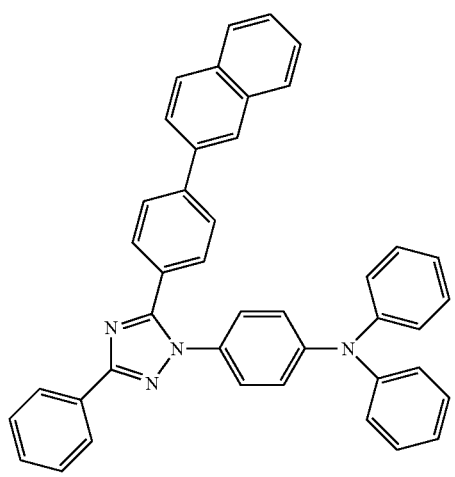
(171)
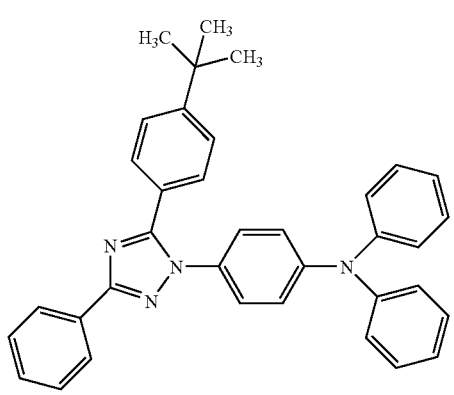
(174)
[Chemical Formula 54]
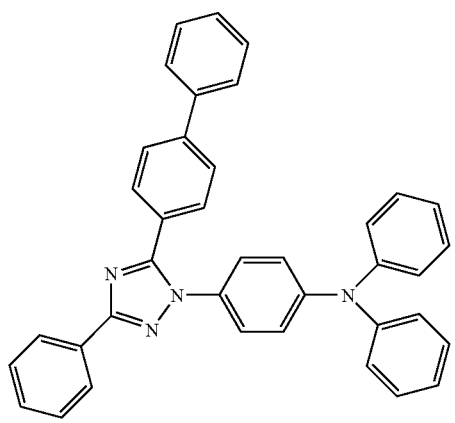
(172)
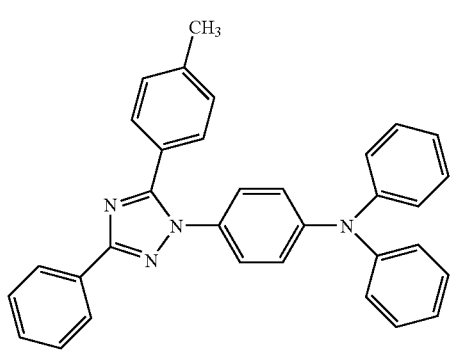
(175)

(176)
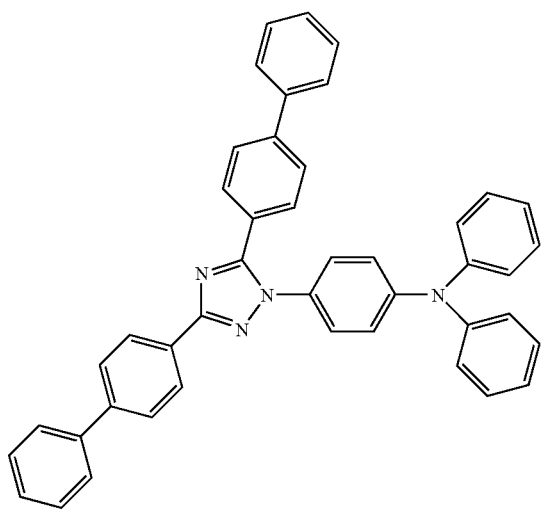
(177)
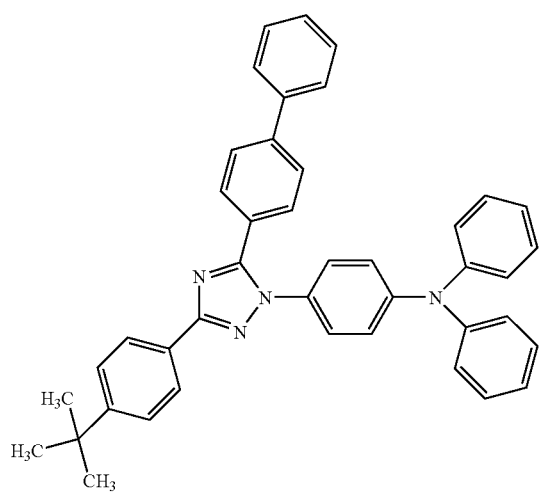
[Chemical Formula 55]
(178)
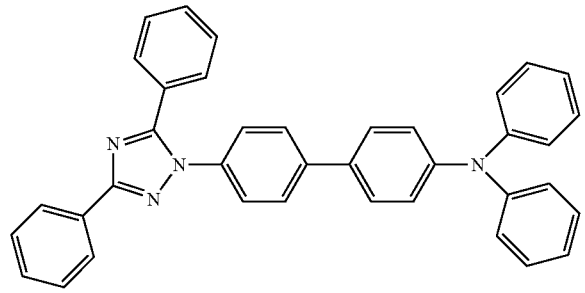
(179)
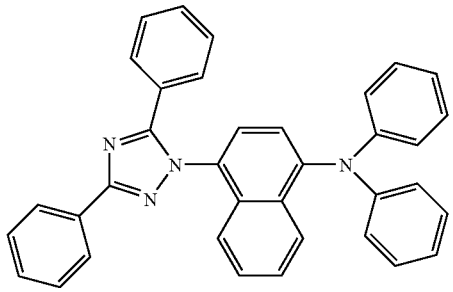
(180)
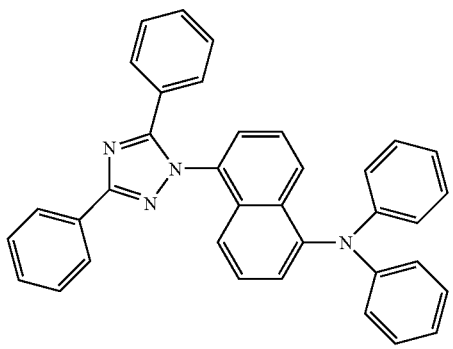
(181)
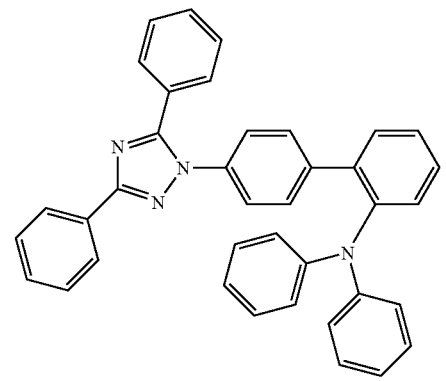
(182)
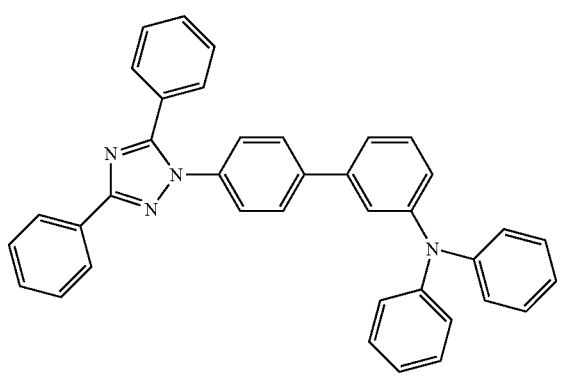

(183)
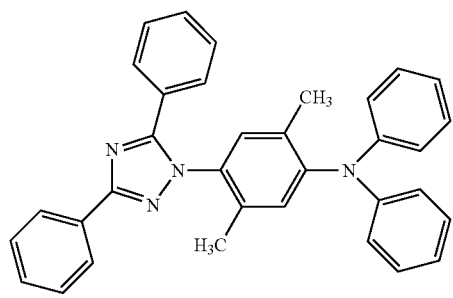
[Chemical Formula 56]
(184)
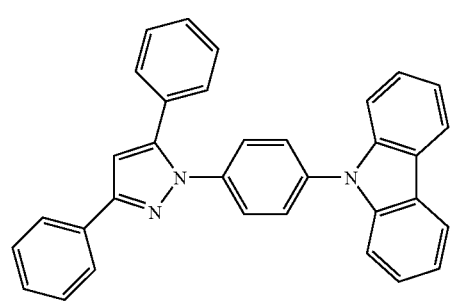
(185)
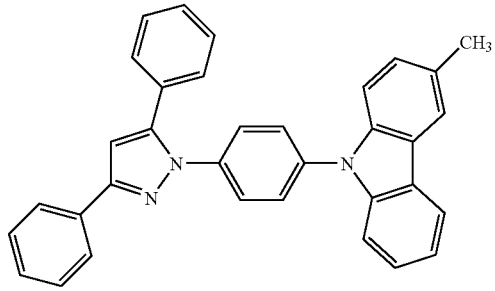
(186)
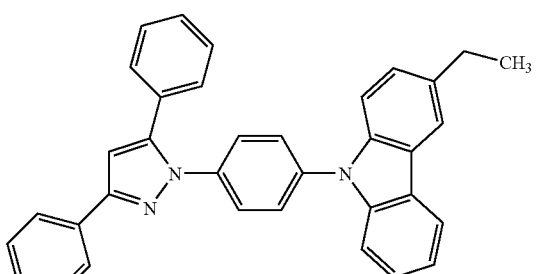
(187)
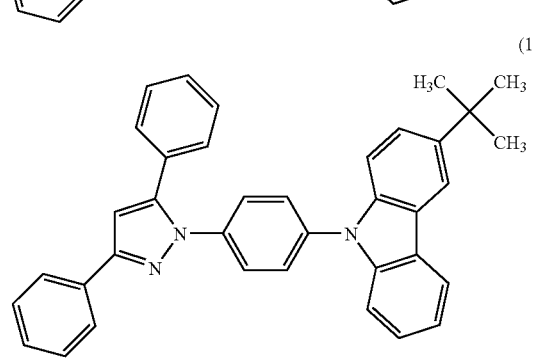
(188)
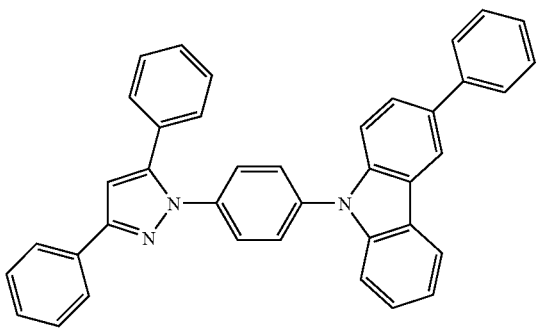
(189)
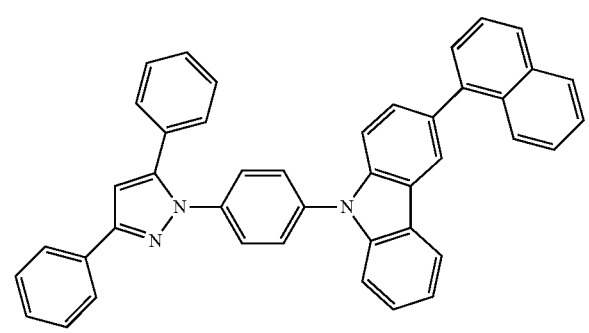
[Chemical Formula 57]
(190)
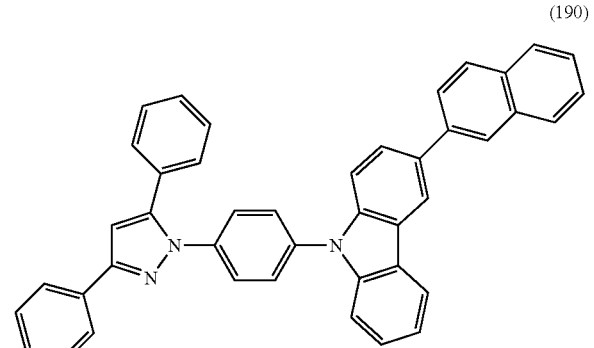
(191)
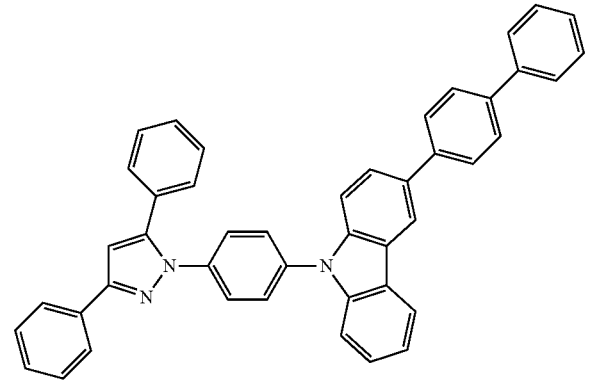

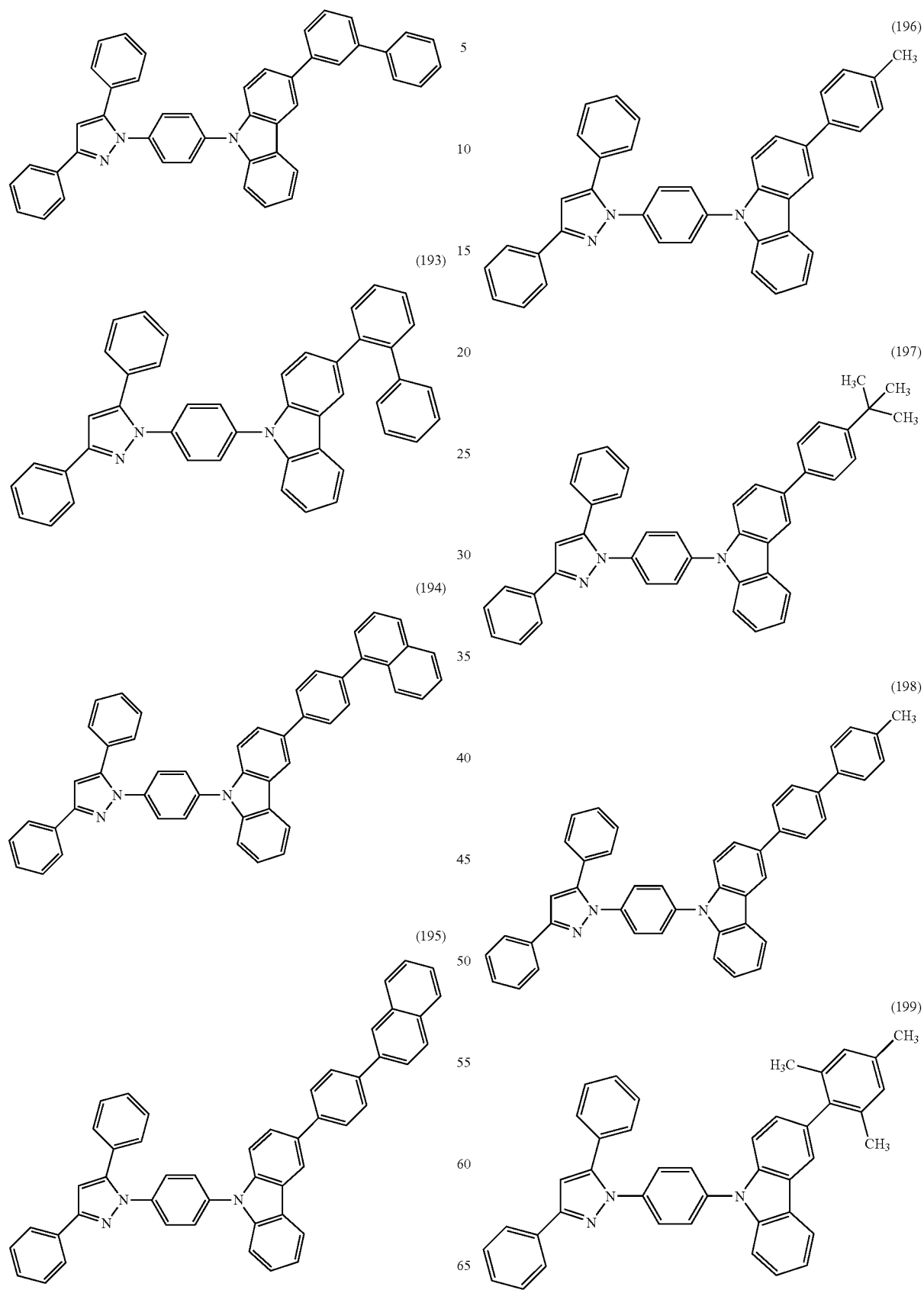

(200)
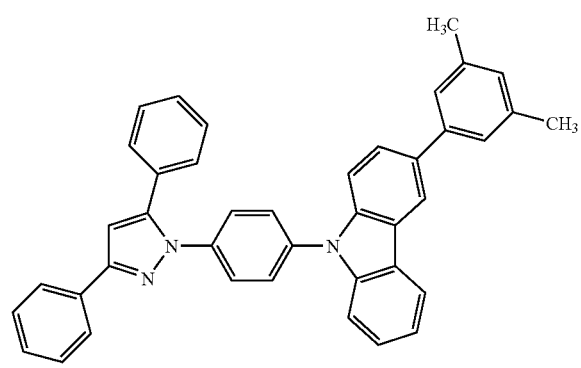
(201)
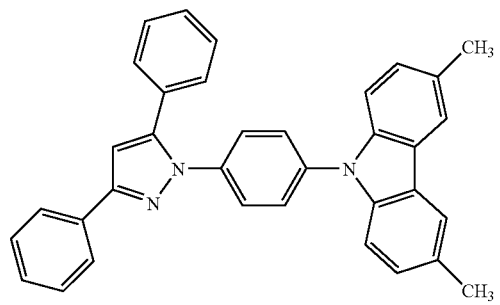
[Chemical Formula 59]
(202)
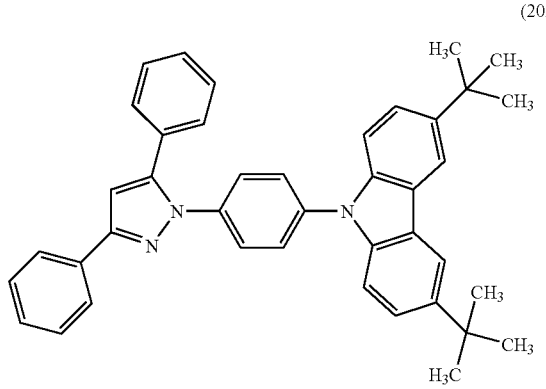
(203)
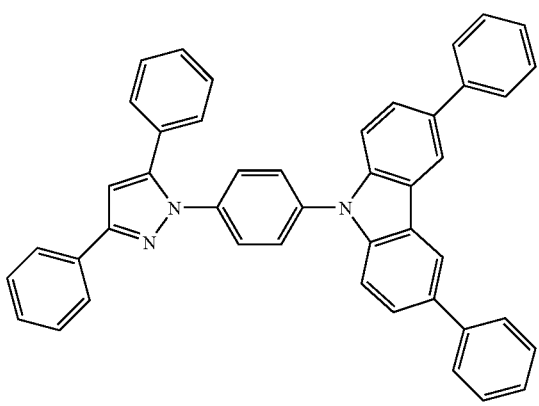
(204)
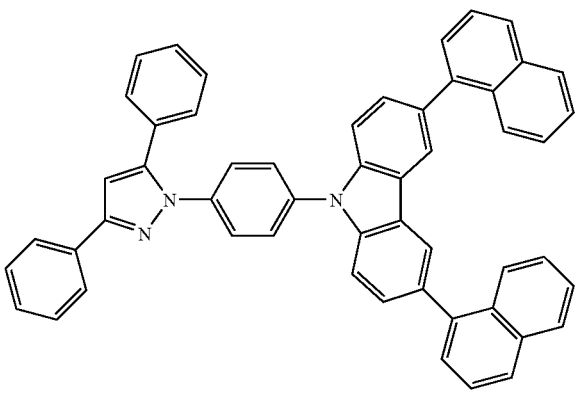
(205)
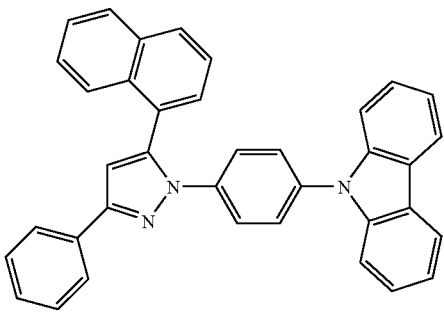
(206)
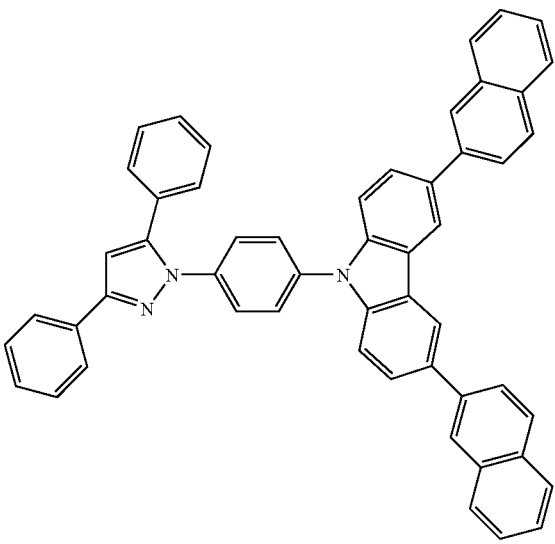
(207)
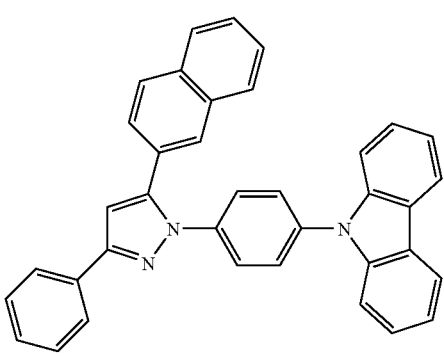

-continued
(208)
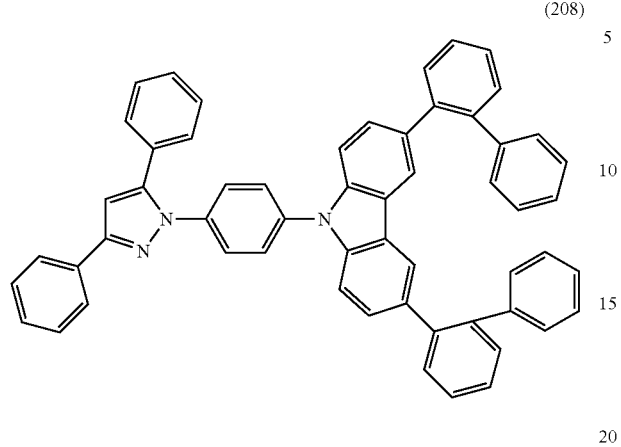
(209)
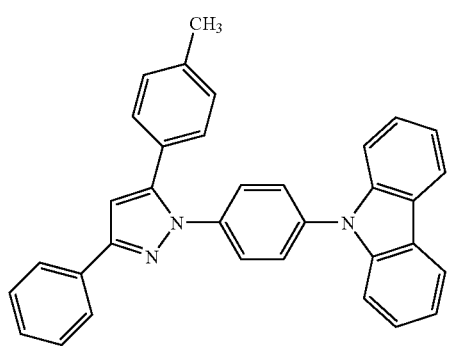
(210)
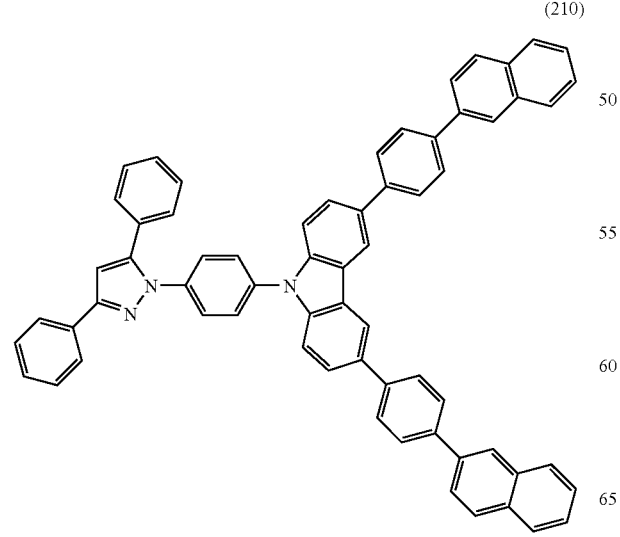
-continued
(211)
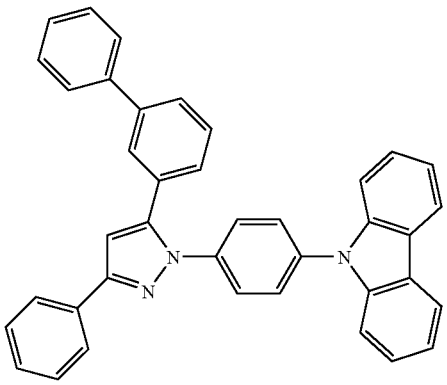
(212)
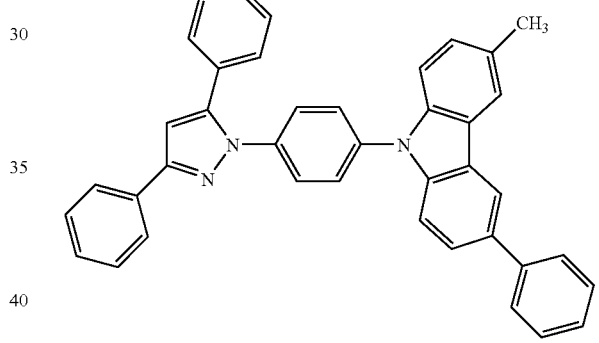
(213)
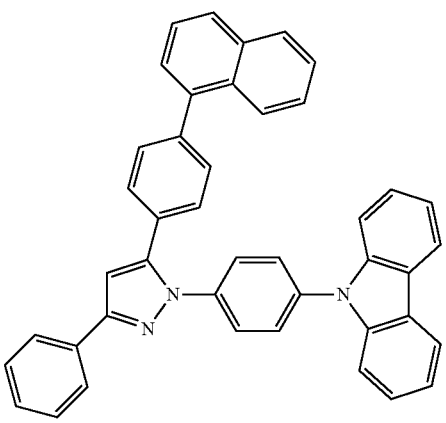

[Chemical Formula 61]
(214)
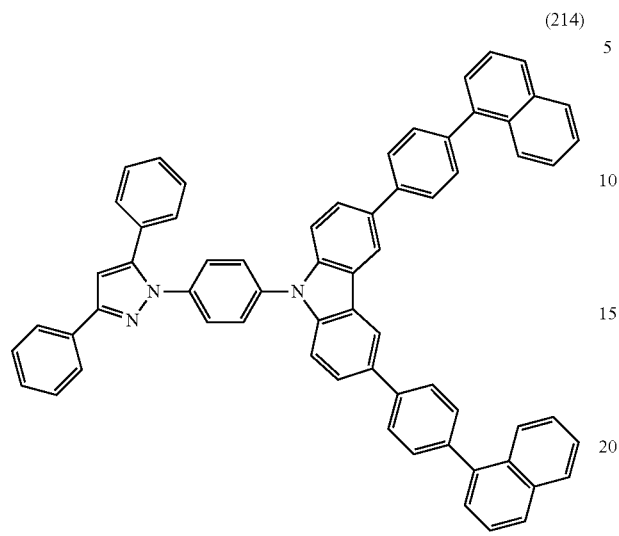
(215)
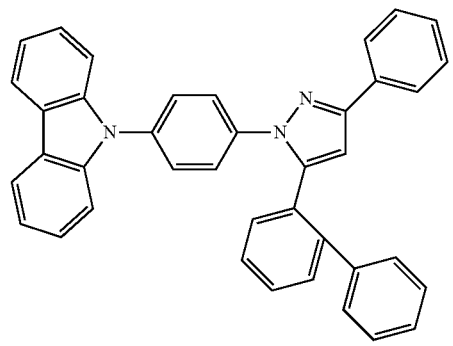
(216)
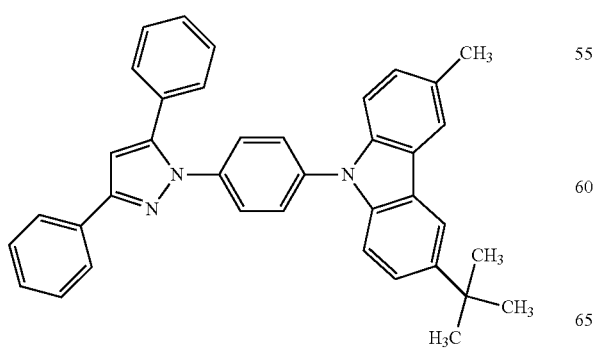
(217)
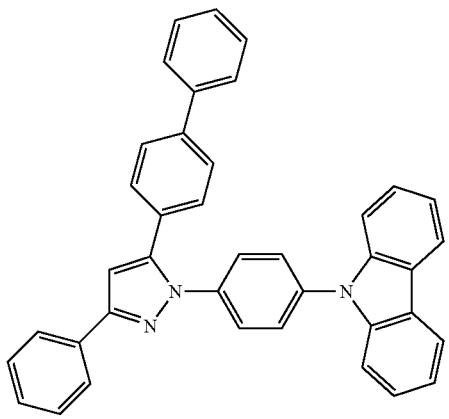
(218)
(219)
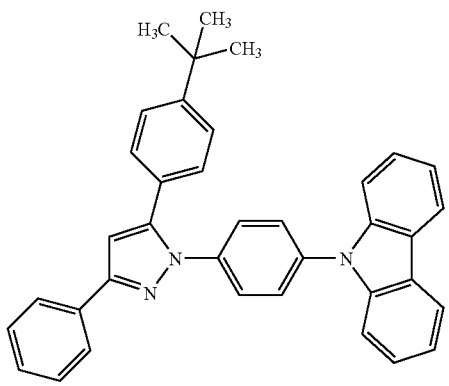

[Chemical Formula 62]
(220) 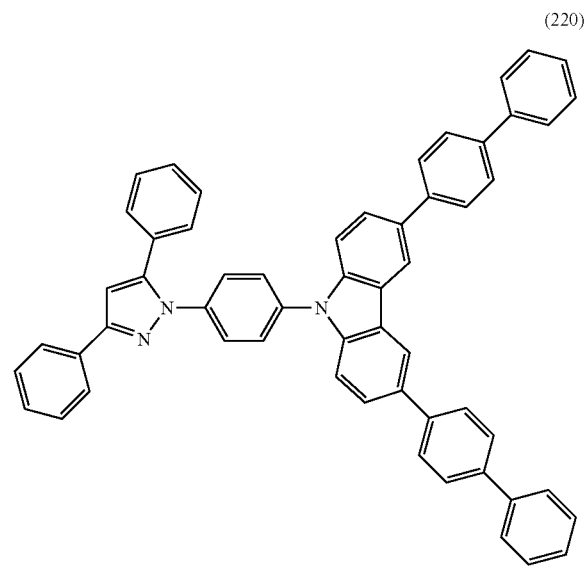
(221) 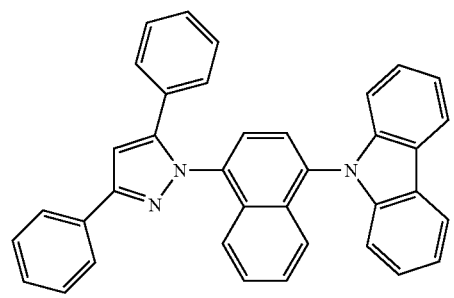
(222) 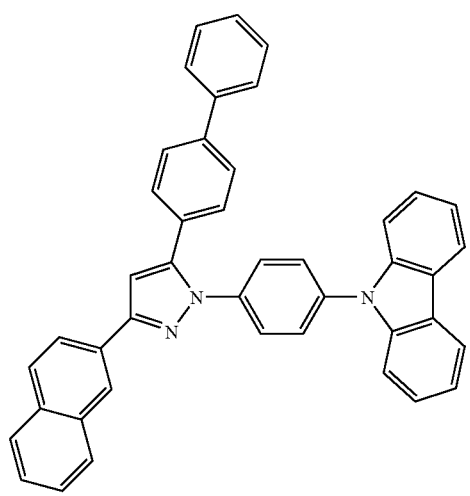
(223) 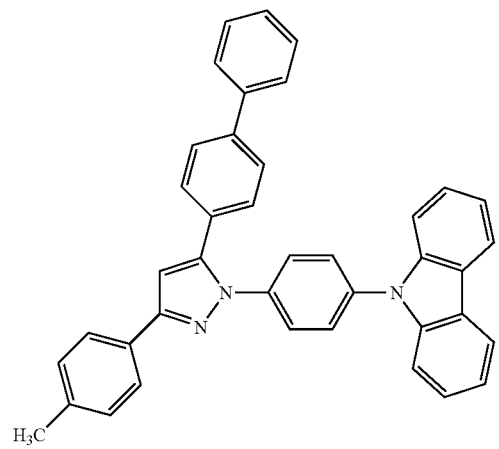
(224) 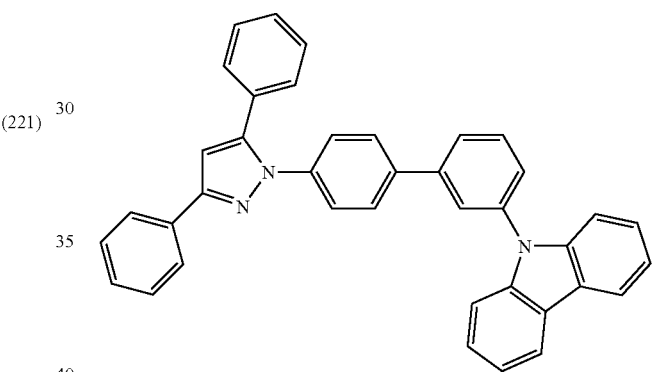
(225) 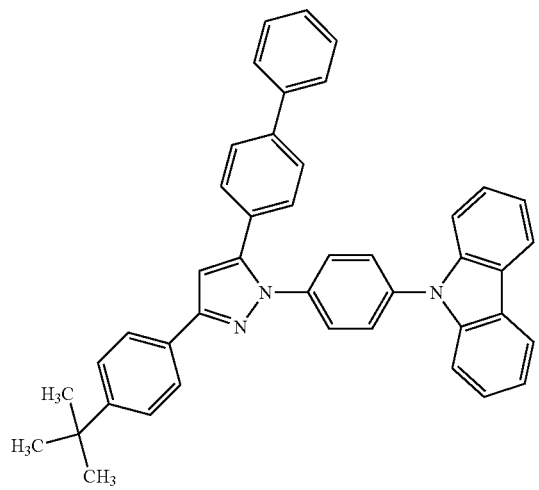

[Chemical Formula 63]
(226) 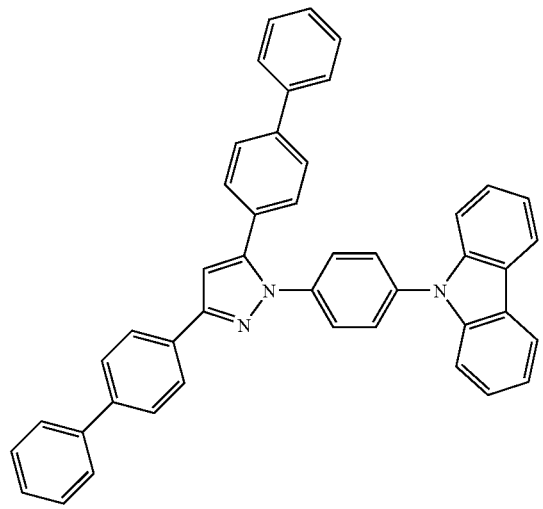
(227) 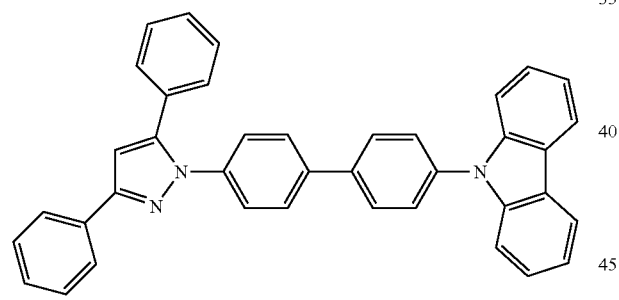
(228) 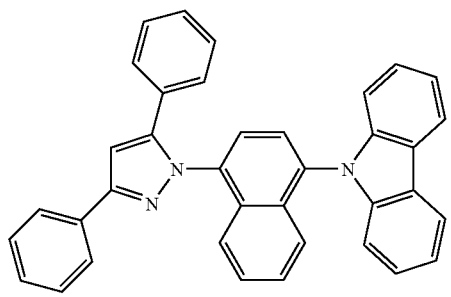
(229) 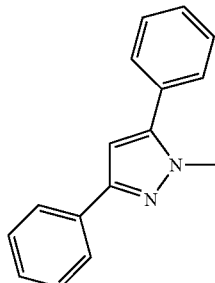
(230) 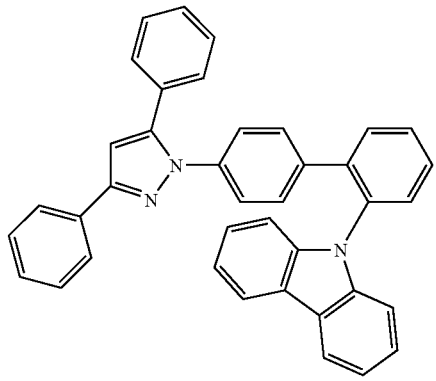
(231) 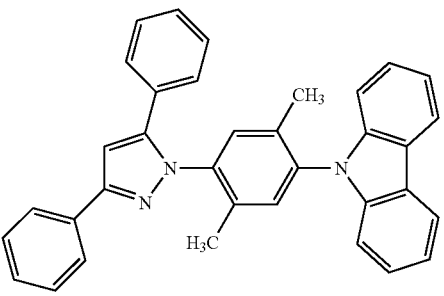

[Chemical Formula 64]
(232)
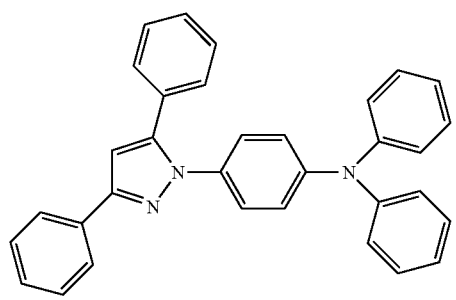
(233)
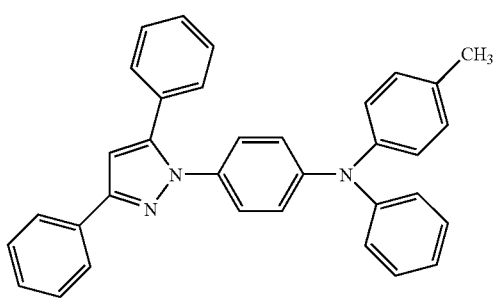
(234)
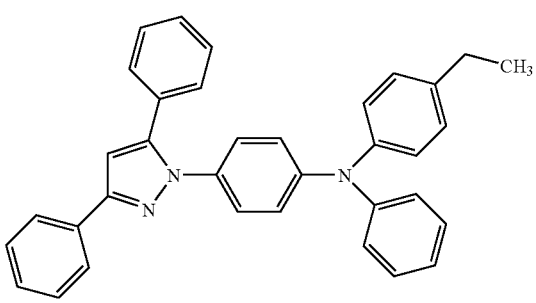
(235)
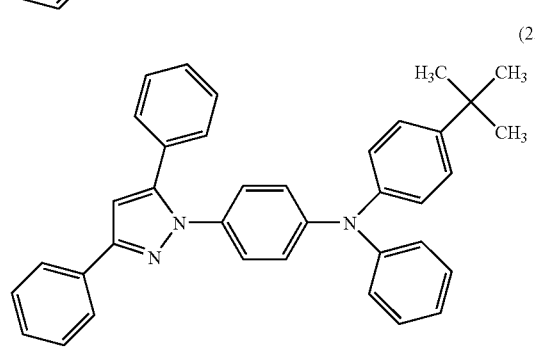
(236)
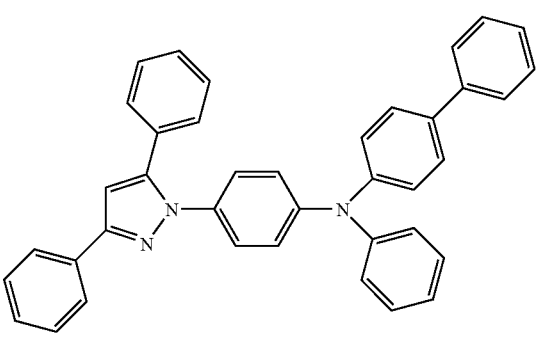
(237)
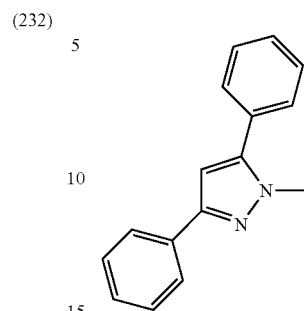
[Chemical Formula 65]
(238)
(239)
(240)

(241)
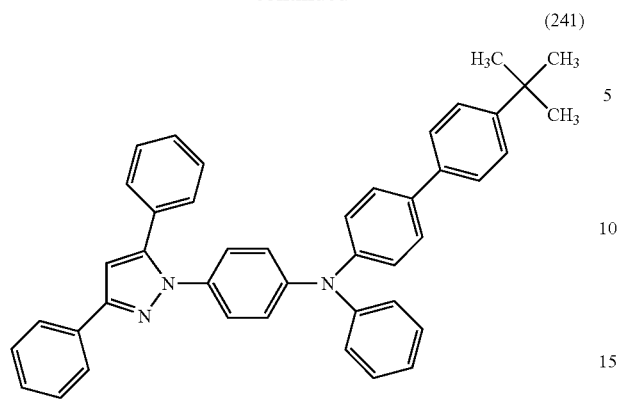
(242)
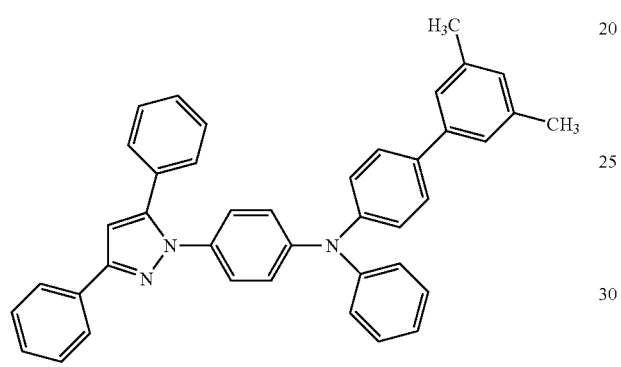
(243)
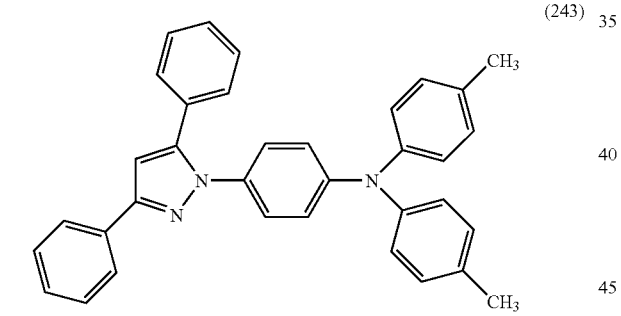
[Chemical Formula 66]
(244)
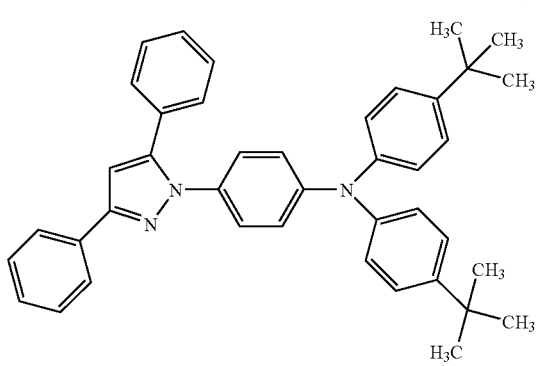
(245)
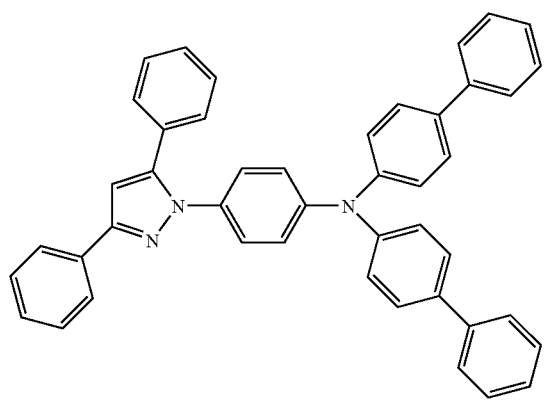
(246)
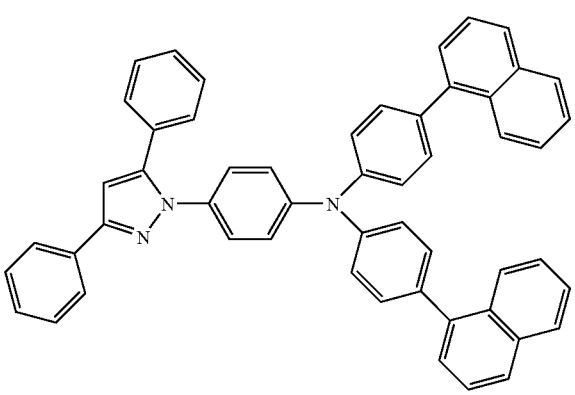
(247)
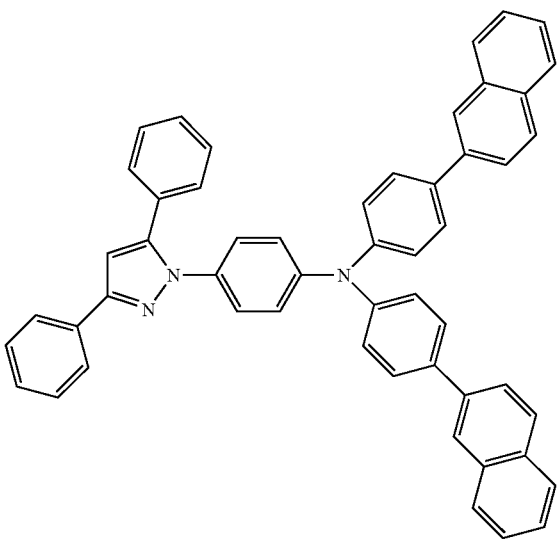

-continued
(248)
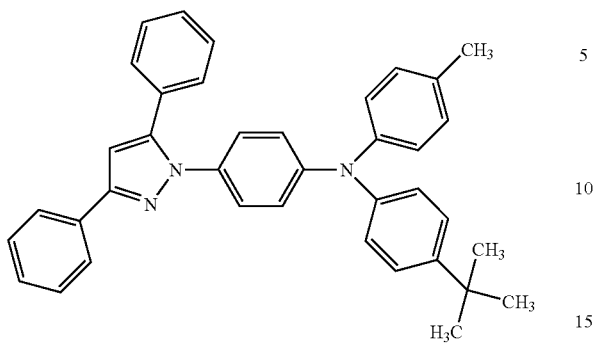
(249)
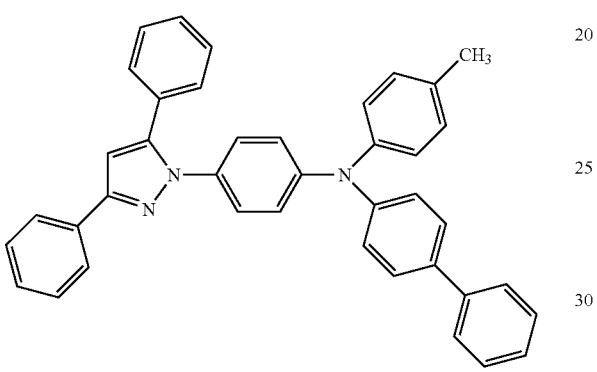
[Chemical Formula 67]
(250)
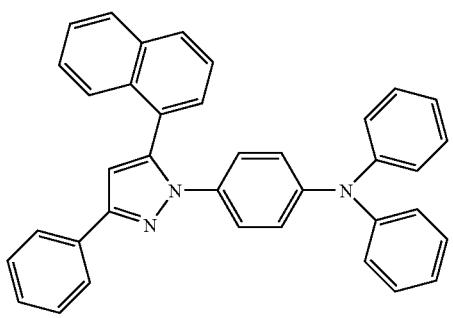
(251)
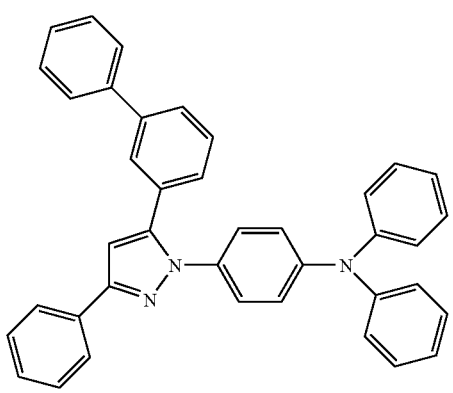
-continued
(252)
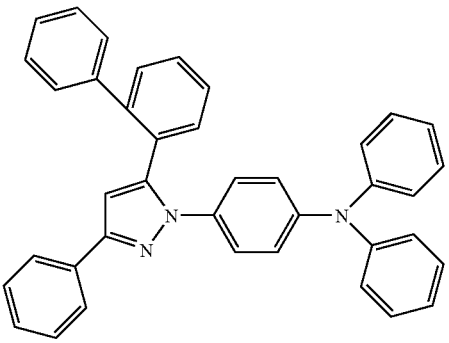
(253)
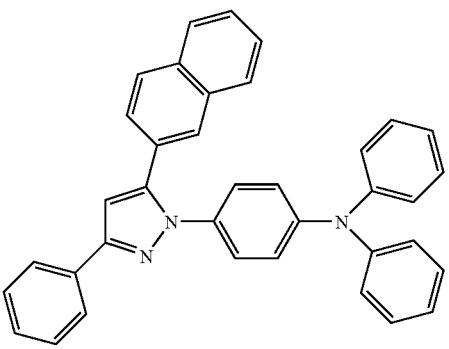
(254)
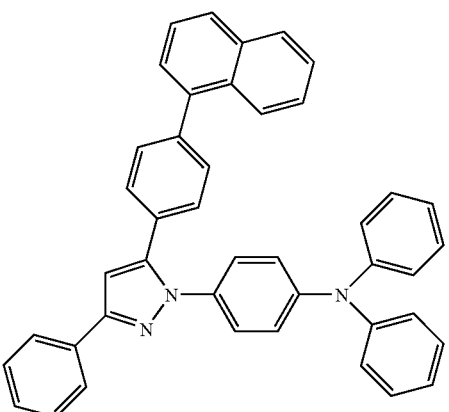
(255)
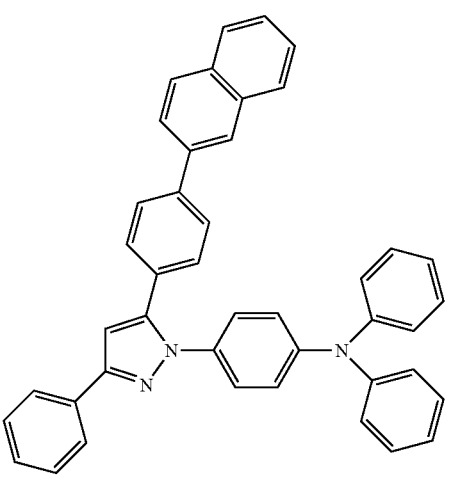

[Chemical Formula 68]
(256) 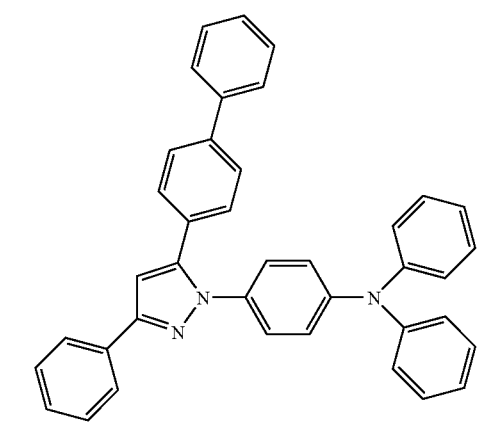
(257) 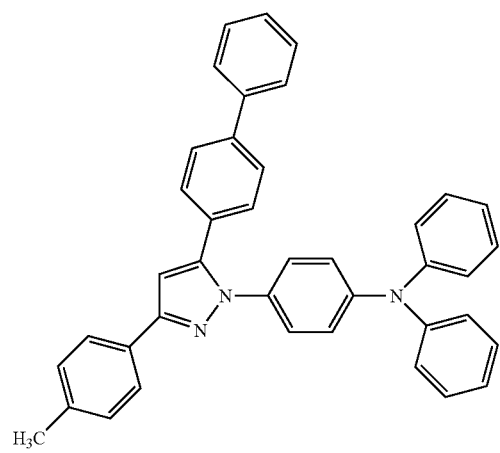
(258) 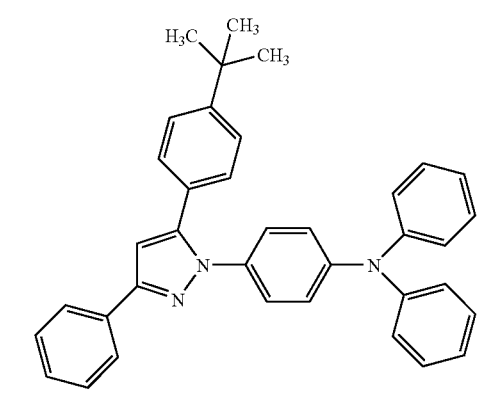
(259) 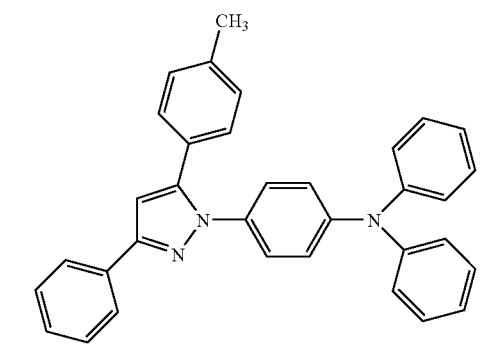
(260) 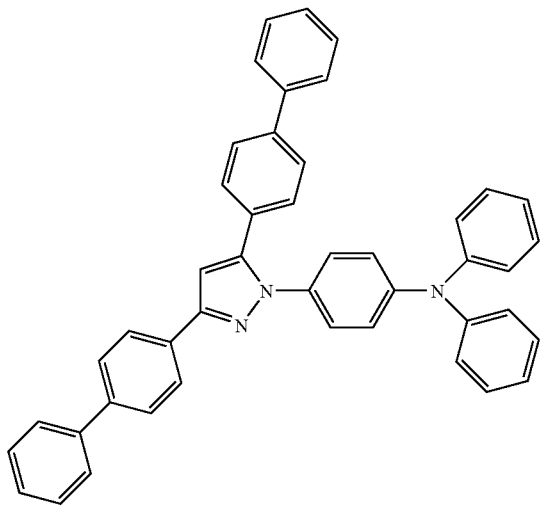
(261) 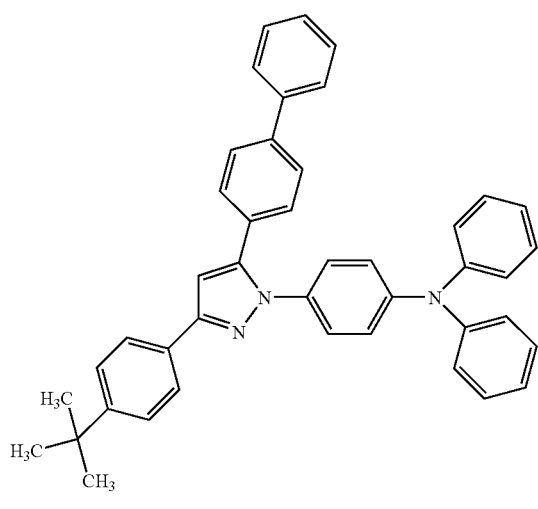
[Chemical Formula 69]
(262) 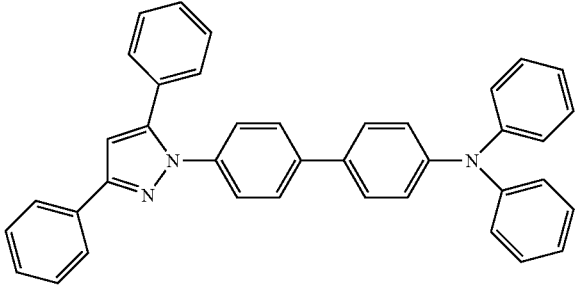

(263)
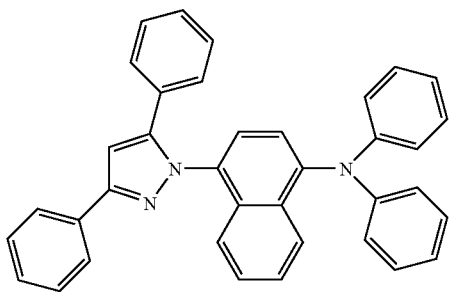
(264)
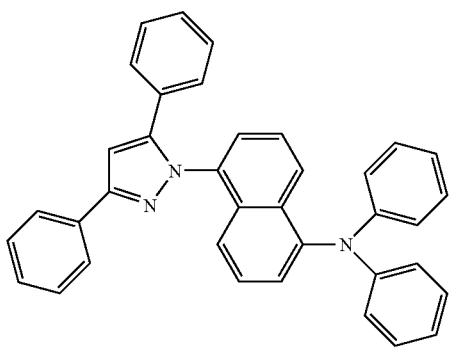
(265)
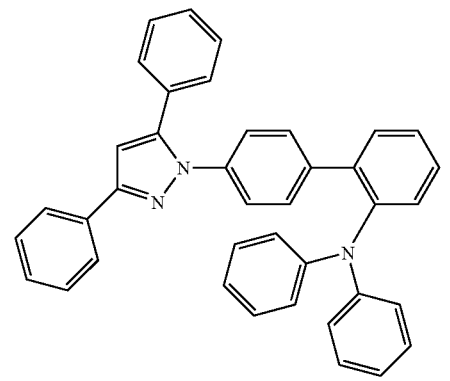
(266)
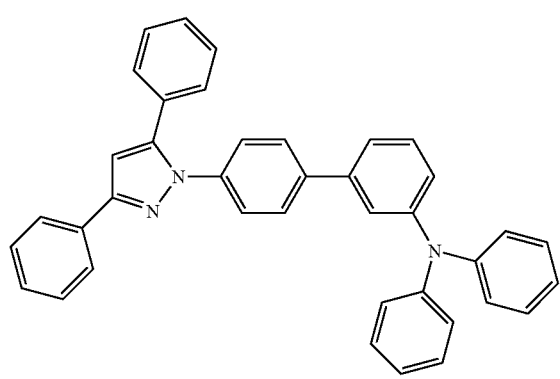
(267)
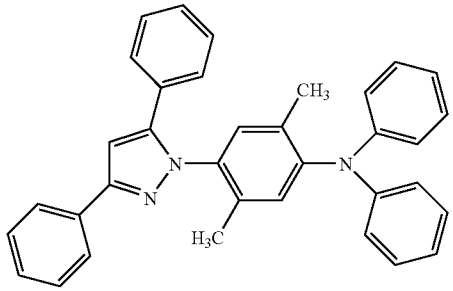
[Chemical Formula 70]
(268)
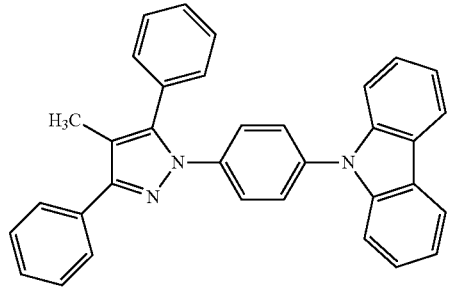
(269)
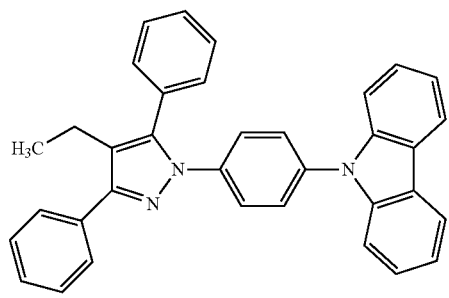
(270)
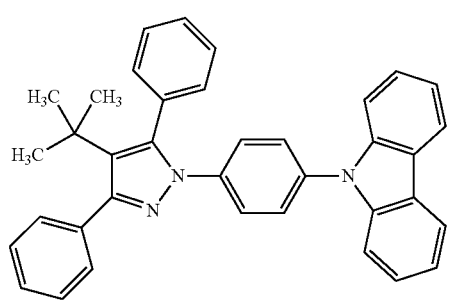
(271)
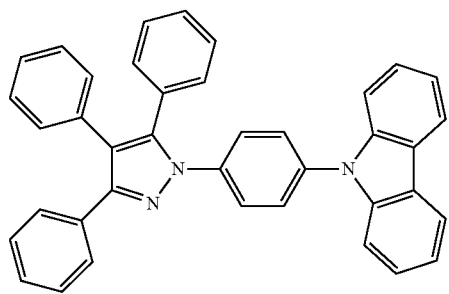

[Chemical Formula 71]

(272)
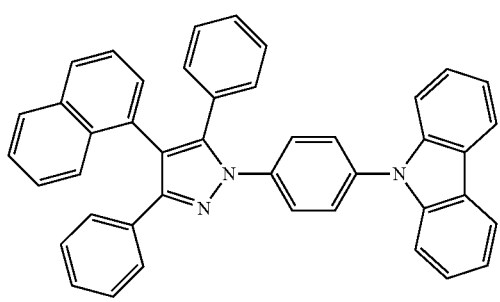

(273)
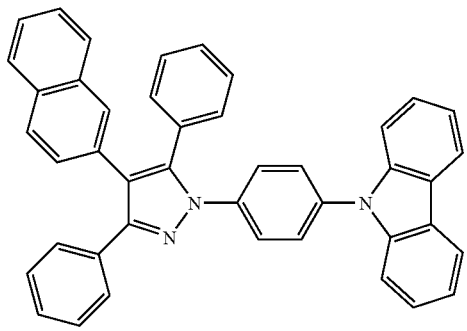

(274)
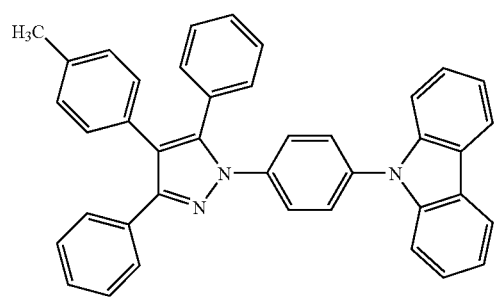

(275)
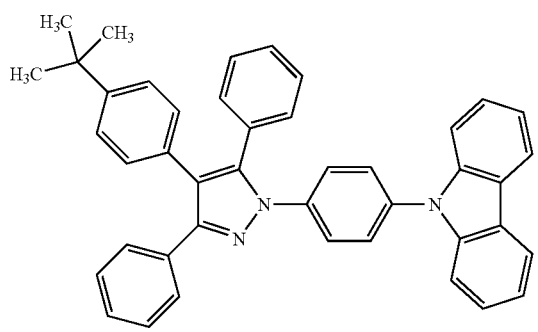

A variety of reactions can be applied to a synthesis method of a derivative with a heteroaromatic ring according to an embodiment of the present invention. For example, the derivative with a heteroaromatic ring according to an embodiment of the present invention represented by General Formula (G1) below can be synthesized by synthesis reactions described below. Note that the synthesis method of a derivative with a heteroaromatic ring according to an embodiment of the present invention is not limited to the following synthesis method.

[Chemical Formula 72]

(G1)
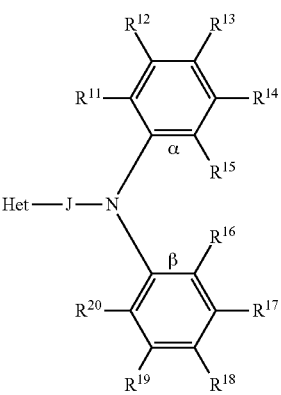

In General Formula (G1), $R^{11}$ to $R^{20}$ are independently a hydrogen atom, an alkyl group having 1 to 4 carbon atoms, or a substituted or unsubstituted aryl group having 6 to 10 carbon atoms in a ring. When $R^{11}$ to $R^{20}$ each have a substituent, an alkyl group having 1 to 4 carbon atoms or an aryl group having 6 to 10 carbon atoms in a ring can be independently given as an example of the substituent. J represents a substituted or unsubstituted arylene group having 6 to 12 carbon atoms in a ring. When J has a substituent, an alkyl group having 1 to 4 carbon atoms can be given as an example of the substituent. Note that α and β may be bonded to each other to form a carbazole skeleton. Het is a substituent represented by General Formula (S1-1) or (S1-2) below.

[Chemical Formula 73]

(S1-1)
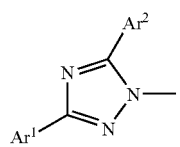

In General Formula (S1-1), $Ar^1$ and $Ar^2$ are independently a substituted or unsubstituted aryl group having 6 to 10 carbon atoms in a ring. When $Ar^1$ and $Ar^2$ each have a substituent, an alkyl group having 1 to 4 carbon atoms or an aryl group having 6 to 10 carbon atoms in a ring can be independently given as an example of the substituent.

[Chemical Formula 74]

(S1-2)
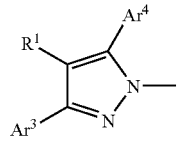

In General Formula (S1-2), $Ar^3$ and $Ar^4$ are independently a substituted or unsubstituted aryl group having 6 to 10 carbon atoms in a ring. $R^1$ is a hydrogen atom, an alkyl group having 1 to 4 carbon atoms, or an aryl group having 6 to 10 carbon atoms in a ring. When $Ar^3$ and $Ar^4$ each have a substituent, an alkyl group having 1 to 4 carbon atoms or an aryl group having 6 to 10 carbon atoms in a ring can be independently given as an example of the substituent.

<Synthesis method of Compound represented by General Formula (G1)>

The derivative with a heteroaromatic ring represented by General Formula (G1) can be synthesized as shown in the following Reaction Scheme 1. That is, a halogenated compound with a heteroaromatic ring (Compound A1) and an amine compound (Compound A2) are coupled in the presence of a base by a Buchwald-Hartwig reaction using a palladium catalyst or by an Ullmann reaction using copper or a copper compound, so that the derivative with a heteroaromatic ring (General Formula (G1)) can be obtained.

Reaction Scheme 1

[Chemical Formula 75]

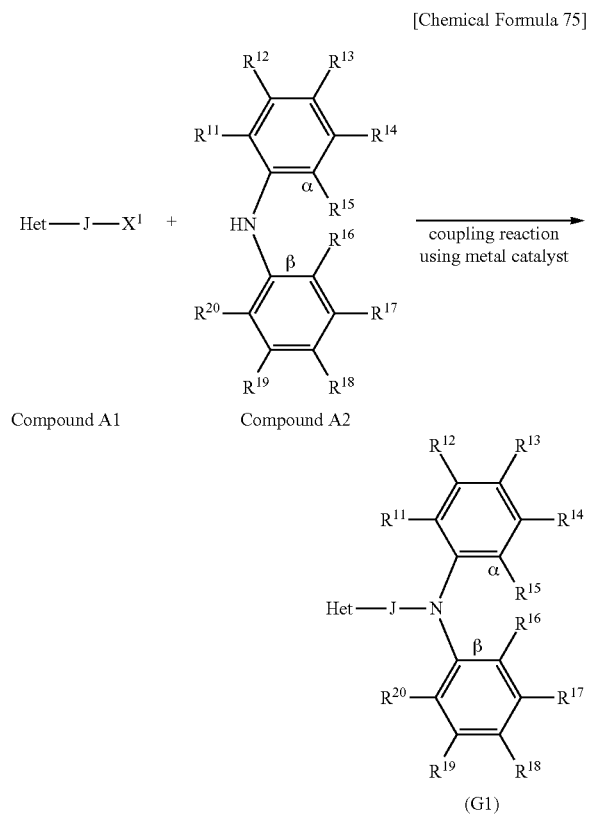

In Reaction Scheme 1, $X^1$ represents a halogen or a triflate group, and iodine or bromine can be used as the halogen. In General Formula (G1), $R^{11}$ to $R^{20}$ are independently a hydrogen atom, an alkyl group having 1 to 4 carbon atoms, or a substituted or unsubstituted aryl group having 6 to 10 carbon atoms in a ring. When $R^{11}$ to $R^{20}$ each have a substituent, an alkyl group having 1 to 4 carbon atoms or an aryl group having 6 to 10 carbon atoms in a ring can be independently given as an example of the substituent. J represents a substituted or unsubstituted arylene group having 6 to 12 carbon atoms in a ring. When J has a substituent, an alkyl group having 1 to 4 carbon atoms can be given as an example of the substituent. Note that α and β may be bonded to each other to form a carbazole skeleton. Het is a substituent represented by General Formula (S1-1) or (S1-2) below.

[Chemical Formula 76]

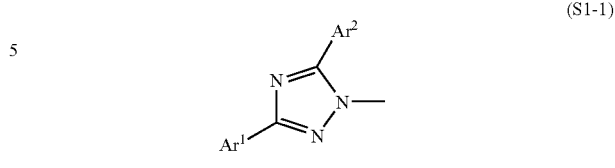

(S1-1)

In General Formula (S1-1), $Ar^1$ and $Ar^2$ are independently a substituted or unsubstituted aryl group having 6 to 10 carbon atoms in a ring. When $Ar^1$ and $Ar^2$ each have a substituent, an alkyl group having 1 to 4 carbon atoms or an aryl group having 6 to 10 carbon atoms in a ring can be independently given as an example of the substituent.

[Chemical Formula 77]

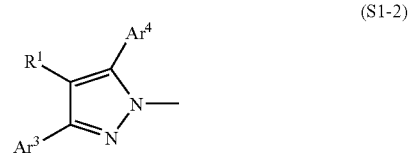

(S1-2)

In General Formula (S1-2), $Ar^3$ and $Ar^4$ are independently a substituted or unsubstituted aryl group having 6 to 10 carbon atoms in a ring. $R^1$ is a hydrogen atom, an alkyl group having 1 to 4 carbon atoms, or an aryl group having 6 to 10 carbon atoms in a ring. When $Ar^3$ and $Ar^4$ each have a substituent, an alkyl group having 1 to 4 carbon atoms or an aryl group having 6 to 10 carbon atoms in a ring can be independently given as an example of the substituent.

In the case where the Buchwald-Hartwig reaction is carried out in Reaction Scheme 1, bis(dibenzylideneacetone)palladium(0), palladium(II) acetate, or the like can be used as the palladium catalyst. Examples of ligands of the palladium catalyst which can be used in Reaction Scheme 1 are tri(tert-butyl)phosphine, tri(n-hexyl)phosphine, tricyclohexylphosphine, and the like. Examples of bases which can be used in Reaction Scheme 1 are organic bases such as sodium tert-butoxide, inorganic bases such as potassium carbonate, and the like. Examples of solvents which can be used in Reaction Scheme 1 are toluene, xylene, benzene, tetrahydrofuran, and the like.

The case of performing the Ullmann reaction in Reaction Scheme 1 is described. In Reaction Scheme 1, copper(I) iodide, copper(II) acetate, or the like can be used as the copper compound. Further, copper can be used other than the copper compound. An example of a base which can be used in Reaction Scheme 1 is an inorganic base such as potassium carbonate. Examples of solvents which can be used in Reaction Scheme 1 are 1,3-dimethyl-3,4,5,6-tetrahydro-2(1H)pyrimidinone (DMPU), toluene, xylene, benzene, and the like. In the Ullmann reaction, the target substance can be obtained in a shorter time and in a higher yield when the reaction temperature is 100° C. or higher; therefore, it is preferable to use DMPU or xylene that has a high boiling point. Because the reaction temperature is further preferably 150° C. or higher, DMPU is more preferably used.

(Embodiment 2)

In this embodiment, an example of a light-emitting element in which any of the derivatives with a heteroaromatic ring described in the above embodiment is used for a light-emitting layer is described with reference to drawings.

FIG. 1 shows an example of a light-emitting element in which an EL layer 102 including a light-emitting layer 113 is interposed between a first electrode 101 and a second electrode 103.

By application of a voltage to such a light-emitting element, holes injected from the first electrode 101 side and electrons injected from the second electrode 103 side recombine in the light-emitting layer 113 to bring a light-emitting organic compound into an excited state. Light is emitted when the light-emitting organic compound in the excited state returns to the ground state. Note that in the light-emitting element described in this embodiment, the first electrode 101 functions as an anode and the second electrode 103 functions as a cathode. It is needless to say that the order of stacking layers in the structure illustrated in FIG. 1 may be reversed.

The first electrode 101 functioning as an anode is preferably formed using a metal, an alloy, an electrically conductive compound, a mixture thereof, or the like each having a high work function (specifically, a work function of 4.0 eV or higher). Specifically, for example, indium tin oxide (ITO), indium tin oxide containing silicon or silicon oxide, indium zinc oxide (IZO), indium oxide containing tungsten oxide and zinc oxide, and the like can be given. Other than the above, gold (Au), platinum (Pt), nickel (Ni), tungsten (W), chromium (Cr), molybdenum (Mo), iron (Fe), cobalt (Co), copper (Cu), palladium (Pd), titanium (Ti), or the like may be used.

Note that in the case where in the EL layer 102, a layer in contact with the first electrode 101 is formed using a composite material of an organic compound and an electron acceptor (acceptor), a substance used for the first electrode 101 can be selected without being limited by the work function. For example, aluminum (Al), silver (Ag), an alloy containing aluminum (e.g., Al—Si), or the like can be used.

Note that the first electrode 101 can be formed by, for example, a sputtering method, an evaporation method (including a vacuum evaporation method), or the like.

The EL layer 102 formed over the first electrode 101 includes at least the light-emitting layer 113 and includes any of the derivatives with a heteroaromatic ring described in the above embodiment. For part of the EL layer 102, a known substance can be used, and either a low molecular compound or a high molecular compound may be used. Note that the substance used for forming the EL layer 102 may contain an inorganic compound in part.

Further, as illustrated in FIG. 1, the EL layer 102 includes the light-emitting layer 113 and also the following layers stacked in appropriate combination: a hole-injection layer 111 including a substance having a high hole-injection property, a hole-transport layer 112 including a substance having a high hole-transport property, an electron-transport layer 114 including a substance having a high electron-transport property, an electron-injection layer 115 including a substance having a high electron-injection property, and the like.

The hole-injection layer 111 includes a substance having a high hole-injection property. As the substance having a high hole-injection property, a metal oxide such as molybdenum oxide, titanium oxide, vanadium oxide, rhenium oxide, ruthenium oxide, chromium oxide, zirconium oxide, hafnium oxide, tantalum oxide, silver oxide, tungsten oxide, or manganese oxide can be used. Alternatively, a phthalocyanine-based compound such as phthalocyanine (abbreviation: $H_2Pc$), copper(II) phthalocyanine (abbreviation: CuPc), or vanadyl phthalocyanine (abbreviation: VOPc) can be used.

Further, as examples of low molecular organic compounds, any of the following aromatic amine compounds can be used: 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenyl carbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1), and the like.

Further alternatively, any of high molecular compounds (e.g., oligomers, dendrimers, or polymers) can be used. For example, any of the following high molecular compounds can be used: poly(N-vinylcarbazole) (abbreviation: PVK), poly (4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD). Alternatively, a high molecular compound to which acid is added, such as poly(3,4-ethylenedioxythiophene)/poly(styrenesulfonic acid) (PEDOT/PSS), or polyaniline/poly(styrenesulfonic acid) (PAni/PSS), can be used.

Alternatively, for the hole-injection layer 111, a composite material formed by combining an organic compound and an electron acceptor (acceptor) may be used. Such a composite material has excellent hole-injection and hole-transport properties because the electron acceptor generates holes in the organic compound. In this case, as the organic compound, a material that is excellent in transport of the generated holes (a substance having a high hole-transport property) is preferably used.

Note that an organic compound used for the above composite material preferably has a high hole-transport property. Specifically, a substance having a hole mobility of $10^{-6}$ cm²/Vs or more is preferably used. Further, this organic compound is not to be construed as being limited to such substances as long as it has a higher hole-transport property than an electron-transport property. Examples of the organic compound which can be used for the composite material are specifically given below.

Examples of the organic compounds that can be used for the composite material include aromatic amine compounds such as TDATA, MTDATA, DPAB, DNTPD, DPA3B, PCzPCA1, PCzPCA2, PCzPCN1, 4,4'-bis[N-(1-naphthyl)-N-phenylamino]biphenyl (abbreviation: NPB), and s(3-methylphenyl)-N,N'-diphenyl-[1,1'-biphenyl]-4,4'-diamine (abbreviation: TPD) and carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)]phenyl-10-phenylanthracene (abbreviation: CzPA), and 1,4-bis[4-(N-carbazolyl)phenyl-2,3,5,6-tetraphenylbenzene.

Any of the following aromatic hydrocarbon compounds may be used: 2-tert-butyl-9,10-di(2-naphthyl)anthracene (abbreviation: t-BuDNA), 2-tert-butyl-9,10-di(1-naphthyl) anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl) anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2- tert-butyl-anthracene, 9,10-bis[2-(1-naphthyl)phenyl]anthracene, and 2,3,6,7-tetramethyl-9,10-di(1-naphthyl)anthracene.

Any of the following aromatic hydrocarbon compounds may also be used: 2,3,6,7-tetramethyl-9,10-di(2-naphthyl) anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), and 9,10-bis[4-(2,2-diphenylvinyl) phenyl]anthracene (abbreviation: DPVPA).

Further, a derivative with a heteroaromatic ring according to an embodiment of the present invention may be used.

As examples of electron acceptors that can be used for the composite material, there are organic compounds such as 7,7,8,8-tetracyano-2,3,5,6-tetrafluoroquinodimethane (abbreviation: $F_4$-TCNQ) and chloranil, transition metal oxides, and the like. Oxides of metals belonging to Group 4 to Group 8 of the periodic table may be used. For example, vanadium oxide, niobium oxide, tantalum oxide, chromium oxide, molybdenum oxide, tungsten oxide, manganese oxide, and rhenium oxide are suitable because of their high electron-accepting properties. Among these, molybdenum oxide is suitable because it is stable in air and its hygroscopic property is low so that it can be easily handled.

Note that a composite material formed using any of the above-mentioned high molecular compounds such as PVK, PVTPA, PTPDMA, and Poly-TPD and any of the above-mentioned electron acceptors may be used for the hole-injection layer 111.

The hole-transport layer 112 includes a substance having a high hole-transport property. As a substance having a high hole-transport property, there are aromatic amine compounds such as NPB, TPD, 4,4'-bis[N-(9,9-dimethylfluoren-2-yl)-N-phenylamino]biphenyl (abbreviation: DFLDPBi), and 4,4'-bis[N-(spiro-9,9'-bifluoren-2-yl)-N-phenylamino]biphenyl (abbreviation: BSPB). The substances mentioned here are mainly substances having a hole mobility of $10^{-6}$ cm$^2$/Vs or more. Note that the hole-transport layer 112 may have a single-layer structure or a stacked-layer structure.

Alternatively, for the hole-transport layer 112, a high molecular compound such as PVK, PVTPA, PTPDMA, or Poly-TPD can be used.

Further alternatively, any of the derivatives with a heteroaromatic ring according to an embodiment of the present invention can be used as a hole-transport material because of a bipolar property and a hole-transport property.

The light-emitting layer 113 includes a substance having a high light-emitting property. Note that in this embodiment, description is given of the case in which any of the derivatives with a heteroaromatic ring described in the above embodiment is used for the light-emitting layer. The above derivatives with a heteroaromatic ring are suitably used as a host material in a light-emitting layer where a substance having a high light-emitting property (a guest material) is dispersed in another substance (a host material). However, an embodiment of the disclosed invention is not to be construed as being limited to this structure. Any of the above derivatives with a heteroaromatic ring may be used alone as the light-emitting layer.

In the case where any of the derivatives with a heteroaromatic ring described in the above embodiment is used as a host material and a material that emits fluorescence is used as a guest material, it is preferable to use, as the guest material, a material whose lowest unoccupied molecular orbital (LUMO) level is lower and whose highest occupied molecular orbital (HOMO) level is higher than those of the derivative with a heteroaromatic ring described in the above embodiment. Examples of materials for blue light emission include N,N-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), and the like. In addition, examples of materials for green light emission include N-(9,10-diphenyl-2-anthryl)-N,9-diphenyl-9H-carbazol-3-amine (abbreviation: 2PCAPA), [9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), and the like. Further, examples of materials for yellow light emission include rubrene, 5,12-bis(1,1'-biphenyl-4-yl)-6,11-diphenyltetracene (abbreviation: BPT), and the like. Furthermore, examples of materials for red light emission include N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), and the like.

Alternatively, in the case where any of the derivatives with a heteroaromatic ring described in the above embodiment is used as a host material and a material that emits phosphorescence is used as a guest material, it is preferable to use, as the guest material, a material having lower triplet excitation energy than the derivative with a heteroaromatic ring described in the above embodiment. Examples of such materials include organometallic complexes such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III)picolinate (abbreviation: FIrpic), bis[2-(3',5'-bistrifluoromethylphenyl)pyridinato-N,C$^{2'}$]iridium(III) picolinate (abbreviation: Ir(CF$_3$ppy)$_2$(pic)), bis[2-(4',6'-difluorophenyl)pyridinato-N,C$^{2'}$]iridium(III) acetylacetonate (abbreviation: FIracac), tris(2-phenylpyridinato-N,C$^{2'}$)iridium(III) (abbreviation: Ir(ppy)$_3$), bis(2-phenylpyridinato)iridium(III) acetylacetonato (abbreviation: Ir(ppy)$_2$(acac)), tris(acetylacetonato) (monophenanthroline)terbium(III) (abbreviation: Tb(acac)$_3$(Phen)), bis(benzo[h]quinolinato)iridium(III) acetylacetonate (abbreviation: Ir(bzq)$_2$(acac)), bis(2,4-diphenyl-1,3-oxazolato-N,C$^{2'}$)iridium(III) acetylacetonate (abbreviation: Ir(dpo)$_2$(acac)), bis[2-(4'-perfluorophenylphenyl)pyridinato]iridium(III)acetylacetonate (abbreviation: Ir(p-PF-ph)$_2$(acac)), bis(2-phenylbenzothiazolato-N,C$^{2'}$)iridium(III) acetylacetonate (abbreviation: Ir(bt)$_2$(acac)), bis[2-(2'-benzo[4,5-α]thienyl)pyridinato-N,C$^{3'}$]iridium(III) acetylacetonate (abbreviation: Ir(btp)$_2$(acac)), bis(1-phenylisoquinolinato-N,C$^{2'}$)iridium(III) acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), (acetylacetonato)bis(2,3,5-triphenylpyrazinato) iridium(III) (abbreviation: Ir(tppr)$_2$(acac)), 2,3,7,8,12,13,17,18-octaethyl-21H,23H-porphyrin platinum(II) (abbreviation: PtOEP), tris(1,3-diphenyl-1,3-propanedionato)(monophenanthroline)europium(III) (abbreviation: Eu(DBM)$_3$(Phen)), and tris[1-(2-thenoyl)-3,3,3-trifluoroacetonato](monophenanthroline)europium(III) (abbreviation: Eu(TTA)$_3$(Phen)).

Since the derivatives with a heteroaromatic ring described in the above embodiment have an electron-transport property, by using any of them for a light-emitting layer, a light-emitting layer having a high electron-transport property can be obtained. Such a light-emitting layer can emit light with high efficiency when a guest material having a high electron-trapping property is used.

in addition, as a substance (a host material) in which a light-emitting substance (a guest material) is dispersed, plural kinds of substances can be used. Therefore, the light-emitting layer may include a second host material in addition to the derivatives with a heteroaromatic ring described in the above embodiment.

Further, as a light-emitting substance, any of the derivatives with a heteroaromatic ring according to an embodiment of the present invention can be used alone or as a guest material.

The electron-transport layer 114 includes a substance having a high electron-transport property. For the electron-transport layer 114, it is possible to use a metal complex such as Alq$_3$, tris(4-methyl-8-quinolinolato)aluminum (abbreviation: Almq$_3$), bis(10-hydroxybenzo[h]quinolinato)beryllium (abbreviation: BeBq$_2$), BAlq, Zn(BOX)$_2$, or bis[2-(2'-hydroxyphenyl)benzothiazolato]zinc(II) (abbreviation: Zn(BTZ)$_2$). Alternatively, it is possible to use a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butyl-phenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazole-2-yl)stilbene (abbreviation: BzOs). Further alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2%-bipyridine-6,6'-diyl)] (abbreviation: PF-BPy) may be used. The substances described here are mainly substances having electron mobility of $10^{-6}$ cm$^2$/Vs or more.

In addition, the electron-transport layer 114 may have a single-layer structure or a stacked-layer structure.

Any of the above derivatives with a heteroaromatic ring can be used as an electron-transport material because of a bipolar property and an electron-transport property.

The electron-injection layer 115 includes a substance having a high electron-injection property. For the electron-injection layer 115, an alkali metal, an alkaline earth metal, or a compound thereof, such as lithium (Li), cesium (Cs), calcium (Ca), lithium fluoride (LiF), cesium fluoride (CsF), calcium fluoride (CaF$_2$), or lithium oxide (LiO$_x$) can be used. Alternatively, a rare earth metal compound such as erbium fluoride (ErF$_3$) can be used. Further alternatively, any of the above-described substances for forming the electron-transport layer 114 may be used.

For the electron-injection layer 115, a composite material formed by combining an organic compound and an electron donor (donor) may be used. Such a composite material has excellent an electron-injection and electron-transport properties because the electron donor generates electrons in the organic compound. In this case, as the organic compound, a material that is excellent in transport of the generated electrons is preferably used: for example, any of the above-described substances for forming the electron-transport layer 114 can be used. Alternatively, any of the derivatives with a heteroaromatic ring according to an embodiment of the present invention can be used. As the electron donor, a substance exhibiting an electron-donating property to the organic compound is used. Specifically, it is preferable to use any of alkali metals, alkaline earth metals, or rare earth metals, such as lithium, cesium, magnesium, calcium, erbium, ytterbium, or the like. Alternatively, it is preferable to use any of alkali metal oxides or alkaline earth metal oxides: lithium oxide, calcium oxide, barium oxide, or the like. A Lewis base such as magnesium oxide can also be used. Alternatively, an organic compound such as tetrathiafulvalene (abbreviation: TTF) can be used.

Note that the hole-injection layer 111, hole-transport layer 112, light-emitting layer 113, electron-transport layer 114, and electron-injection layer 115 which are described above each can be formed by an evaporation method (including a vacuum evaporation method), an inkjet method, a coating method, or the like.

The second electrode 103 functioning as a cathode is preferably formed using a metal, an alloy, an electrically conductive compound, a mixture thereof, or the like which has a low work function (preferably, a work function of 3.8 eV or lower). Specifically, any of the following materials can be used: aluminum, silver, and the like, as well as elements that belong to Group 1 or Group 2 of the periodic table, that is, alkali metals such as lithium and cesium or alkaline earth metals such as magnesium, calcium, and strontium, or alloys thereof; rare earth metals such as europium and ytterbium, or alloys thereof.

Note that, when a layer in contact with the second electrode 103 which is included in the EL layer 102 is formed using the above-described composite material of the organic compound and the electron donor (donor), a material used for the second electrode 103 can be selected without being limited by the work function. For example, any of a variety of conductive materials such as Al, Ag, ITO, and indium oxide-tin oxide containing silicon or silicon oxide can be used.

In the formation of the second electrode 103, a vacuum evaporation method or a sputtering method can be used. Alternatively, when a silver paste or the like is used, a coating method, an inkjet method, or the like may be used.

In the above-described light-emitting element, holes and electrons generated by a potential difference between the first electrode 101 and the second electrode 103 recombine in the EL layer 102, thereby emitting light. Then, this emitted light is extracted out through one of or both the first electrode 101 and the second electrode 103. Accordingly, one of or both the first electrode 101 and the second electrode 103 have a property of transmitting visible light.

Note that with the use of the light-emitting element described in this embodiment, a passive-matrix light-emitting device or an active-matrix light-emitting device in which drive of the light-emitting element is controlled by a thin film transistor (TFT) can be fabricated.

Note that there is no particular limitation on the structure of the TFT in the case of fabricating an active-matrix light-emitting device. Further, either an n-type TFT or a p-type TFT may be used. Furthermore, there is no particular limitation on a semiconductor material used for the TFT. For example, any of the following materials can be used: silicon-based semiconductor materials (which may be amorphous, crystalline, or single crystal), germanium-based semiconductor materials, chalcogenide-based semiconductor materials, or other variety of semiconductor materials. Obviously, an oxide semiconductor material may be used.

In this embodiment, any of the above-described derivatives with heteroaromatic rings is used for forming the light-emitting layer 113. Accordingly, a light-emitting element with high power efficiency and long lifetime can be provided.

Note that the structure described in this embodiment can be combined with the structure described in the above embodiment, as appropriate.

(Embodiment 3)

The light-emitting element according to an embodiment of the disclosed invention may have a plurality of light-emitting layers. By producing light emission from each light-emitting layer, light which is a combination thereof can be obtained. White light emission can thus be obtained, for example. In this embodiment, an embodiment of a light-emitting element having a plurality of light-emitting layers is described with reference to drawing.

Figure 2:
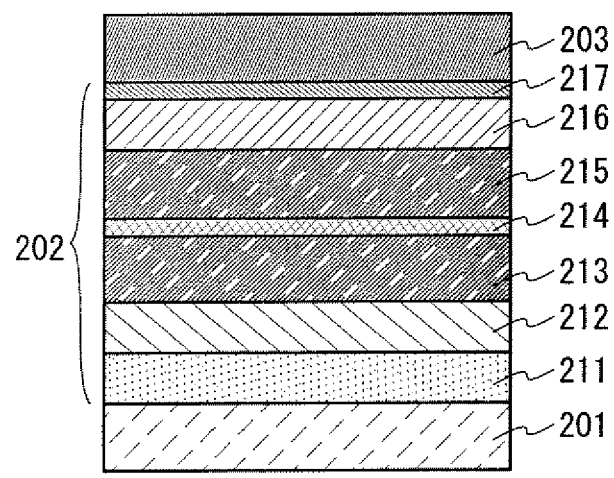
FIG. 2 illustrates a light-emitting element.

In FIG. 2, a first light-emitting layer 213 and a second light-emitting layer 215 are provided between a first electrode 201 and a second electrode 203 to enable emission of light that is a combination of light emitted from the first light-emitting layer 213 and light emitted from the second light-emitting layer 215. A separation layer 214 is preferably formed between the first light-emitting layer 213 and the second light-emitting layer 215.

By application of a voltage such that the potential of the first electrode 201 is higher than that of the second electrode 203, a current flows between the first electrode 201 and the second electrode 203, and holes or electrons move to the first light-emitting layer 213, the second light-emitting layer 215, or the separation layer 214. Accordingly, a first light-emitting substance included in the first light-emitting layer 213 and a second light-emitting substance included in the second light-emitting layer 215 are raised to an excited state. Then, the light-emitting substances in the excited state emit light in transition to the ground state.

The first light-emitting layer 213 includes the first light-emitting substance typified by a fluorescent compound such as perylene, 2,5,8,11-tetra(tert-butyl)perylene (abbreviation: TBP), DPVBi, 4,4'-bis[2-(N-ethylcarbazol-3-yl)vinyl]biphenyl (abbreviation: BCzVBi), BAlq, or bis(2-methyl-8-quinolinolato)galliumchloride (abbreviation: Gamq$_2$Cl) or a phosphorescent compound such as bis{2-[3,5-bis(trifluoromethyl)phenyl]pyridinato-N,C$^{2'}$}iridium(III) picolinate (abbreviation: Ir(CF$_3$ppy)$_2$(pic)), bis[2-(4,6-difluorophenyl)pyridinato-N,C$^{2'}$]iridium(III) acetylacetonate (abbreviation: FIr(acac)), bis[2-(4,6-difluorophenyl)pyridinato-N,C$^{2'}$]iridium(III) picolinate (abbreviation: FIrpic), or bis[2-(4,6-difluorophenyl)pyridinato-N,C$^{2'}$]iridium(III) tetra(1-pyrazolyl)borate (abbreviation: FIr6), from which light emission with a peak at 450 nm to 510 nm in an emission spectrum (i.e., blue light to blue green light) can be obtained.

When a fluorescent compound is used as the first light-emitting substance, the first light-emitting layer 213 preferably has a structure in which a substance having larger singlet excited energy than that of the first light-emitting substance is used as a first host and the first light-emitting substance is dispersed as a guest. Alternatively, when a phosphorescent compound is used as the first light-emitting substance, the first light-emitting layer 213 preferably has a structure in which a substance having larger triplet excited energy than that of the first light-emitting substance is used as a first host and the first light-emitting substance is dispersed as a guest. As the first host, NPB, CBP, TCTA, or the like, which is described above, or DNA, t-BuDNA, or the like can be used. Note that the singlet excitation energy is referred to as an energy difference between a ground state and a singlet excited state. In addition, the triplet excitation energy is referred to as an energy difference between a ground state and a triplet excited state.

Further, the second light-emitting layer 215 includes any of the derivatives with a heteroaromatic ring described in the above embodiment. The structure of the second light-emitting layer 215 is similar to that of the light-emitting layer 113 which is described in the above embodiment.

In addition, the separation layer 214 can be formed using TPAQn, NPB, CBP, TCTA, Znpp$_2$, ZnBOX or the like described above, specifically. Provision of such a separation layer 214 can prevent an undesirable increase in the emission intensity of only either the first light-emitting layer 213 or the second light-emitting layer 215. Note that the separation layer 214 is not a necessary component. For example, the separation layer 214 may be provided in the case where the ratio of the emission intensity of the first light-emitting layer 213 to that of the second light-emitting layer 215 needs to be adjusted. Further, any derivative with a heteroaromatic ring which is an embodiment of the disclosed invention may be used for the separation layer 214.

Note that in this embodiment, any of the derivatives with a heteroaromatic ring described in the above embodiment is used for the second light-emitting layer 215, while another light-emitting substance is used for the first light-emitting layer 213. However, any of the derivatives with a heteroaromatic ring described in the above embodiment may be used for the first light-emitting layer 213, while another light-emitting substance may be used for the second light-emitting layer 215.

Further, although a light-emitting element including two light-emitting layers is described in this embodiment, the number of the light-emitting layers is not limited to two and may be three or more.

Note that the first electrode 201 has a structure similar to that of the first electrode 101 which is described in the above embodiment. Also, the second electrode 203 has a structure similar to that of the second electrode 103 which is described in the above embodiment.

Further, in this embodiment, description is given of an example in which a hole-injection layer 211, a hole-transport layer 212, an electron-transport layer 216, and an electron-injection layer 217 are provided. These layers can have a structure similar to that described in the above embodiment. However, these layers are not necessary components and may be provided as appropriate depending on element characteristics.

Note that the structure described in this embodiment can be combined with any structure described in the above embodiments, as appropriate.

(Embodiment 4)

In this embodiment, a light-emitting element having a plurality of EL layers (hereinafter, referred to as a stacked-type element) is described with reference to drawing.

Figure 3:
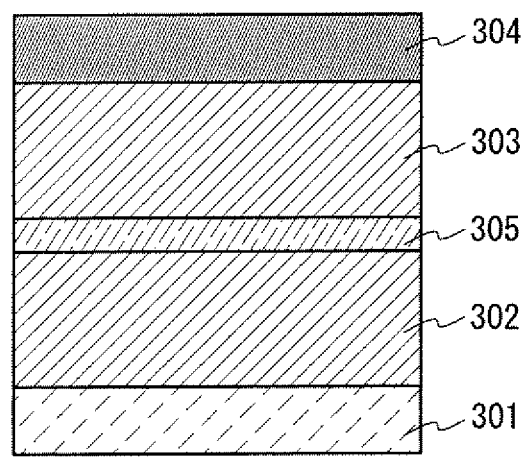
FIG. 3 illustrates a light-emitting element.

FIG. 3 illustrates a stacked-type light-emitting element that has a plurality of EL layers (a first EL layer 302 and a second EL layer 303) between a first electrode 301 and a second electrode 304. Note that although a structure in which two EL layers are formed is described in this embodiment, three or more EL layers may be formed.

In this embodiment, the first electrode 301 functions as an anode, and the second electrode 304 functions as a cathode. Note that the first electrode 301 and the second electrode 304 can have structures similar to those described in the above embodiments. Further, although the plurality of EL layers (the first EL layer 302 and the second EL layer 303) may be formed as described in the above embodiments, either layer may have a structure different from that described in the above embodiments. That is, the structures of the first EL layer 302 and the second EL layer 303 may be the same or different from each other.

Further, a charge generation layer 305 is provided between the plurality of EL layers (the first EL layer 302 and the second EL layer 303). The charge generation layer 305 has a function of injecting electrons into one of the EL layers and injecting holes into the other of the EL layers when a voltage is applied to the first electrode 301 and the second electrode 304. In this embodiment, when a voltage is applied so that the potential of the first electrode 301 is higher than that of the second electrode 304, the charge generation layer 305 injects electrons into the first EL layer 302 and injects holes into the second EL layer 303.

Note that the charge generation layer 305 preferably has a light-transmitting property in terms of light extraction efficiency. Further, the electric conductivity of the charge generation layer 305 may be lower than that of the first electrode 301 or the second electrode 304.

The charge generation layer 305 may have either a structure including an organic compound having a high hole-transport property and an electron acceptor (acceptor) or a structure including an organic compound having a high electron-transport property and an electron donor (donor). Alternatively, a structure in which both of these structures are stacked may be employed.

The description in the above embodiment can be referred to for details of the organic compound having a high hole-transport property and the electron acceptor. Also, the description in the above embodiment can be referred to for details of the organic compound having a high electron-transport property and the electron donor.

Forming the charge generation layer 305 by using the above materials can suppress an increase in drive voltage which is caused by the stack of the EL layers.

By an arrangement in which the charge generation layer partitions the plurality of EL layers, as in the light-emitting element according to this embodiment, luminance can be improved while current density is kept low. Thus, a light-emitting element that can emit light with high luminance and has long lifetime can be achieved.

Further, by forming the EL layers to emit light of different colors from each other, an emission color that is provided by the light-emitting element as a whole can be controlled. For example, by forming a light-emitting element having two EL layers such that the emission color of the first EL layer and the emission color of the second EL layer are complementary colors, the light-emitting element can provide white light emission as a whole.

Furthermore, by providing the plurality of different EL layers, a light-emitting element having a wide light emission spectrum can be easily provided. For example, a white light-emitting element with an excellent color rendering property can be obtained as the whole light-emitting element when the emission color of the first, second, and third EL layer are red, green, and blue, respectively.

Note that the structure described in this embodiment can be combined with any structure described in the above embodiments, as appropriate.

(Embodiment 5)

In this embodiment, a passive-matrix light-emitting device and an active-matrix light-emitting device each of which uses a light-emitting element are described, as an embodiment of the disclosed invention.

FIGS. 4A to 4D and FIG. 5 exemplify passive-matrix light-emitting devices.

In a passive-matrix (also called simple-matrix) light-emitting device, a plurality of anodes arranged in stripes (in stripe form) is provided orthogonal to a plurality of cathodes arranged in stripes. A light-emitting layer is formed at each intersection. Therefore, light is emitted from a light-emitting layer (hereinafter, referred to as a pixel) at an intersection of an anode selected (to which a voltage is applied) and a cathode selected.

Figure 4A:
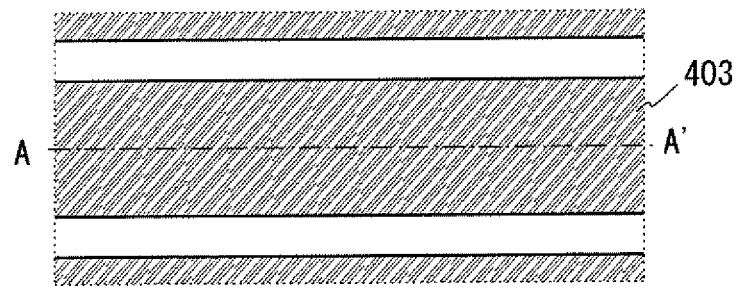
FIGS. 4A to 4D illustrate a passive-matrix light-emitting device.
Figure 4B:
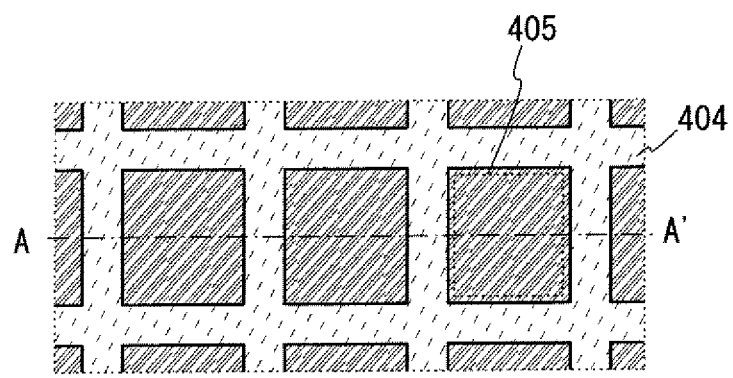
Figure 4C:
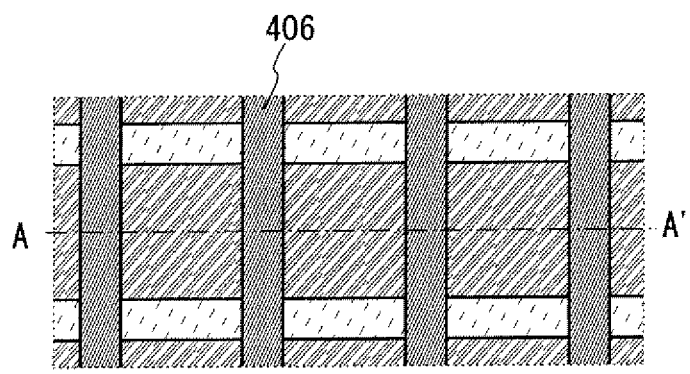
Figure 4D:
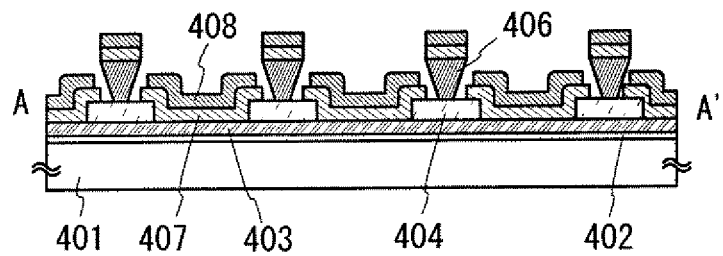

FIGS. 4A to 4C are top views of a pixel portion before sealing. FIG. 4D is a cross-sectional view taken along dashed line A-A' in each of FIGS. 4A to 4C.

Over a substrate 401, an insulating layer 402 is formed as a base insulating layer. Note that the base insulating layer is not a necessary component and thus formed as needed. A plurality of first electrodes 403 is arranged at regular intervals over the insulating layer 402 (see FIG. 4A).

In addition, a partition 404 having openings in regions corresponding to pixels is provided over the first electrodes 403. The partition 404 having openings is formed using an organic material (polyimide, acrylic, polyamide, polyimide amide, resist, or benzocyclobutene), an inorganic material (e.g., a $SiO_x$ film including an alkyl group), or the like. Note that openings 405 corresponding to the pixels serve as light-emitting regions (see FIG. 4B).

Over the partition 404, a plurality of partitions 406 is provided so as to intersect with the first electrodes 403 (see FIG. 4C). The partitions 406 are each reversely tapered and arranged in parallel to one another.

In regions over the first electrodes 403, where the partitions 406 are not formed, EL layers 407 and second electrodes 408 are provided in that order (see FIG. 4D). Here, the EL layers 407 and the second electrodes 408 are formed as plural portions, which are electrically isolated from each other. The EL layers 407 and the second electrodes 408 each having such a structure can be formed when the height of the partitions 406 exceeds the sum of the thicknesses of the EL layers 407 and the second electrodes 408.

The second electrodes 408 extend in the direction in which they intersect with the first electrodes 403. Note that over the partitions 406, a layer of the same material as the EL layer 407 and a layer of the same material as the second electrode 408 are also formed, which are isolated from the EL layer 407 and the second electrode 408.

Note that the first electrode 403 and the second electrode 408 may serve as an anode and a cathode, respectively, or vice versa. The stack structure of the EL layer 407 is adjusted depending on the polarity of the electrodes, as appropriate.

Further, the substrate 401 may be sealed so that a light-emitting element is provided in a sealed space. Sealing is carried out with an adhesive such as a seal material to attach the substrate 401 to a sealing can or a sealant. Such sealing can suppress deterioration of the light-emitting element. Note that the sealed space may be filled with filler, a dried inert gas, a drying agent (a desiccant), or the like. Sealing a drying agent enables removal of a minute amount of moisture, whereby deterioration of the light-emitting element which is caused by moisture is suppressed. Note that as a drying agent, a substance that adsorbs moisture by chemical adsorption can be used. For example, oxides of alkaline earth metals such as calcium oxide and barium oxide can be used. Alternatively, a substance that adsorbs moisture by physical adsorption, such as zeolite or silicagel, may be used.

Figure 5:
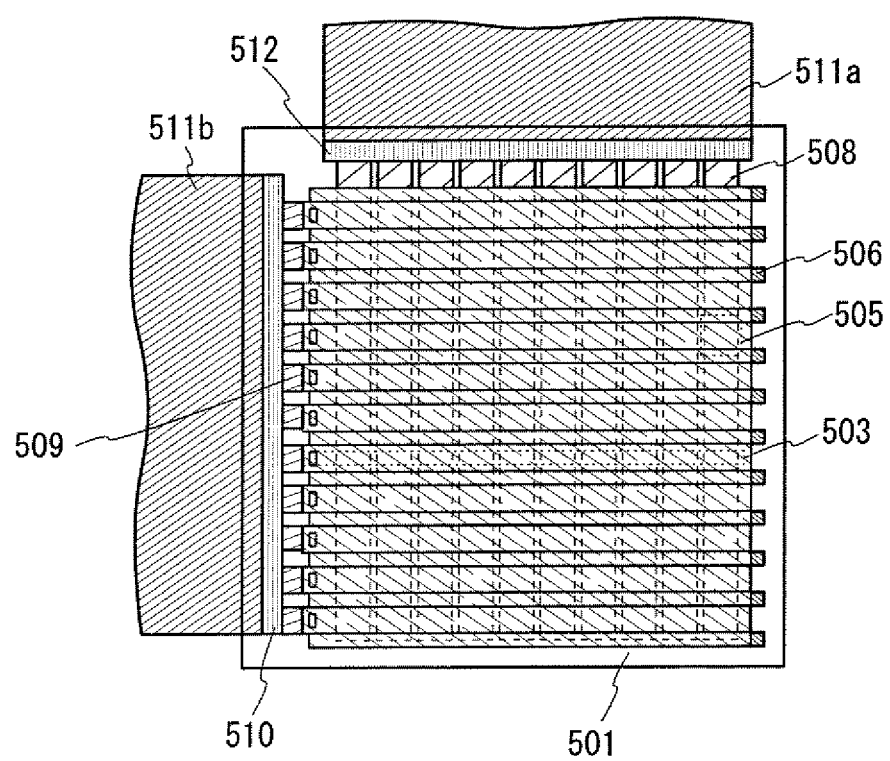
FIG. 5 illustrates a passive-matrix light-emitting device.

Next, FIG. 5 illustrates a structure of a passive-matrix light-emitting device as illustrated in FIGS. 4A to 4D, on which an FPC and the like are mounted.

In a pixel portion in FIG. 5, scan lines and data lines are arranged to intersect with each other so that they are orthogonal to each other. Note that the first electrodes 403 in FIGS. 4A to 4D correspond to scan lines 503 in FIG. 5, the second electrodes 408 in FIGS. 4A to 4D correspond to data lines 508 in FIG. 5, and the partitions 406 in FIGS. 4A to 4D correspond to partitions 506 in FIG. 5. An EL layer is formed between the data line 508 and the scan line 503, and a region 505 corresponds to one pixel.

Note that the scan lines 503 are electrically connected at their ends to connection wirings 509, and the connection wirings 509 are connected to an FPC 511b through an input terminal 510. The data lines 508 are connected to an FPC 511a through an input terminal 512.

For example, a surface where light is extracted may be provided with an optical film such as a polarizing plate, a circularly polarizing plate (including an elliptically polarizing plate), a retardation plate (a λ/4 plate or a λ/2 plate), a color filter, or an anti-reflection film. In addition, the surface where light is extracted or a surface of the various films may be subjected to treatment. For example, by forming a slightly uneven surface, reflected light diffuses to reduce glare.

Note that although FIG. 5 illustrates the example in which an IC chip including a driver circuit is not provided over the substrate, an IC chip may be mounted on the substrate. As a method for mounting an IC chip, a COG method, a wire bonding method, TCP, or the like can be used.

Figure 6A:
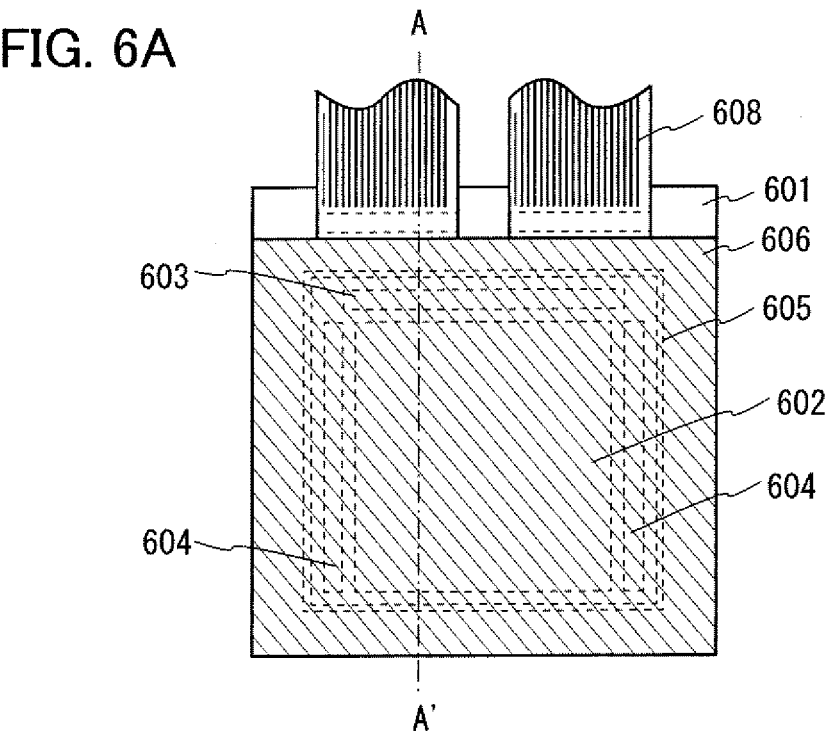
FIGS. 6A and 6B illustrate an active-matrix light-emitting device.
Figure 6B:
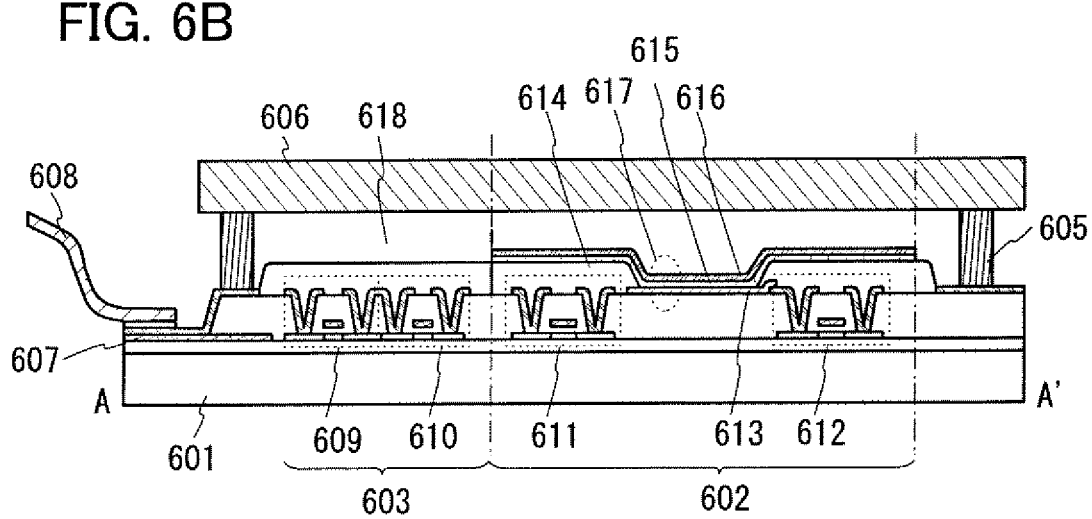

FIGS. 6A and 6B illustrate an example of an active-matrix light-emitting device.

FIG. 6A is a top view of the light-emitting device. FIG. 6B is a cross-sectional view taken along dashed line A-A' in FIG. 6A.

The active-matrix light-emitting device according to this embodiment includes a pixel portion 602, a driver circuit portion 603 (a source side driver circuit), and a driver circuit portion 604 (a gate side driver circuit) which are provided over an element substrate 601. The pixel portion 602, the driver circuit portion 603, and the driver circuit portion 604 are sealed with a sealant 605 between the element substrate 601 and a sealing substrate 606 (see FIG. 6A).

In addition, over the element substrate 601, a lead wiring 607 for connecting an external input terminal is provided. Note that here, an example is described in which a flexible printed circuit (FPC) is provided as the external input terminal. Although only the FPC 608 is illustrated in FIGS. 6A and 6B, this FPC may be provided with a printed wiring board (PWB). The term light-emitting device in this specification and the like includes not only a light-emitting device body but also a light-emitting device to which an FPC, a PWB, or the like is attached.

In the driver circuit portion 603, a CMOS circuit is formed by combining an n-channel TFT 609 and a p-channel TFT 610 (see FIG. 6B). It is needless to say that the circuit configuration is not limited to this example, and any of various circuits such as CMOS circuits, PMOS circuits, or NMOS circuits can be applied. In addition, although a driver circuit-integrated type where the driver circuit is formed over the substrate is described in this embodiment, the present invention is not to be construed as being limited to this structure. The driver circuit can be formed outside. Note that FIG. 6B exemplifies just the driver circuit portion 603 which is the source side driver circuit and the pixel portion 602.

The pixel portion 602 has plural pixels, each of which includes a switching TFT 611, a current control TFT 612, and an anode 613 which is electrically connected to an electrode (a source or drain electrode) of the current control TFT 612. Note that an insulator 614 is formed to cover the edge portion of the anode 613. Further, for the insulator 614, either a negative photosensitive material which becomes insoluble in an etchant by light or a positive photosensitive material which becomes soluble in an etchant by light can be used. Without limitation to an organic compound, an inorganic compound such as silicon oxide or silicon oxynitride can be used.

Preferably, an upper edge portion or a lower edge portion of the insulator 614 is a curved surface having a specific curvature radius. The curved surface contributes to improvement of coverage by a film which is to be formed over the insulator 614. For example, when a positive photosensitive acrylic resin is used as a material for the insulator 614, the upper edge portion thereof is preferably formed as a curved surface having a curvature radius of 0.2 μm to 3

Over the anode 613, an EL layer 615 and a cathode 616 are stacked. Here, by applying an ITO film to the anode 613 and applying a stack of a titanium nitride film and a film including aluminum as the main component or of a titanium nitride film, a film including aluminum as the main component, and a titanium nitride film to a wiring of the current control TFT 612 which is connected to the anode 613, favorable ohmic contact with the ITO film can be obtained and resistance of the wiring can be kept low. Note that although not illustrated here, the cathode 616 is electrically connected to the FPC 608 which is an external input terminal.

Note that in the EL layer 615, at least a light-emitting layer is provided, and in addition to the light-emitting layer, a hole-injection layer, a hole-transport layer, an electron-transport layer, an electron-injection layer, or the like may be provided. The anode 613, the EL layer 615, and the cathode 616 are stacked to form a light-emitting element 617.

In addition, although the cross-section in FIG. 6B illustrates one light-emitting element 617, a plurality of light-emitting elements is arranged in matrix in the pixel portion 602. Further, full-color display can be achieved by providing light-emitting elements that emit light of three colors (R, G, and B) as selected in the pixel portion 602. Color filters may be used in combination to perform full-color display.

The light-emitting element 617 is provided in a space 618 surrounded by the element substrate 601, the sealing substrate 606, and the sealant 605. Note that the space 618 may be filled with an inert gas (nitrogen, argon, or the like) or any other material such as the sealant 605.

As a material for the sealant 605, an epoxy resin is preferably used. It is desirable to use a material that allows permeation of moisture or oxygen as little as possible. As a material for the element substrate 601 or the sealing substrate 606, a plastic substrate formed of fiberglass-reinforced plastics (FRP), polyvinyl fluoride (PVF), polyester, acrylic, or the like can be used besides a glass substrate or a quartz substrate.

Note that the structure described in this embodiment can be combined with any structure described in the above embodiments, as appropriate.

(Embodiment 6)

In this embodiment, with reference to FIGS. 7A to 7E and FIG. 8, description is given of examples of a variety of electronic devices and lighting devices that are completed by using any light-emitting device which is one embodiment of the present invention.

Examples of the electronic devices to which the light-emitting device is applied include television sets (also referred to as televisions or television receivers), monitors of computers or the like, cameras such as digital cameras or digital video cameras, digital photo frames, cellular phones (also referred to as mobile phones or cellular phone sets), portable game consoles, portable information terminals, audio reproducing devices, large-sized game machines such as pachinko machines, and the like. Some specific examples of these electronic devices and a lighting device are illustrated in FIGS. 7A to 7E.

Figure 7A:
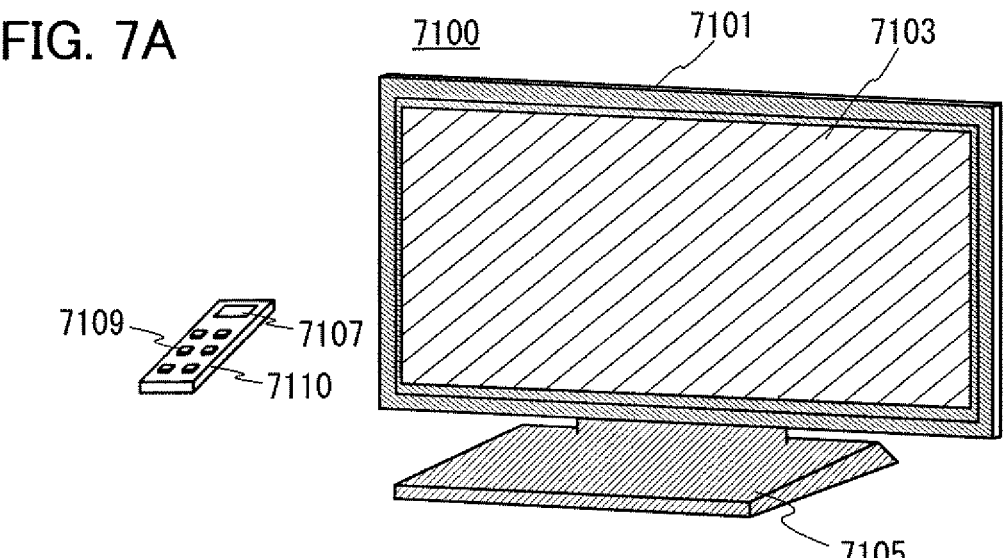
FIGS. 7A to 7E each illustrate an electronic device.

FIG. 7A illustrates an example of a television set 7100. In the television set 7100, a display portion 7103 is incorporated in a housing 7101. Images can be displayed by the display portion 7103, in which the light-emitting device can be used. Here, the housing 7101 is supported by a stand 7105.

The television set 7100 can be operated with an operation switch of the housing 7101 or a separate remote controller 7110. Channels and volume can be controlled with an operation key 7109 of the remote controller 7110 so that an image displayed on the display portion 7103 can be controlled. Furthermore, the remote controller 7110 may be provided with a display portion 7107 for displaying data output from the remote controller 7110.

Note that the television set 7100 is provided with a receiver, a modem, and the like. With the use of the receiver, general television broadcasting can be received. Moreover, when the television set is connected to a communication network with or without wires via the modem, one-way (from a sender to a receiver) or two-way (between a sender and a receiver or between receivers) information communication can be performed.

Figure 7B:
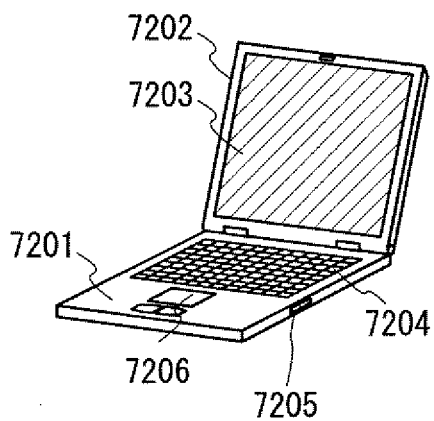

FIG. 7B illustrates an example of a computer. This computer includes a main body 7201, a housing 7202, a display portion 7203, a keyboard 7204, an external connecting port 7205, a pointing device 7206, and the like. Note that the computer is manufactured by using the light-emitting device for the display portion 7203.

Figure 7C:
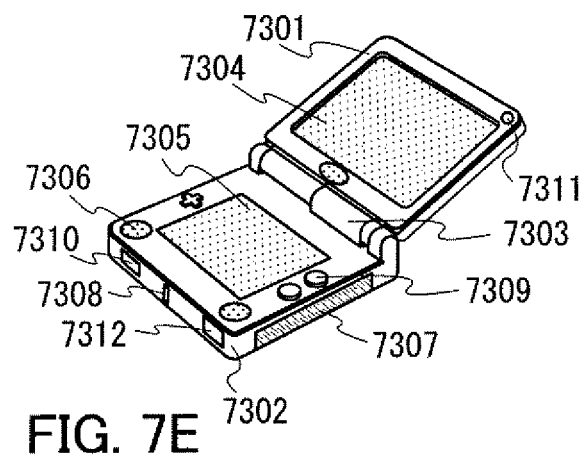

FIG. 7C illustrates an example of a portable amusement machine. This portable amusement machine includes two housings: a housing 7301 and a housing 7302. The housings 7301 and 7302 are connected with a connection portion 7303 so as to be opened and closed. A display portion 7304 and a display portion 7305 are incorporated in the housing 7301 and the housing 7302, respectively. In addition, the portable amusement machine illustrated in FIG. 7C includes a speaker portion 7306, a recording medium insertion portion 7307, an LED lamp 7308, an input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 7312), and the like. It is needless to say that the structure of the portable amusement machine is not limited to the above as long as the light-emitting device is used for at least either the display portion 7304 or the display portion 7305, or both. The portable amusement machine illustrated in FIG. 7C has a function of reading a program or data stored in a recording medium to display it on the display portion, and a function of sharing information with another portable amusement machine by wireless communication. The portable amusement machine illustrated in FIG. 7C can have any other various functions without limitation to the above.

Figure 7D:
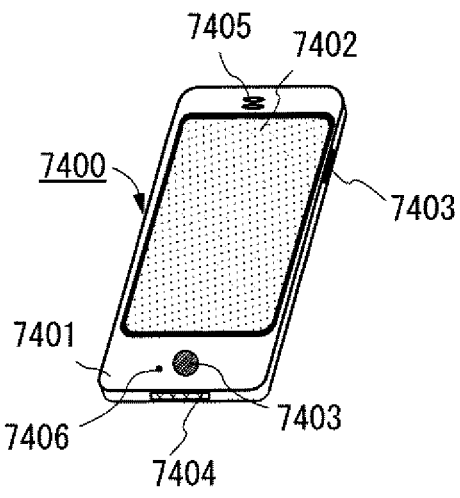

FIG. 7D illustrates an example of a cellular phone. A cellular phone 7400 is provided with a display portion 7402 incorporated in a housing 7401, operation buttons 7403, an external connection port 7404, a speaker 7405, a microphone 7406, and the like. Note that the light-emitting device is used for the display portion 7402 of the cellular phone 7400.

When the display portion 7402 of the cellular phone 7400 illustrated in FIG. 7D is touched with a finger or the like, data can be input into the cellular phone 7400. Furthermore, operations such as making calls and composing mails can be performed by touching the display portion 7402 with a finger or the like.

There are mainly three screen modes for the display portion 7402. The first mode is a display mode mainly for displaying images. The second mode is an input mode mainly for inputting data such as text. The third mode is a display-and-input mode in which two modes of the display mode and the input mode are combined.

For example, for operations such as making calls and composing mails, the display portion 7402 is set to a text input mode (second mode) mainly for inputting text so that text can be input. In this case, a keyboard or number buttons are preferably displayed on the display portion 7402.

By providing a detection device which includes a sensor for detecting inclination, such as a gyroscope or an acceleration sensor, inside the cellular phone 7400, the direction of the cellular phone 7400 is determined so that display on the screen of the display portion 7402 can be automatically switched.

In addition, the screen mode is switched by, for example, touching the display portion 7402 or operating the operation buttons 7403 of the housing 7401. Alternatively, the screen mode may be switched depending on the kind of images displayed on the display portion 7402. For example, when a signal of an image displayed on the display portion is of moving image data, the screen mode is switched to the display mode (first mode). When the signal is of text data, the screen mode is switched to the input mode (second mode).

Furthermore, when input by touching the display portion 7402 is not performed for a certain period, a controlling operation may be performed: for example, the screen mode may be switched from the input mode (first mode) to the display mode (second mode).

The display portion 7402 may function as an image sensor. For example, an image of a palm print, a fingerprint, or the like is taken by touching the display portion 7402 with the palm or the finger, whereby personal authentication can be performed. Furthermore, by providing a backlight or a sensing light source emitting a near-infrared light for the display portion, an image of a finger vein, a palm vein, or the like can also be taken.

Figure 7E:
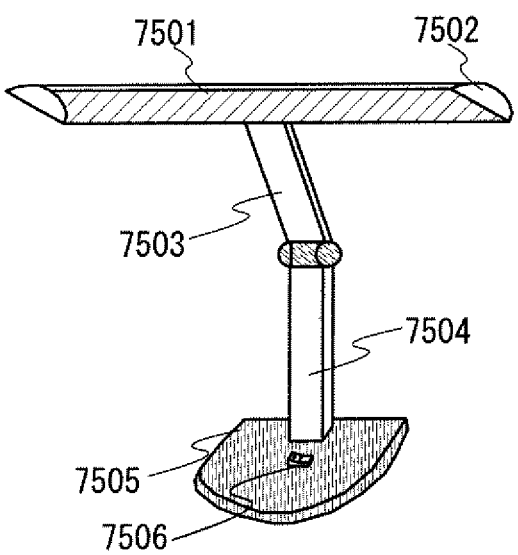

FIG. 7E illustrates a desk lamp including a lighting portion 7501, a shade 7502, an adjustable arm 7503, a support 7504, a base 7505, and a power supply 7506. The desk lamp is manufactured using the light-emitting device for the lighting portion 7501. Note that the term lighting device also includes ceiling lights, wall lights, and the like.

Figure 8:
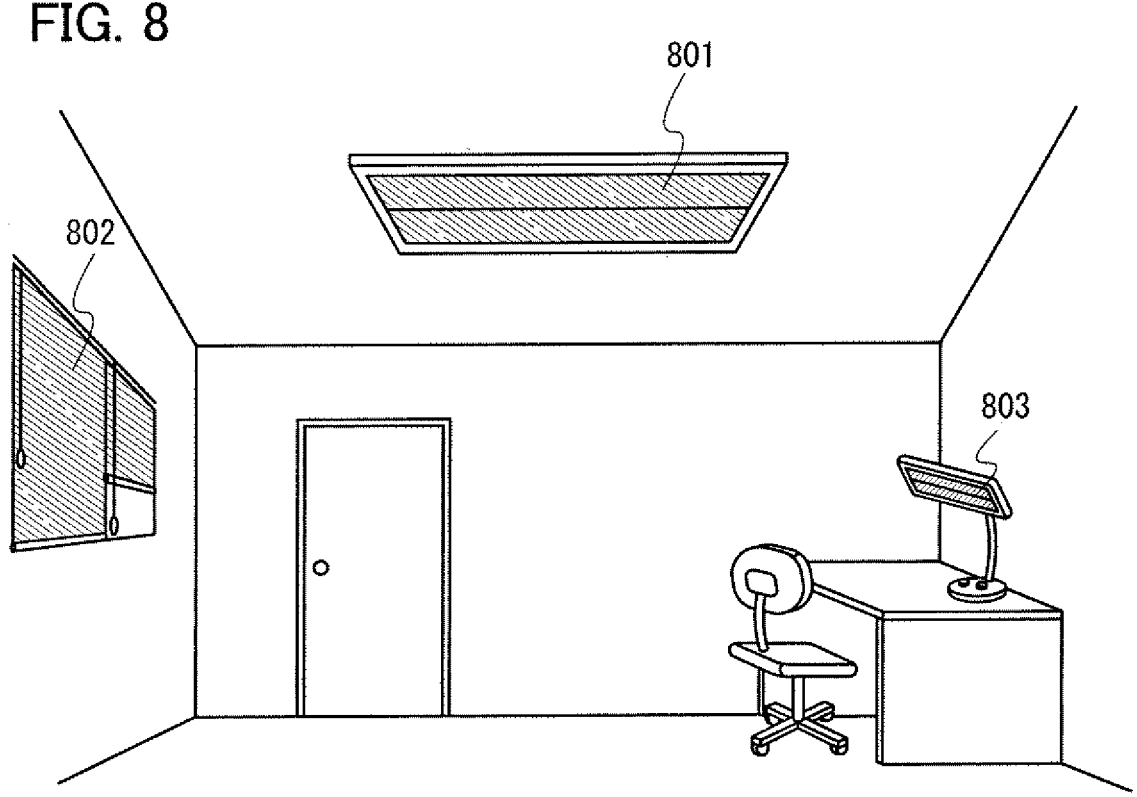
FIG. 8 illustrates lighting devices.

FIG. 8 illustrates an example in which the light-emitting device is used for an indoor lighting device 801. The light-emitting device enables an increase in emission area, and therefore can be used as a large-sized lighting device. Furthermore, the light-emitting device may be used as a lighting device 802 which can be rolled up. In addition, a desk lamp 803 illustrated in FIG. 7E may be used together in the room provided with the interior lighting device 801.

The electronic devices, lighting devices, and the like as illustrated above can be provided by application of the light-emitting device described in the above embodiment, for example. Thus, the applicable range of the light-emitting device is so wide that the light-emitting device can be applied to electronic devices in a variety of fields.

Note that the structure described in this embodiment can be combined with any structure described in the above embodiments, as appropriate.

EXAMPLE 1

In Example 1, a synthesis method of the derivative with a heteroaromatic ring according to an embodiment of the present invention, 4-(3,5-diphenyl-1H-1,2,4-triazol-1-yl) phenyl-9H-carbazole (abbreviation: CzTAZ(1H)) represented by Structural Formula (100) below will be specifically described.

[Chemical Formula 78]

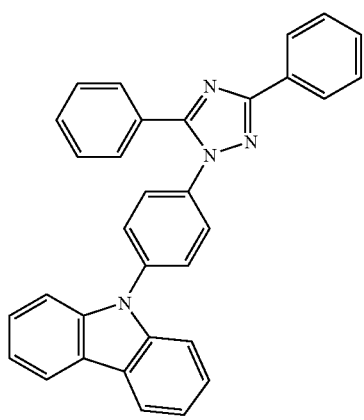

(100)

Synthesis of 4-(3,5-diphenyl-1H-1,2,4-triazol-1-yl) phenyl-9H-carbazole (abbreviation: CzTAZ(1H))

A synthesis scheme of 4-(3,5-diphenyl-1H-1,2,4-triazol-1-yl)phenyl-9H-carbazole (abbreviation: CzTAZ(1H)) is shown in (A-1).

[Chemical Formula 79]

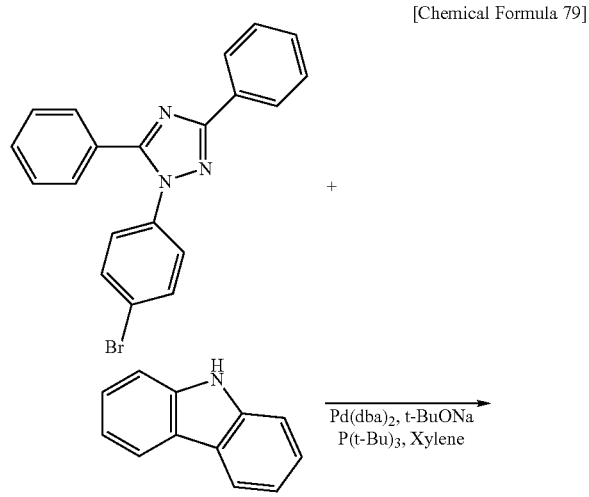

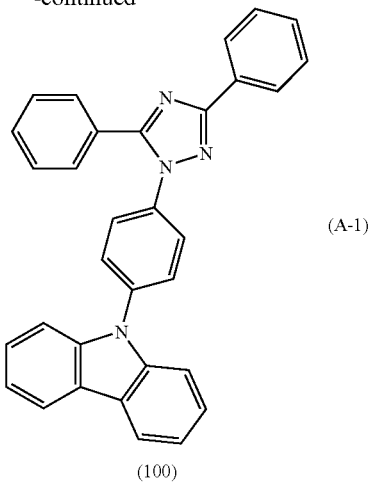

(A-1)

(100)

In a 100 mL three-necked flask were placed 1.5 g (4.0 mmol) of 1-(4-bromophenyl)-3,5-diphenyl-1H-1,2,4-triazole, 0.67 g (4.0 mmol) of 9H-carbazole, and 0.84 g (8.8 mmol) of sodium tert-butoxide, and the atmosphere in the flask was replaced with nitrogen. To this mixture were added 15 mL of xylene and 0.10 mL of a 10% hexane solution of tri(tert-butyl)phosphine. The pressure in the flask was reduced to degas this mixture, and then the atmosphere in the flask was replaced with nitrogen. To this mixture was added 0.069 g (0.12 mmol) of bis(dibenzylideneacetone)palladium (0). The resulting mixture was stirred under a nitrogen stream at 140° C. for 8 hours.

After that, water was added to this mixture and the mixture was stirred. Then, this mixture was suction filtered. The obtained filtrate was separated into an organic layer and an aqueous layer, and the organic layer was washed with water. After the washing, magnesium sulfate was added to the organic layer to dry the organic layer. After the drying, this mixture was subjected to suction filtration through Celite 545 (produced by Kishida Chemical Co., Ltd., Catalog No. 020-14815), whereby a filtrate was obtained. The obtained filtrate was concentrated to give an oily substance, which was purified by silica gel column chromatography. The column chromatography was performed first using toluene as a developing solvent and then using a mixed solvent of toluene and ethyl acetate (toluene:ethyl acetate=10:1) as a developing solvent. A compound obtained by concentrating the obtained fraction was purified by high performance liquid chromatography (HPLC). For the developing solvent, chloroform was used. The compound obtained by concentrating the obtained fraction was recrystallized with a mixed solvent of toluene and hexane, so that 0.84 g of a powdery white solid, which was the object of the synthesis, was obtained at a yield of 46%.

Sublimation purification of 0.84 g of the obtained white solid was performed by a train sublimation method. The sublimation purification was performed under a reduced pressure of 2.6 Pa, with an argon flow rate of 5 mL/min, at 220° C. for 16 hours. 0.74 g of the white solid was obtained at a yield of 88%.

A compound obtained through the above step was measured by a nuclear magnetic resonance method (NMR). The measurement data are shown below. $^1$H NMR (CDCl$_3$, 300 MHz): δ=7.28-7.34 (m, 2H), 7.41-7.53 (m, 10H), 7.63-7.69 (m, 6H), 8.14 (d, J=7.8 Hz, 2H), 8.28 (d, J=7.8 Hz, 2H).

Figure 10A:
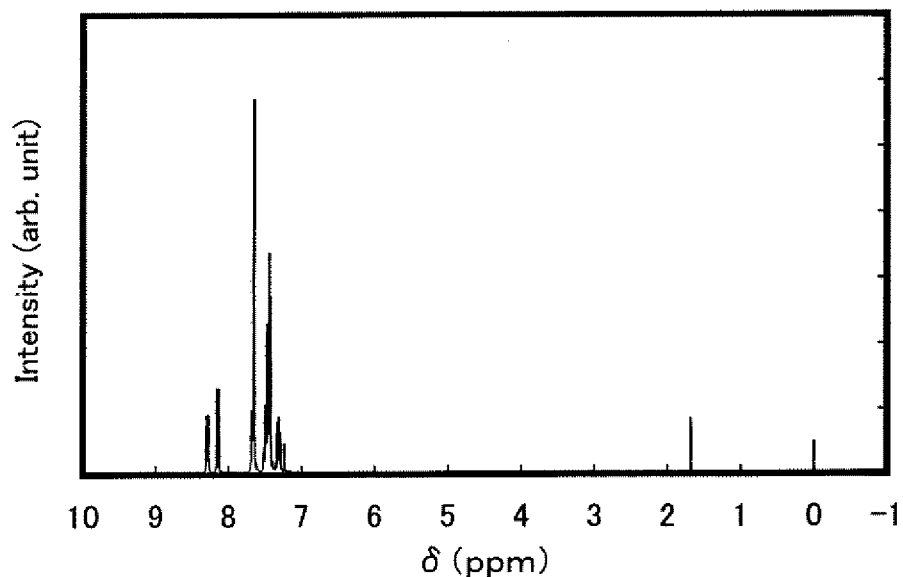
FIGS. 10A and 10B show NMR charts of CzTAZ(1H) (abbreviation).
Figure 10B:
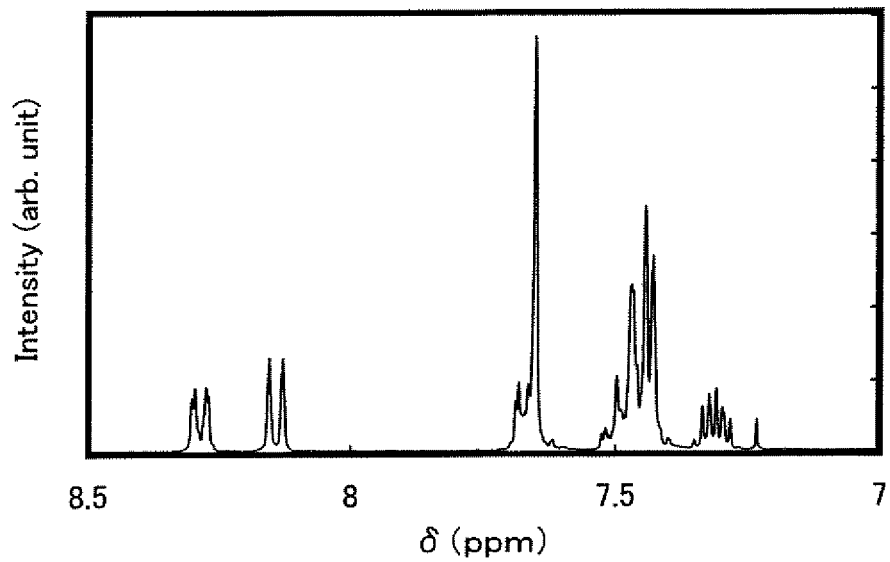

In addition, ¹H NMR charts are shown in FIGS. 10A and 10B. Note that FIG. 10B is a chart in which the range of 7.0 ppm to 8.5 ppm in FIG. 10A is expanded. It was found from the measurement result that the derivative with a heteroaromatic ring of the present invention, 4-(3,5-diphenyl-1H-1,2,4-triazol-1-yl)phenyl-9H-carbazole (abbreviation: CzTAZ (1H)) represented by Structural Formula (100) above was obtained.

Figure 11A:
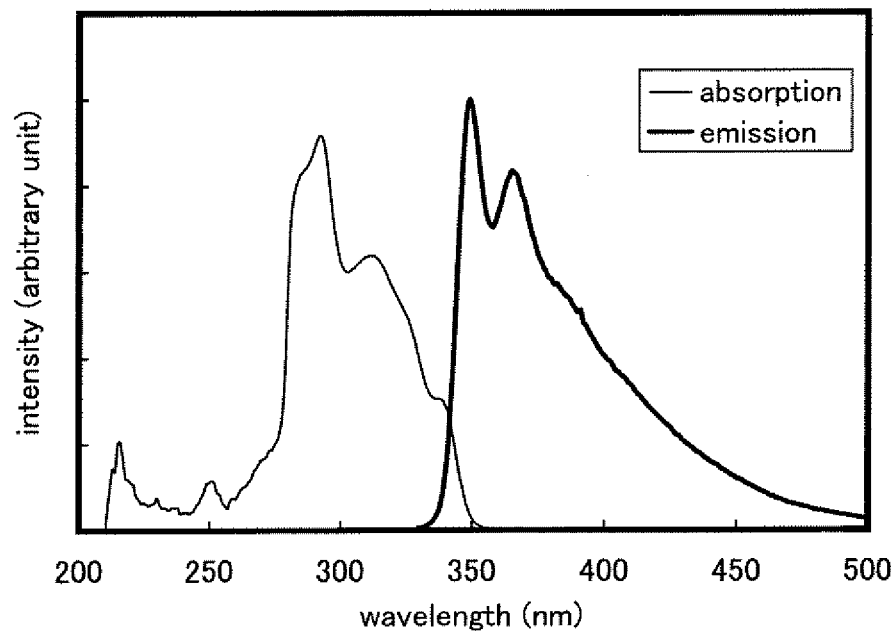
FIGS. 11A and 11B each show an absorption spectrum and an emission spectrum of CzTAZ(1H) (abbreviation).
Figure 11B:
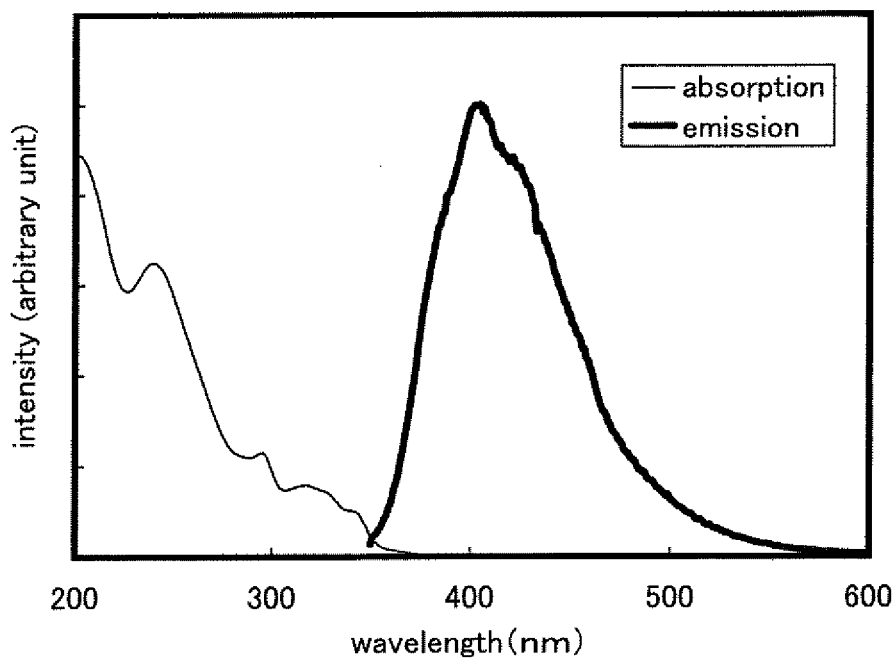

FIG. 11A shows an absorption spectrum and an emission spectrum of a toluene solution of CzTAZ(1H) (abbreviation) and FIG. 11B shows an absorption spectrum and an emission spectrum of a thin film of CzTAZ(1H) (abbreviation). An ultraviolet-visible spectrophotometer (V-550, manufactured by Japan Spectroscopy Corporation) was used for the measurement. The absorption spectrum of the toluene solution of CzTAZ(1H) (abbreviation) was obtained by subtracting the absorption spectra of quartz and toluene from the absorption spectrum of the toluene solution in a quartz cell. In addition, the absorption spectrum of the thin film of CzTAZ(1H) (abbreviation) was obtained by subtracting the absorption spectrum of quartz from the absorption spectrum of a sample formed by evaporating CzTAZ(1H) (abbreviation) to a quartz substrate.

In FIGS. 11A and 11B, the horizontal axis indicates the wavelength (nm) and the vertical axis indicates the absorption intensity (arbitrary unit). With the toluene solution, an absorption peak was observed at around 336 nm. With the thin film, an absorption peak was observed at around 341 nm. An emission spectrum of the toluene solution (excitation wavelength: 327 nm) of CzTAZ(1H) (abbreviation) is shown in FIG. 11A. In addition, an emission spectrum of the thin film (excitation wavelength: 340 nm) of CzTAZ(1H) (abbreviation) is shown in FIG. 11B. In FIGS. 11A and 11B, the horizontal axis indicates the wavelength (nm) and the vertical axis indicates the light emission intensity (arbitrary unit). The emission wavelengths were 349 nm, 367 nm, and 386 nm (excitation wavelength: 327 nm) in the case of the toluene solution and 403 nm (excitation wavelength: 340 nm) in the case of the thin film.

Further, by measurement with a photoelectron spectrometer (AC-2, manufactured by Riken Keiki, Co., Ltd.) in the atmosphere, the ionization potential of the thin film of CzTAZ (1H) (abbreviation) was found to be 5.90 eV. As a result, it was found that the HOMO level was −5.90 eV. Furthermore, the absorption edge was obtained by Tauc plot assuming direct transition with the absorption spectrum data of the thin film of CzTAZ(1H) (abbreviation). When the absorption edge was estimated as an optical energy gap, the energy gap was 3.53 eV. From the obtained values of the energy gap and the HOMO level, the LUMO level was −2.37 eV.

In addition, the optimal molecular structure of CzTAZ(1H) in the ground state was calculated using the density functional theory (DFT). In the DFT, the total energy is represented as the sum of potential energy, electrostatic energy between electrons, electronic kinetic energy, and exchange-correlation energy including all the complicated interactions between electrons. Also in the DFT, an exchange-correlation interaction is approximated by a functional (a function of another function) of one electron potential represented in terms of electron density to enable highly accurate calculations. Here, B3LYP which was a hybrid functional was used to specify the weight of each parameter related to exchange-correlation energy. In addition, as a basis function, 6-311 (a basis function of a triple-split valence basis set using three contraction functions for each valence orbital) was applied to all the atoms. By the above basis function, for example, orbits of 1s to 3s are considered in the case of hydrogen atoms while orbits of 1s to 4s and 2p to 4p are considered in the case of carbon atoms. Furthermore, to improve calculation accuracy, the p function and the d function as polarization basis sets were added to hydrogen atoms and atoms other than hydrogen atoms, respectively.

Note that Gaussian 03 was used as a quantum chemistry computational program. A high performance computer (manufactured by SGI Japan, Ltd., Altix 4700) was used for the calculations.

FIGS. 22A and 22B are visualization views of the highest occupied molecular orbital (HOMO) and the lowest unoccupied molecular orbital (LUMO) in the optimal molecular structure of CzTAZ(1H) obtained by the calculations, by Gaussview 4.1. FIGS. 22A and 22B show the highest occupied molecular orbital (HOMO) and the lowest unoccupied molecular orbital (LUMO), respectively. The spheres in the drawings represent atoms forming CzTAZ(1H) and cloud-like objects around the atoms represent the highest occupied molecular orbital (HOMO) or the lowest unoccupied molecular orbital (LUMO).

It is found from FIGS. 22A and 22B that in CzTAZ(1H), the highest occupied molecular orbital exist around carbazole and the contribution of a carbazolyl group to a hole-transport property of CzTAZ(1H) is large. Since the lowest unoccupied molecular orbital exist around triazole, it is found that the contribution of a triazole group to an electron-transport property of CzTAZ(1H) is large. Accordingly, since a triazole skeleton which is a heteroaromatic ring having an electron-transport property and a carbazole skeleton having a hole-transport property are introduced into a molecule in CzTAZ (1H), it is found that CzTAZ(1H) is a bipolar material having an electron-transport and hole-transport properties.

EXAMPLE 2

In Example 2, a synthesis method of the derivative with a heteroaromatic ring according to an embodiment of the present invention, 9-[4-(3,5-diphenyl-1H-pyrazol-1-yl)phenyl]-9H-carbazole (abbreviation: CzPz) represented by Structural Formula (184) will be specifically described.

[Chemical Formula 80]

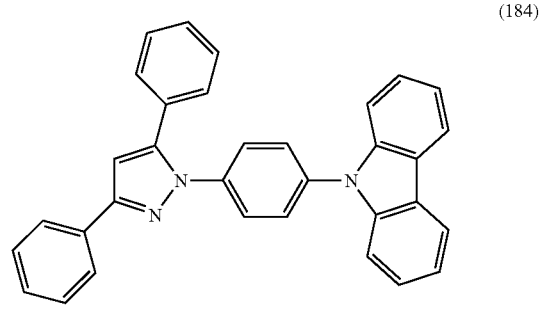

(184)

Synthesis of 9-[4-(3,5-diphenyl-1H-pyrazol-1-yl) phenyl]-9H-carbazole (abbreviation: CzPz)

A synthesis scheme of 9-[4-(3,5-diphenyl-1H-pyrazol-1-yl)phenyl]-9H-carbazole (abbreviation: CzPz) is shown in (B-1).

[Chemical Formula 81]

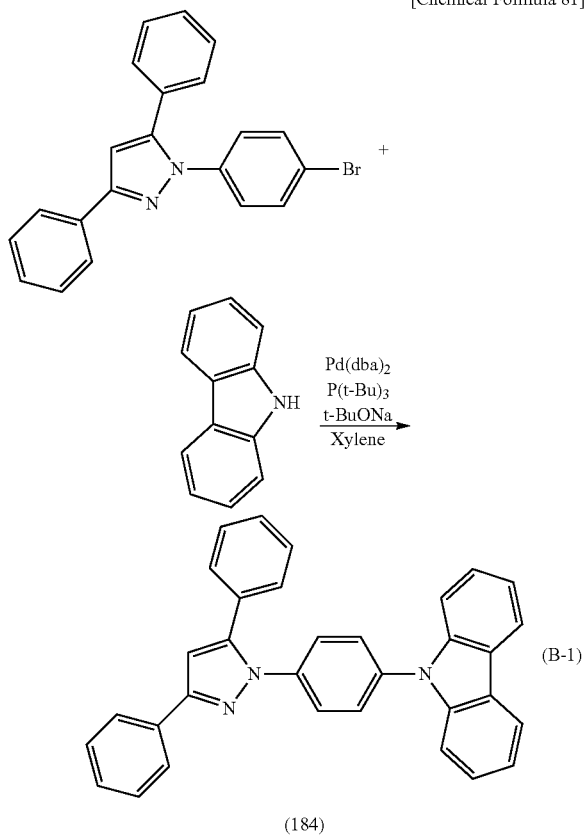

In a 100 mL three-necked flask were placed 1.5 g (4.0 mmol) of 1(4-bromophenyl)-3,5-diphenyl-1H-pyrazol, 0.70 g (4.2 mmol) of 9H-carbazole, and 0.80 g (8.2 mmol) of sodium tert-butoxide, and the atmosphere in the flask was replaced with nitrogen. To this mixture was added 40 mL of xylene. The mixture was degassed by being stirred under reduced pressure, and then to this mixture were added 0.10 mL of a 10% hexane solution of tri(tert-butyl)phosphine and 50 mg (0.086 mmol) of bis(dibenzylideneacetone)palladium (0). The resulting mixture was stirred under a nitrogen stream at 140° C. for 6 hours. After a certain time, water was added to the mixture, and an aqueous layer was extracted with toluene. The obtained extracted solution and the organic layer were combined, washed with water, a saturated aqueous solution of sodium hydrogen carbonate, and saturated saline, and dried with magnesium sulfate. The filtrate obtained by gravity filtering the obtained mixture was concentrated to give an oily substance. The obtained oily substance was purified by silica gel column chromatography (a developing solvent was a mixed solvent of toluene:hexane=1:1) to give an oily substance. To the oily substance was added hexane, and suction filtration was performed on a precipitated solid, so that 1.3 g of a white powder, which was the object of the synthesis, was obtained at a yield of 68%.

Sublimation purification of 1.2 g of the obtained solid was performed by a train sublimation method. The sublimation purification was performed under a reduced pressure of 10 Pa, with an argon flow rate of 5 mL/min, at 220° C. for 16 hours. 1.1 g of the solid was obtained at a yield of 88%.

A compound obtained through the above step was measured by a nuclear magnetic resonance method (NMR). The measurement data are shown below. $^1$H NMR (CDCl$_3$, 300 MHz): δ=6.89 (s, 1H), 7.27-7.50 (m, 14H), 7.55-7.64 (m, 4H), 7.97 (d, J=6.9 Hz, 2H), 8.15 (d, J=7.8 Hz, 2H).

Figure 12A:
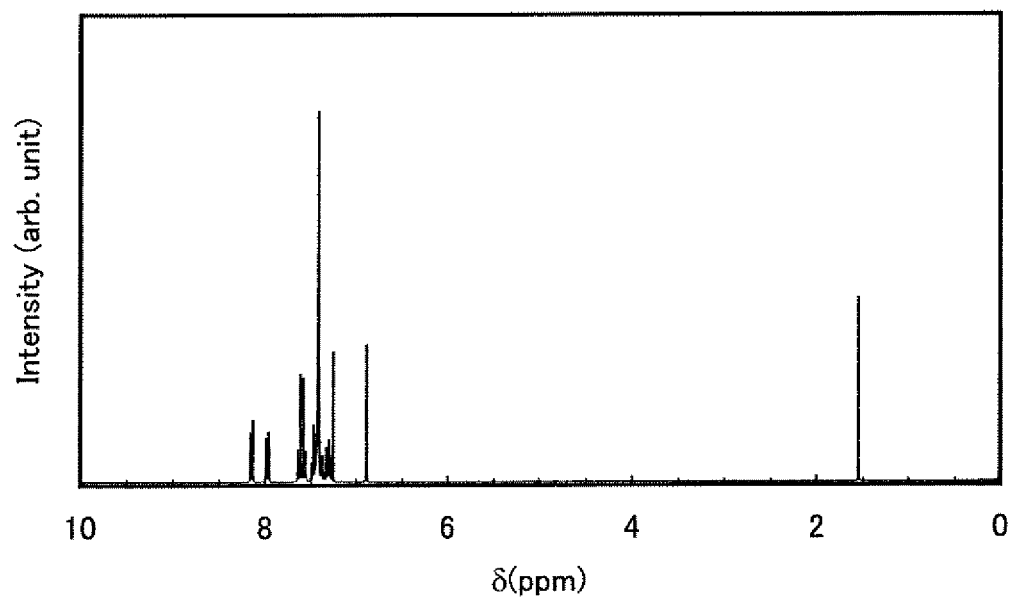
FIGS. 12A and 12B show NMR charts of CzPz (abbreviation).
Figure 12B:
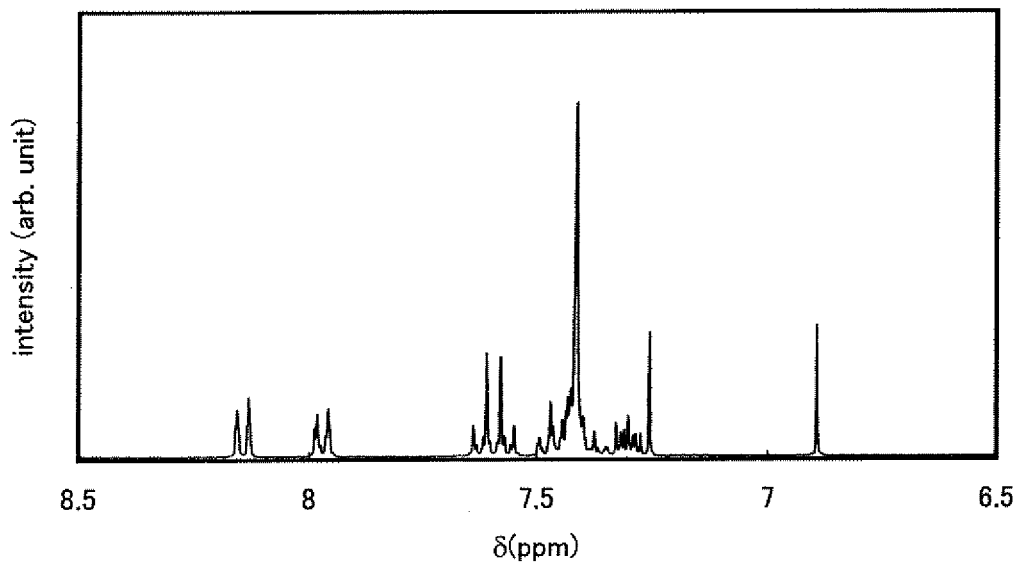

In addition, $^1$H NMR charts are shown in FIGS. 12A and 12B. Note that FIG. 12B is a chart in which the range of 6.5 ppm to 8.5 ppm in FIG. 12A is expanded. It was found from the measurement result that the derivative with a heteroaromatic ring of the present invention, 9-[4-(3,5-diphenyl-1H-pyrazol-1-yl)phenyl]-9H-carbazole (abbreviation: CzPz) represented by Structural Formula (184) above was obtained.

Figure 13A:
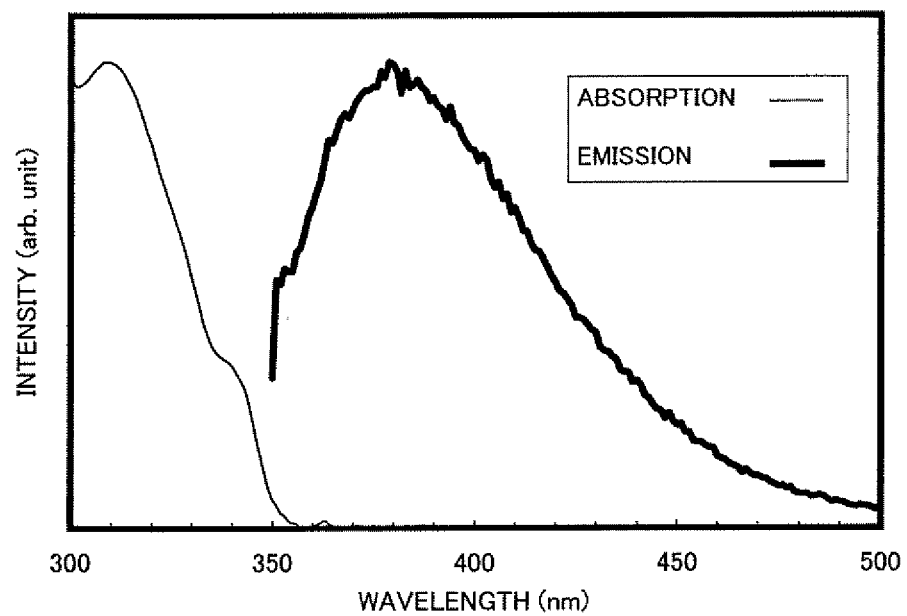
FIGS. 13A and 13B each show an absorption spectrum and an emission spectrum of CzPz (abbreviation).
Figure 13B:
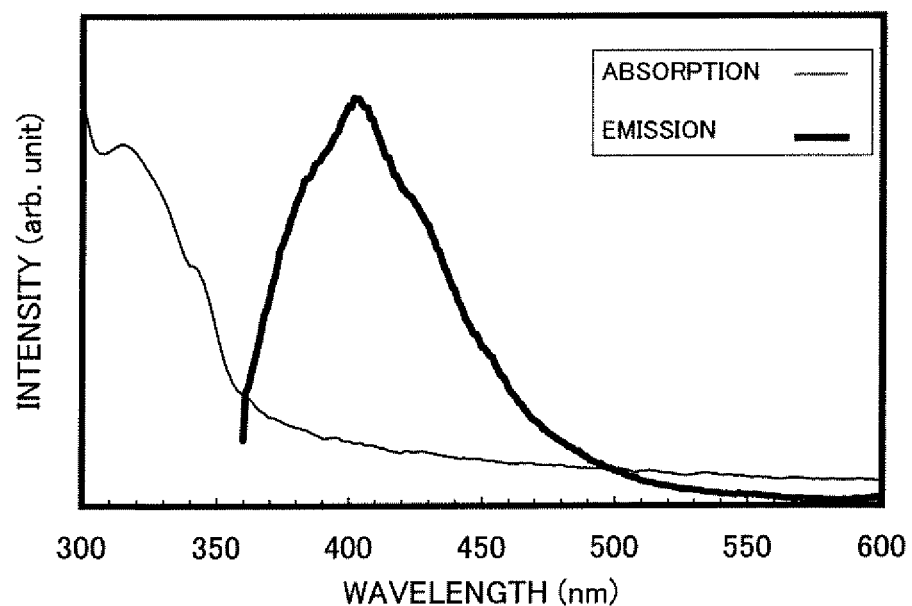

FIG. 13A shows an absorption spectrum and an emission spectrum of a toluene solution of CzPz (abbreviation) and FIG. 13B shows an absorption spectrum and an emission spectrum of a thin film of CzPz (abbreviation). An ultraviolet-visible spectrophotometer (V-550, manufactured by Japan Spectroscopy Corporation) was used for the measurement. The absorption spectrum of the toluene solution of CzPz (abbreviation) was obtained by subtracting the absorption spectra of quartz and toluene from the absorption spectrum of the toluene solution in a quartz cell. In addition, the absorption spectrum of the thin film of CzPz (abbreviation) was obtained by subtracting the absorption spectrum of quartz from the absorption spectrum of a sample formed by evaporating CzPz (abbreviation) to a quartz substrate.

In FIGS. 13A and 13B, the horizontal axis indicates the wavelength (nm) and the vertical axis indicates the absorption intensity (arbitrary unit). With the toluene solution, an absorption peak was observed at around 339 nm. With the thin film, an absorption peak was observed at around 341 nm. An emission spectrum of the toluene solution (excitation wavelength: 340 nm) of CzPz (abbreviation) is shown in FIG. 13A. In addition, an emission spectrum of the thin film (excitation wavelength: 344 nm) of CzPz (abbreviation) is shown in FIG. 13B. In FIGS. 13A and 13B, the horizontal axis indicates the wavelength (nm) and the vertical axis indicates the light emission intensity (arbitrary unit). The maximum emission wavelengths were 379 nm (excitation wavelength: 340 nm) in the case of the toluene solution and 403 nm (excitation wavelength: 344 nm) in the case of the thin film.

Further, by measurement with a photoelectron spectrometer (AC-2, manufactured by Riken Keiki, Co., Ltd.) in the atmosphere, the ionization potential of the thin film of CzPz (abbreviation) was found to be 5.64 eV. As a result, it was found that the HOMO level was −5.64 eV. Furthermore, the absorption edge was obtained by Tauc plot assuming direct transition with the absorption spectrum data of the thin film of CzPz (abbreviation). When the absorption edge was estimated as an optical energy gap, the energy gap was 3.47 eV. From the obtained values of the energy gap and the HOMO level, the LUMO level was −2.17 eV.

In addition, the optimal molecular structure of CzPz in the ground state was calculated using a manner similar to that of CzTAZ(1H).

FIGS. 23A and 23B are visualization views of the highest occupied molecular orbital (HOMO) and the lowest unoccupied molecular orbital (LUMO) in the optimal molecular structure of CzPz obtained by the calculations, by Gaussview 4.1. FIGS. 23A and 23B show the highest occupied molecular orbital (HOMO) and the lowest unoccupied molecular orbital (LUMO), respectively. The spheres in the drawings represent atoms forming CzPz, and cloud-like objects around the atoms represent the highest occupied molecular orbital (HOMO) or the lowest unoccupied molecular orbital (LUMO).

It is found from FIGS. 23A and 23B that in CzPz, the highest occupied molecular orbital exist around carbazole and the contribution of a carbazolyl group to a hole-transport property of CzPz is large. Since the lowest unoccupied molecular orbital exist around pyrazole, it is found that the contribution of a pyrazolyl group to an electron-transport property of CzPz is large. Accordingly, since a pyrazole skeleton which is a heteroaromatic ring having an electron-transport property and a carbazole skeleton having a hole-transport property are introduced into a molecule in CzPz, it is found that CzPz is a bipolar material having an electron-transport and hole-transport properties.

EXAMPLE 3

In this example, description is provided of a method for forming a light-emitting element including any of the derivatives with a heteroaromatic ring which is described in Embodiment 1 as a host material in a light-emitting layer and of results of the element characteristics measurements. Specifically, Light-Emitting Element 1 formed using 4-(3,5-diphenyl-1H-1,2,4-triazol-1-yl)phenyl-9H-carbazole (abbreviation: CzTAZ(1H)), which is described in Example 1 will be described.

Figure 9:
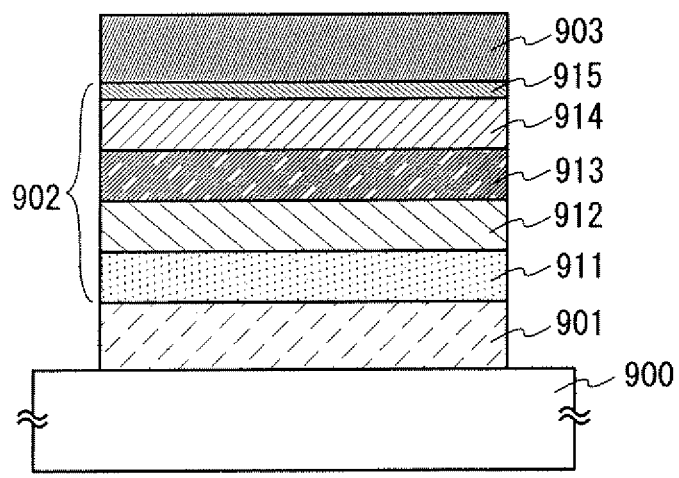
FIG. 9 illustrates a light-emitting element.

Note that FIG. 9 illustrates a structure of each light-emitting element of this example, in which a third layer 913 which is a light-emitting layer is formed using one of the derivatives with a heteroaromatic ring of the present invention. Structural Formulae of organic compounds used in this example are illustrated below.

[Chemical Formula 82]

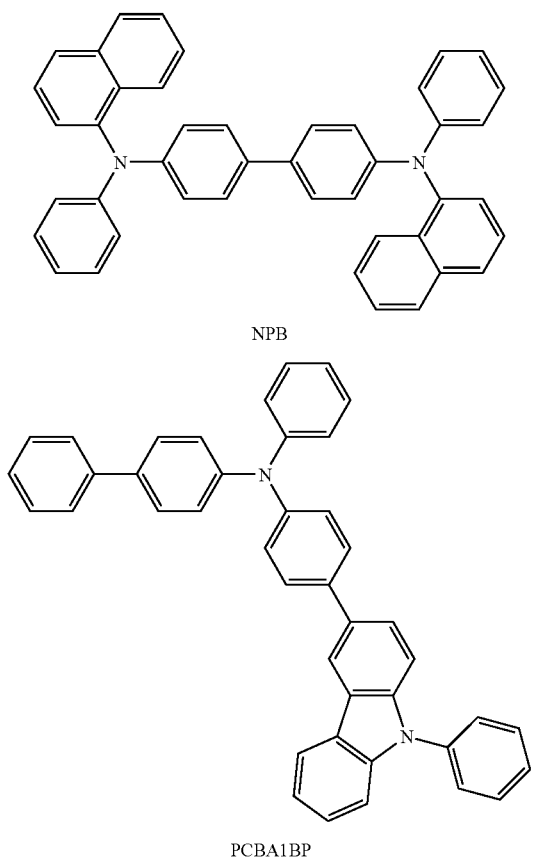

NPB

PCBA1BP

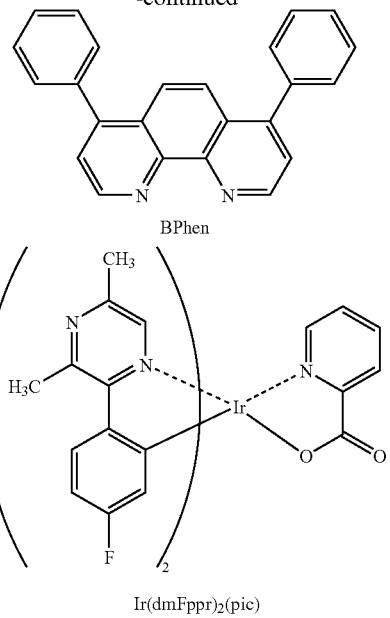

BPhen

Ir(dmFppr)$_2$(pic)

First, indium oxide-tin oxide containing silicon oxide was deposited on a substrate 900 which was a glass substrate by a sputtering method to form a first electrode 901. Note that the thickness of the first electrode 901 was set to 110 nm and the area of the electrode was set to 2 mm×2 mm.

Next, an EL layer 902 including a stack of a plurality of layers was formed over the first electrode 901. In this example, the EL layer 902 has a structure in which a first layer 911 which is a hole-injection layer, a second layer 912 which is a hole-transport layer, the third layer 913 which is a light-emitting layer, a fourth layer 914 which is an electron-transport layer, and a fifth layer 915 which is an electron-injection layer are stacked in that order.

The substrate 900 provided with the first electrode 901 was fixed on a substrate holder that was provided in a vacuum evaporation apparatus so that a surface on which the first electrode 901 was formed faced downward. The pressure in the vacuum evaporation apparatus was reduced to about $10^{-4}$ Pa. Then, on the first electrode 901, 4,4'-bis[N-(1-naphthyl)-N-phenylamino]biphenyl (abbreviation: NPB) and molybdenum(VI) oxide were co-evaporated to form the first layer 911 which was a hole-injection layer. The thickness of the first layer 911 was set to 50 nm, and the evaporation rate was controlled so that the weight ratio of NPB to molybdenum (VI) oxide was 4:2 (=NPB:molybdenum oxide). Note that the co-evaporation method refers to an evaporation method by which evaporation is performed from a plurality of evaporation sources in one treatment chamber simultaneously.

Next, a 10-nm-thick film of a hole-transport material was formed on the first layer 911 by an evaporation method with resistance heating to form the second layer 912 which was a hole-transport layer. Note that for the second layer 912, 4-phenyl-4'-(9-pheny-9H-carbazole-3-yl)triphenylamine (abbreviation: PCBA1BP) was used.

Next, the third layer 913 which was a light-emitting layer was formed on the second layer 912 by an evaporation method with resistance heating. As the third layer 913 of Light-Emitting Element 1, 4-(3,5-diphenyl-1H-1,2,4-triazol-1-yl)phenyl-9H-carbazole (abbreviation: CzTAZ(1H)), 4-phenyl-4'-(9-pheny-9H-carbazole-3-yl)triphenylamine (abbreviation: PCBA1BP), and bis{2-(4-fluorophenyl)-3,5- dimethylpyrazinato}(picolinato)iridium(III) (abbreviation: Ir(dmFppr)$_2$(pic)) were co-evaporated to form a 40-nm-thick film. Here, the evaporation rate was controlled so that the weight ratio of CzTAZ(1H) to PCBA1BP and Ir(dmFppr)$_2$(pic)) was 1:0.2:0.1 (=CzTAZ(1H):PCBA1BP:Ir(dmFppr)$_2$(pic)).

Further, on the third layer 913, a 10-nm-thick film of 4-(3,5-diphenyl-1H-1,2,4-triazol-1-yl)phenyl-9H-carbazole (abbreviation: CzTAZ(1H)) and, thereon, a 20-nm-thick film of bathophenanthroline (abbreviation: BPhen) were formed by an evaporation method with resistive heating to form the fourth layer 914 which was an electron-transport layer.

On the fourth layer 914, a 1-nm-thick film of lithium fluoride (LiF) was formed as the fifth layer 915 which was an electron-injection layer.

Lastly, a 200-nm-thick film of aluminum was formed by an evaporation method with resistance heating to form the second electrode 903. In this manner, Light-Emitting Element 1 was formed.

The thus obtained Light-Emitting Element 1 was sealed in a glove box with a nitrogen atmosphere so as not to be exposed to air. Then, operation characteristics of Light-Emitting Element 1 were measured. Note that the measurements were carried out at room temperature (in an atmosphere kept at 25° C.).

Figure 14:
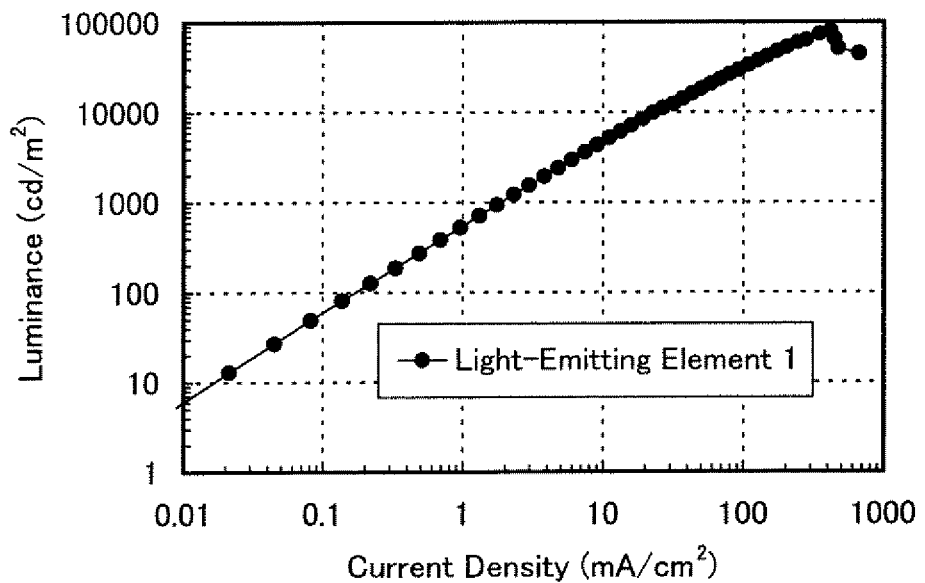
FIG. 14 shows current density-luminance characteristics of Light-Emitting Element 1.
Figure 15:
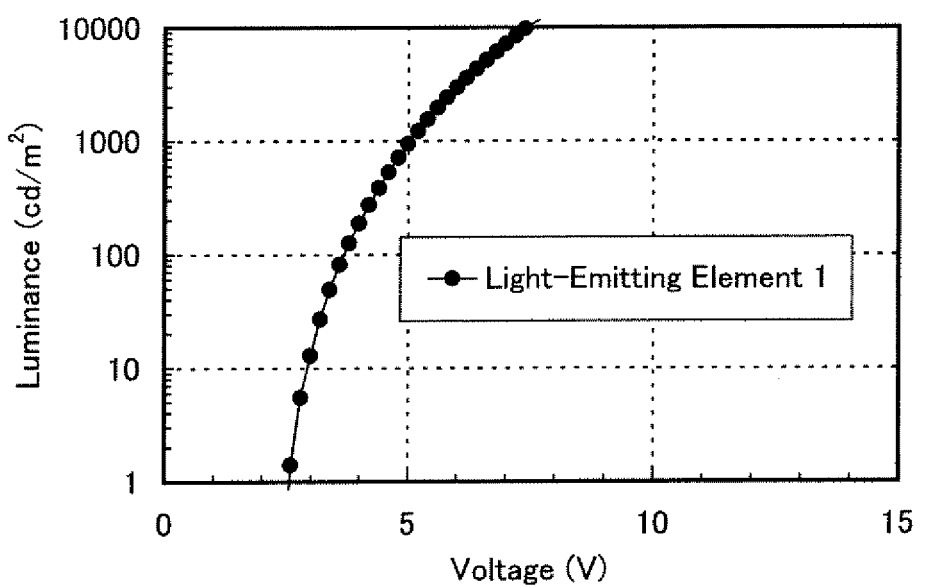
FIG. 15 shows voltage-luminance characteristics of Light-Emitting Element 1.
Figure 16:
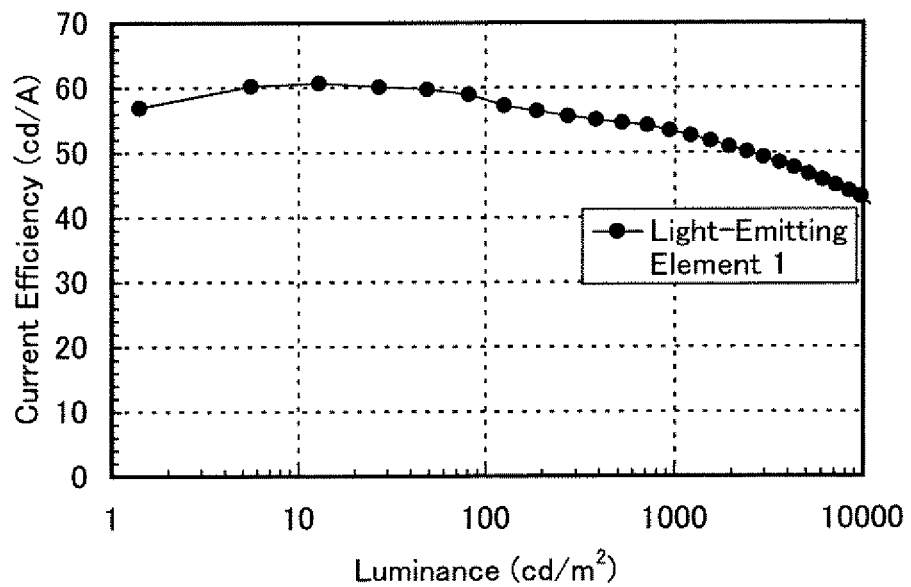
FIG. 16 shows luminance-current efficiency characteristics of Light-Emitting Element 1.

FIG. 14 shows current density-luminance characteristics, FIG. 15 shows voltage-luminance characteristics, and FIG. 16 shows luminance-current efficiency characteristics of Light-emitting Element 1. In FIG. 14, the vertical axis represents luminance (cd/m$^2$) and the horizontal axis represents current density (mA/cm$^2$). In FIG. 15, the vertical axis represents luminance (cd/m$^2$) and the horizontal axis represents voltage (V). In FIG. 16, the vertical axis represents current efficiency (cd/A) and the horizontal axis represents luminance (cd/m$^2$).

Note that in Light-Emitting Element 1, the voltage needed to obtain luminance of 940 cd/m$^2$ was 5.0 V. In addition, the current efficiency and the quantum efficiency were 53.4 cd/A and 14.9%, respectively. Thus, it is found that the light-emitting element using the derivative with a heteroaromatic ring according to an embodiment of the present invention has high efficiency.

Figure 17:
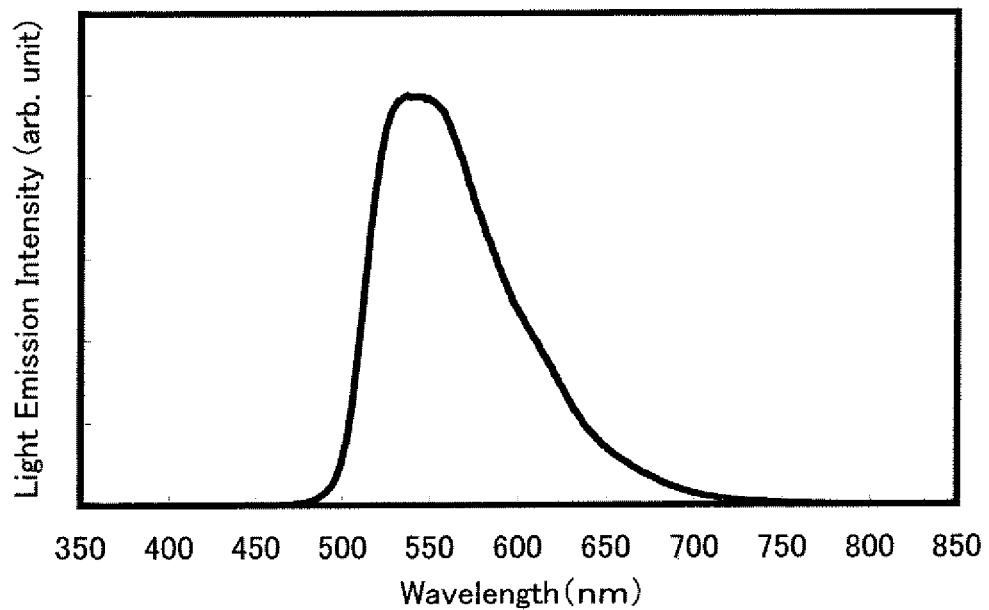
FIG. 17 shows an emission spectrum of Light-Emitting Element 1.

An emission spectrum of Light-Emitting Element 1 is shown in FIG. 17. As shown in FIG. 17, in Light-Emitting Element 1, an emission wavelength derived from Ir(dmFppr)$_2$(pic) (abbreviation) which was a guest material was observed, whereas an emission wavelength derived from CzTAZ(1H) (abbreviation), which was the derivative with a heteroaromatic ring according to an embodiment of the present invention and was a host material, was not observed. Therefore, it is confirmed that the derivative with a heteroaromatic ring according to an embodiment of the present invention serves as the host material having a bipolar property for the light-emitting layer of the light-emitting element.

EXAMPLE 4

In this example, description is provided of a method for forming a light-emitting element including any of the derivatives with a heteroaromatic ring which is described in Embodiment 1 as a host material in a light-emitting layer and of results of the element characteristics measurements. Specifically, Light-Emitting Element 2 formed using 9-[4-(3,5-diphenyl-1H-pyrazol-1-yl)phenyl]-9H-carbazole (abbreviation: CzPz), which is described in Example 2, will be described.

Note that a structure of the light-emitting element of this example is illustrated in FIG. 9, in which the third layer 913 which is a light-emitting layer is formed using one of the derivatives with a heteroaromatic ring according to an embodiment of the present invention described above.

First, indium oxide-tin oxide containing silicon oxide was deposited on the substrate 900 which was a glass substrate by a sputtering method to form the first electrode 901. Note that the thickness of the first electrode 901 was set to 110 nm and the area of the electrode was set to 2 mm×2 mm.

Next, the EL layer 902 including a stack of a plurality of layers was formed over the first electrode 901. In this example, the EL layer 902 has a structure in which the first layer 911 which is a hole-injection layer, the second layer 912 which is a hole-transport layer, the third layer 913 which is a light-emitting layer, the fourth layer 914 which is an electron-transport layer, and the fifth layer 915 which is an electron-injection layer are stacked in that order.

The substrate 900 provided with the first electrode 901 was fixed on a substrate holder that was provided in a vacuum evaporation apparatus so that a surface on which the first electrode 901 was formed faced downward. The pressure in the vacuum evaporation apparatus was reduced to about 10$^{-4}$ Pa. Then, on the first electrode 901, 4,4'-bis[N-(1-naphtyl)-N-phenylamino]biphenyl (abbreviation: NPB) and molybdenum(VI) oxide were co-evaporated to form the first layer 911 which was a hole-injection layer. The thickness of the first layer 911 was set to 50 nm, and the evaporation rate was controlled so that the weight ratio of NPB to molybdenum (VI) oxide was 4:2 (=NPB:molybdenum oxide). Note that the co-evaporation method refers to an evaporation method by which evaporation is performed from a plurality of evaporation sources in one treatment chamber simultaneously.

Next, a 10-nm-thick film of a hole-transport material was formed on the first layer 911 by an evaporation method with resistance heating to form the second layer 912 which was a hole-transport layer. Note that for the second layer 912, 4-phenyl-4'-(9-phenyl-9H-carbazol-3-yl)triphenylamine (abbreviation: PCBA1BP) was used.

Next, the third layer 913 which was a light-emitting layer was formed on the second layer 912 by an evaporation method with resistance heating. As the third layer 913 of Light-Emitting Element 2, 9-[4-(3,5-diphenyl-1H-pyrazol-1-yl)phenyl]-9H-carbazole (abbreviation: CzPz), 4-phenyl-4'-(9-phenyl-9H-carbazol-3-yl)triphenylamine (abbreviation: PCBA1BP), and bis{2-(4-fluorophenyl)-3,5-dimethylpyridinato}(picolinate)iridium(III) (abbreviation: Ir(dmFppr)$_2$(pic)) were co-evaporated to form a 40-nm-thick film. Here, the evaporation rate was controlled so that the weight ratio of CzPz to PCBA1BP and Ir(dmFppr)$_2$(pic)) was 1:0.2:0.1 (=CzPz:PCBA1BP:Ir(dmFppr)$_2$(pic)).

Furthermore, on the third layer 913, a 10-nm-thick film of CzPz (abbreviation) and, thereon, a 20-nm-thick film of bathophenanthroline (abbreviation: BPhen) were formed by an evaporation method with resistive heating to form the fourth layer 914 which was an electron-transport layer.

On the fourth layer 914, a 1-nm-thick film of lithium fluoride (LiF) was formed as the fifth layer 915 which was an electron-injection layer.

Lastly, a 200-nm-thick film of aluminum was formed by an evaporation method with resistance heating to form the second electrode 903. In this manner, Light-Emitting Element 2 was formed.

The thus obtained Light-Emitting Element 2 was sealed in a glove box with a nitrogen atmosphere so as not to be exposed to air. Then, operation characteristics of Light-Emitting Element 2 were measured. Note that the measurements were carried out at room temperature (in an atmosphere kept at 25° C.).

Figure 18:
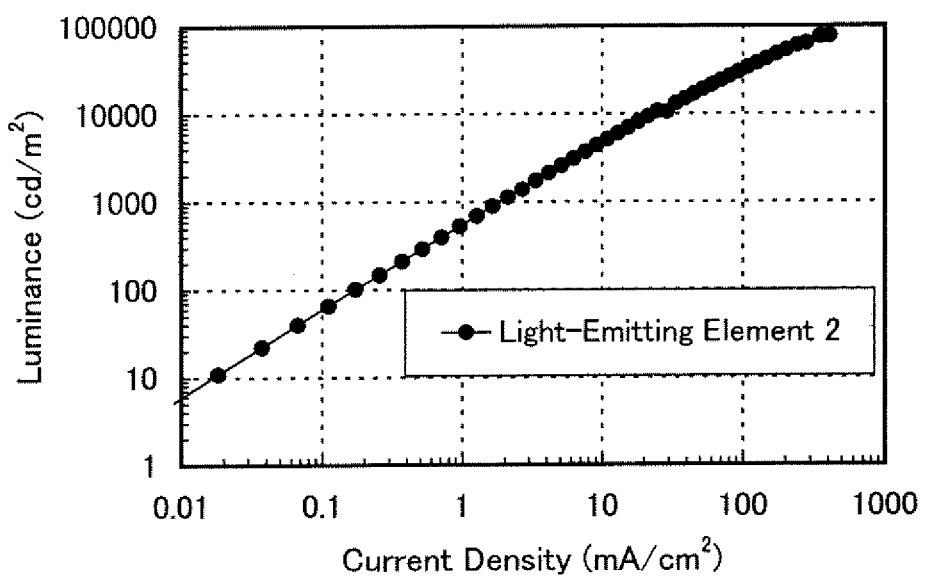
FIG. 18 shows current density-luminance characteristics of Light-Emitting Element 2.
Figure 19:
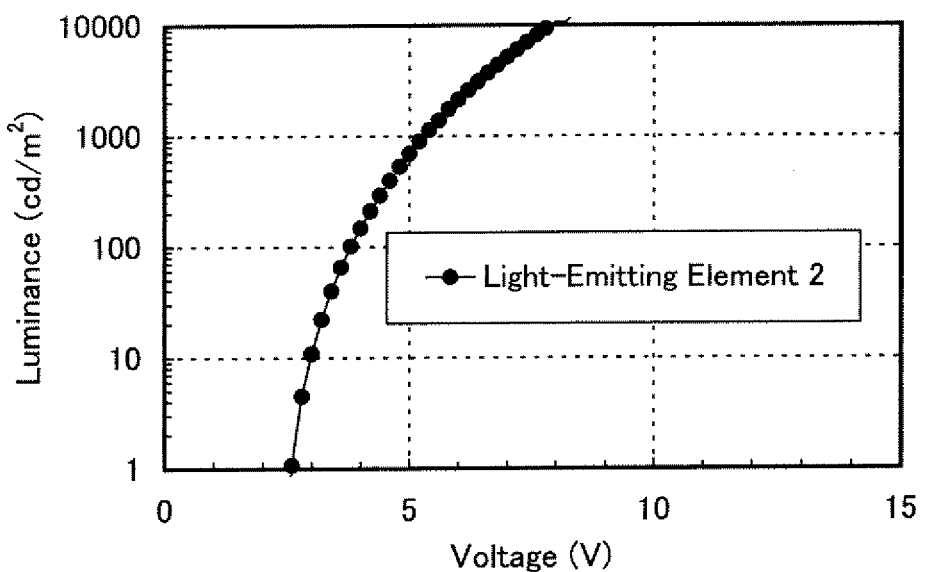
FIG. 19 shows voltage-luminance characteristics of Light-Emitting Element 2.
Figure 20:
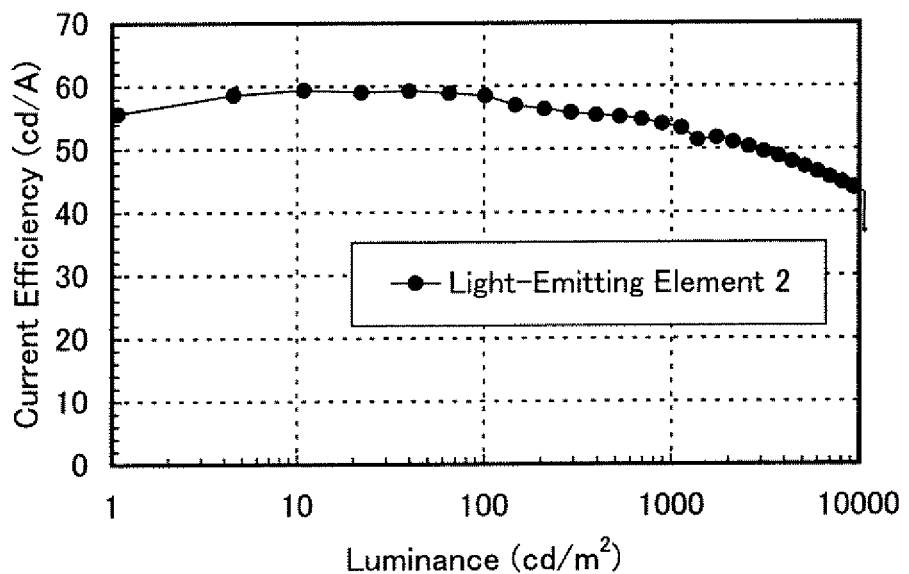
FIG. 20 shows luminance-current efficiency characteristics of Light-Emitting Element 2.

FIG. 18 shows current density-luminance characteristics, FIG. 19 shows voltage-luminance characteristics, and FIG. 20 shows luminance-current efficiency characteristics of Light-emitting Element 2. In FIG. 18, the vertical axis represents luminance (cd/m$^2$) and the horizontal axis represents current density (mA/cm$^2$). In FIG. 19, the vertical axis represents luminance (cd/m$^2$) and the horizontal axis represents voltage (V). In FIG. 20, the vertical axis represents current efficiency (cd/A) and the horizontal axis represents luminance (cd/m$^2$).

Note that in Light-Emitting Element 1, the voltage needed to obtain luminance of 893 cd/m$^2$ was 5.2 V. The current efficiency was 54.0 cd/A. Thus, it is found that the light-emitting element using the derivative with a heteroaromatic ring according to an embodiment of the present invention has high efficiency.

Figure 21:
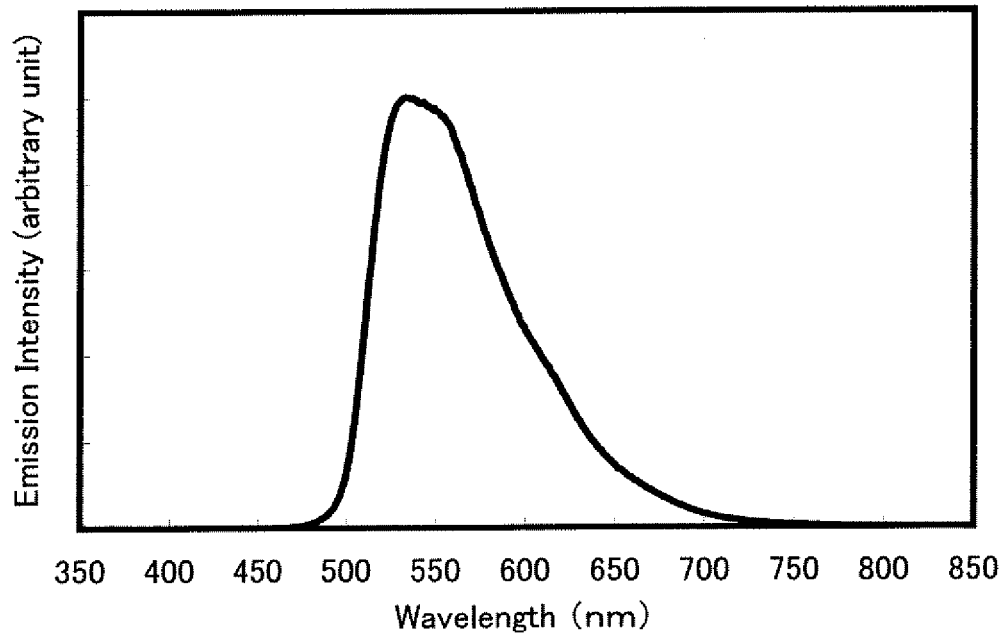
FIG. 21 shows an emission spectrum of Light-Emitting Element 2.

An emission spectrum of Light-Emitting Element 2 is shown in FIG. 21. As shown in FIG. 21, in Light-Emitting Element 2, an emission wavelength derived from Ir(dmFppr)$_2$(pic) (abbreviation) which was a guest material was observed, whereas an emission wavelength derived from CzPz (abbreviation), which was the derivative with a heteroaromatic ring according to an embodiment of the present invention and was a host material, was not observed. Therefore, it is confirmed that the derivative with a heteroaromatic ring according to an embodiment of the present invention serves as the host material having a bipolar property for the light-emitting layer of the light-emitting element.

REFERENCE EXAMPLE

A method for synthesizing 4-phenyl-4'-(9-phenyl-9H-carbazol-3-yl)triphenylamine (abbreviation: PCBA1BP), which is represented by Structural Formula (300), will be specifically described.

[Chemical Formula 83]

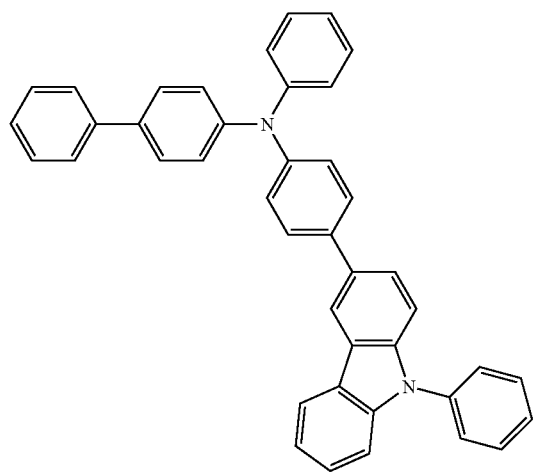

(300)

The synthetic scheme of 4-phenyl-4'-(9-phenyl-9H carbazol-3-yl)triphenylamine (abbreviation: PCBA1BP) is shown in (C-1).

[Chemical Formula 84]

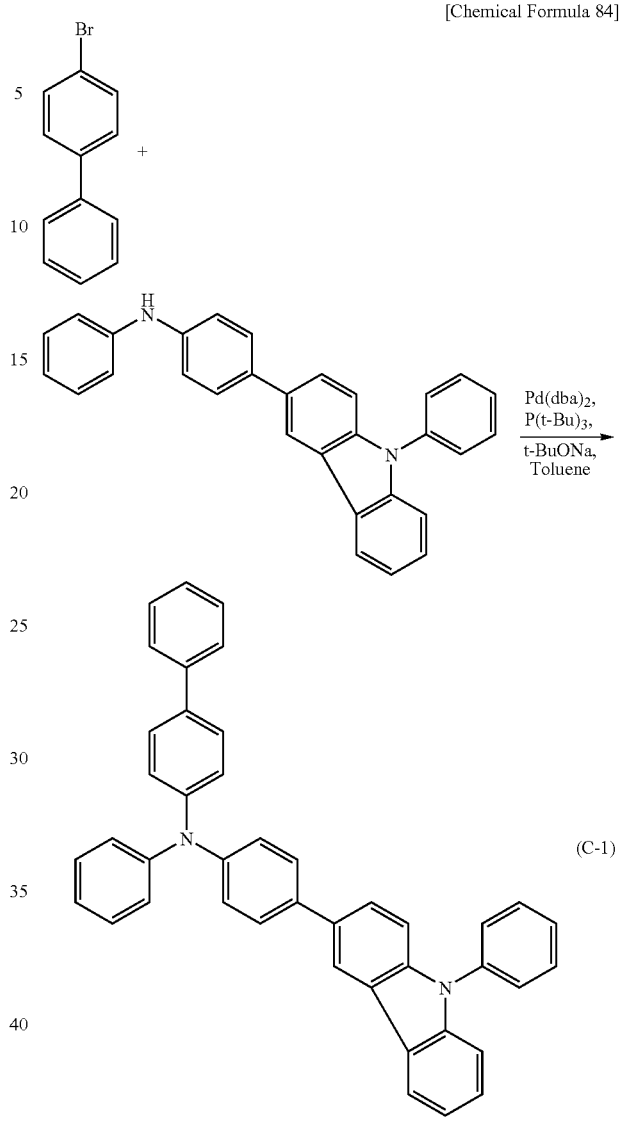

(C-1)

In a 100 mL three-necked flask were placed 2.0 g (4.9 mmol) of 4-(9-phenyl-9H-carbazol-3-yl)diphenylamine, 1.1 g (4.9 mmol) of 4-bromobiphenyl, and 2.0 g (20 mmol) of sodium tert-butoxide, and the atmosphere in the flask was replaced with nitrogen. To this mixture were added 50 mL of toluene and 0.30 mL of tri(tert-butyl)phosphine (10 wt % hexane solution).

This mixture was degassed while being stirred under reduced pressure. After that, 0.10 g of bis(dibenzylideneacetone)palladium(0) was added to the mixture. Next, this mixture was stirred at 80° C. for 5 hours while being heated, and reacted. After the reaction, toluene was added to the reaction mixture. The resulting suspension was suction filtered through Celite (Wako Pure Chemical Industries. Ltd., Catalog No. 531-16855), alumina, and Florisil (produced by Wako Pure Chemical Industries, Ltd., Catalog No. 540-00135). The resulting filtrate was washed with an aqueous solution of sodium carbonate and saturated saline in this order. Then, the organic layer was dried by addition of magnesium sulfate. After that, this mixture was suction filtered to remove the magnesium sulfate, whereby filtrate was obtained.

The obtained filtrate was concentrated and purified by silica gel column chromatography. The silica gel column chromatography was performed by, first, using a mixed solvent of a 1:9 ratio of toluene to hexane as a developing solvent, and then using a mixed solvent of a 3:7 ratio of toluene to hexane as another developing solvent. The obtained fractions were concentrated to give a solid, which was recrystallized with a mixed solvent of chloroform and hexane to give 2.3 g of a white powdered solid at 84% yield.

By a train sublimation method, 1.2 g of the obtained white solid was purified. Under a reduced pressure of 7.0 Pa with a flow rate of argon at 3 mL/min, the sublimation purification was carried out at 280° C. for 20 hours. The amount of the compound was 1.1 g, and the yield thereof was 89%.

The compound obtained by the above method was measured by a nuclear magnetic resonance ($^1$H NMR) method. The following are the measurement data: $^1$H NMR (DMSO-$d_6$, 300 MHz): δ (ppm)=7.05-7.20 (m, 7H), 7.28-7.78 (m, 21H), 8.34 (d, J=7.8 Hz, 1H), 8.57 (s, 1H).

The measurement results demonstrate that 4-phenyl-4'-(9-phenyl-9H-carbazol-3-yl)triphenylamine (abbreviation: PCBA1BP) represented by Structural Formula (300) was obtained.

By using 4-phenyl-4'-(9-phenyl-9H-carbazol-3-yl)triphenylamine (abbreviation: PCBA1BP), which was described above, Light-Emitting Elements 1 and 2 described in the above examples can be formed.

This application is based on Japanese Patent Application serial no. 2009-086528 filed with Japan Patent Office on Mar. 31, 2009, the entire contents of which are hereby incorporated by reference.

What is claimed is:

1. A compound represented by General Formula (G1) below,

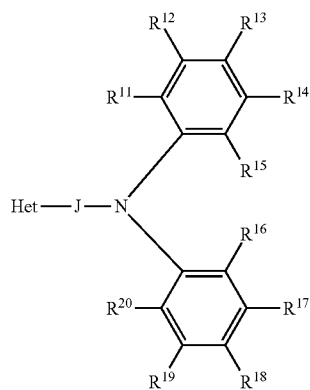

(G1)

wherein $R^{11}$ to $R^{20}$ are independently a hydrogen atom, an alkyl group having 1 to 4 carbon atoms, or a substituted or unsubstituted aryl group having 6 to 10 carbon atoms in a ring, J represents a substituted or unsubstituted arylene group having 6 to 12 carbon atoms in a ring, wherein Het is a substituent represented by General Formula (S1-2) below,

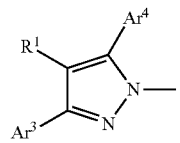

(S1-2)

wherein $Ar^3$ and $Ar^4$ are independently a substituted or unsubstituted aryl group having 6 to 10 carbon atoms in a ring, and $R^1$ is a hydrogen atom, an alkyl group having 1 to 4 carbon atoms, or an aryl group having 6 to 10 carbon atoms in a ring, and wherein the number of diphenylamine skeleton included in the compound is one.

2. A light-emitting element comprising a light-emitting layer, wherein the light-emitting layer comprises the compound according to claim 1.

3. A light-emitting element comprising a light-emitting layer, wherein the light-emitting layer comprises the compound according to claim 1 and a light-emitting substance.

4. The light-emitting element according to claim 3, wherein the light-emitting substance is a phosphorescent compound.

5. A light-emitting element comprising a layer comprising the compound according to claim 1, wherein the layer comprising the compound is provided in contact with a light-emitting layer.

6. A light-emitting device comprising the light-emitting element according to claim 2.

7. A light-emitting device comprising the light-emitting element according to claim 5.

8. An electronic device comprising the light-emitting device according to claim 6.

9. A lighting device comprising the light-emitting device according to claim 6.

10. A compound represented by General Formula (G2) below,

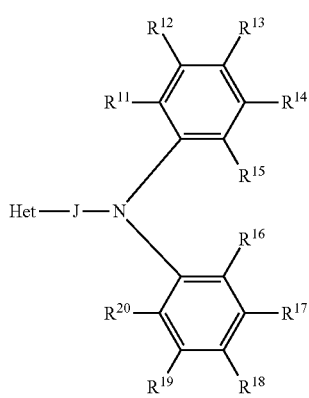

(G2)

wherein $R^{11}$ to $R^{20}$ are independently a hydrogen atom, an alkyl group having 1 to 4 carbon atoms, or a substituted or unsubstituted aryl group having 6 to 10 carbon atoms in a ring, J represents a substituted or unsubstituted arylene group having 6 to 12 carbon atoms in a ring, wherein Het is a substituent represented by General Formula (S2-2) below, (S2-2)

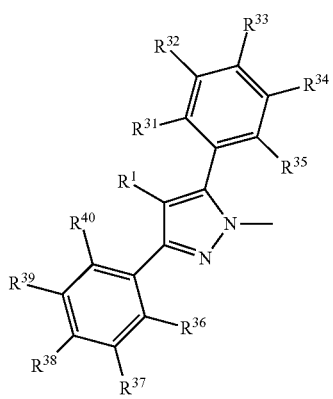

wherein $R^1$ and $R^{31}$ to $R^{40}$ are independently a hydrogen atom, an alkyl group having 1 to 4 carbon atoms, or an aryl group having 6 to 10 carbon atoms in a ring, and wherein the number of diphenylamine skeleton included in the compound is one.

11. The compound according to claim 10, wherein J represents phenylene group.

12. The compound according to claim 10, wherein J represents 1,4-phenylene group.

13. The compound according to claim 10, wherein J represents 1,4-phenylene group, and wherein $R^{31}$ to $R^{40}$ represent a hydrogen atom.

14. The compound according to claim 10, wherein J represents 1,4-phenylene group, wherein $R^{11}$ to $R^{20}$ represent a hydrogen atom, and wherein $R^{31}$ to $R^{40}$ represent a hydrogen atom.

15. A light-emitting element comprising a light-emitting layer, wherein the light-emitting layer comprises the compound according to claim 10.

16. A light-emitting element comprising a light-emitting layer, wherein the light-emitting layer comprises the compound according to claim 10 and a light-emitting substance.

17. The light-emitting element according to claim 16, wherein the light-emitting substance is a phosphorescent compound.

18. A light-emitting element comprising a layer comprising the compound according to claim 10, wherein the layer comprising the compound is provided in contact with a light-emitting layer.

19. A light-emitting device comprising the light-emitting element according to claim 15.

20. A light-emitting device comprising the light-emitting element according to claim 18.

21. An electronic device comprising the light-emitting device according to claim 19.

22. A lighting device comprising the light-emitting device according to claim 19.

* * * * *

UNITED STATES PATENT AND TRADEMARK OFFICE
CERTIFICATE OF CORRECTION

PATENT NO. : 8,551,625 B2
APPLICATION NO. : 12/750110
DATED : October 8, 2013
INVENTOR(S) : Hiroko Nomura et al.

It is certified that error appears in the above-identified patent and that said Letters Patent is hereby corrected as shown below:

In the Specification:

Col. 7, line 8, "skeleton. Bet is a" should read "skeleton. Het is a"

Col. 13, line 33, "In General Formula (S2-1)." should read "In General Formula (S2-1),"

Col. 80, line 50, "NPB), and s(3-meth-" should read "NPB), and N,N'-bis(3-meth-"

Col. 82, line 4, "N,N-bis[4-(9H-carbazol-9-yl)phenyl]-N,N'-diphenylstil-" should read "N,N'-bis[4-(9H-carbazol-9-yl)phenyl]-N,N'-diphenylstil-"

Col. 82, line 10, "9,10-bis(1,1'-biphenyl-2-yl)-2-anthryl]-N,9-diphenyl-9H-" should read "N-9,10-bis(1,1'-biphenyl-2-yl)-2-anthryl]-N,9-diphenyl-9H-"

Col. 83, line 6, "in addition, as a substance" should read "In addition, as a substance"

Col. 83, line 37, "(2,2%-bipyridine-6,6'-diyl)]" should read "(2,2'-bipyridine-6,6'-diyl)]"

Col. 90, line 18, "a curvature radius of 0.2 μm to 3" should read "a curvature radios of 0.2 μm to 3 μm."

Col. 95, line 67, "of is to 3s are considered" should read "of 1s to 3s are considered"

Signed and Sealed this
Eleventh Day of February, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,551,625 B2 | Page 1 of 1 |
| APPLICATION NO. | : 12/750110 | |
| DATED | : October 8, 2013 | |
| INVENTOR(S) | : Nomura et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 514 days.

Signed and Sealed this
Twenty-first Day of April, 2015

Michelle K. Lee
*Director of the United States Patent and Trademark Office*